US005639616A

United States Patent [19]
Liao et al.

[11] Patent Number: 5,639,616
[45] Date of Patent: Jun. 17, 1997

[54] ISOLATED NUCLEIC ACID ENCODING A UBIQUITOUS NUCLEAR RECEPTOR

[75] Inventors: Shutsung Liao, Chicago, Ill.; Ching Song, Durham, N.C.

[73] Assignee: Arch Development Corporation, Chicago, Ill.

[21] Appl. No.: 342,411

[22] Filed: Nov. 18, 1994

Related U.S. Application Data

[63] Continuation-in-part of Ser. No. 152,003, Nov. 10, 1993, abandoned.
[51] Int. Cl.$^6$ .............................. C12N 5/10; C12N 15/12
[52] U.S. Cl. ..................... 435/7.1; 435/69.1; 435/252.3; 435/320.1; 536/23.5; 536/24.3
[58] Field of Search .................................. 435/67.1, 69.1, 435/252.3, 320.1; 536/23.5, 24.3

[56] References Cited

PUBLICATIONS

Giguere et al, Nature 330:624–629, 17 Dec. 1997.Amero et al., The Origin of Nuclear Receptor Proteins: A Single Precursor Distinct from Other Transcription Factors,*Mol. Endo.*, 6:(1) 3-7, 1992.

Carlberg et al., Two nuclear signalling pathways for vitamin D,*Nature*, 361:657-660, 1993.

Carson-Jurica et al., Steroid Receptor Family: Structure and Functions, *Endocrine Reviews*, 11:(2) 201-220, 1990.

Diamond et al., Transcription Factor Interactions: Selectors of Positive or Negative Regulation from a Single DNA Element, *Science*, 249:1266-1272 , 1990.

Evans, R.M., The Steroid and Thyroid Hormone Receptor Superfamily, *Science*, 240:889-895, 1988.

Folkers et al., The Retinoic Acid Receptor-β2 Contains Two Separate Cell- Specific Transactivation Domains, at the N-Terminus and in the Ligand-Binding Domain, *Mol. Endo.*, 7:(4) 616-627, 1993.

Forman et al., Half-Site Spacing and Orientation Determines Whether Thyroid Hormone and Retinoic Acid Receptors and Related Factors Bind to DNA Response Elements as Monomers, Homodimers, or Heterodimers, *Mol. Endo.*, 6:(3) 429-442, 1992.

Forman, B.M., & Samuels, H.H., Dimerization among nuclear hormone receptors, *New Biol.*, 2:(7) 587-594, 1990.

Forman, B.M., & Samuels, H.H., Interactions Among a Subfamily of Nuclear Hormone Receptors: The Regulatory Zipper Model, *Mol. Endo.*, 4:(9) 1293-1301, 1990.

Forman et al., A Domain Containing Leucine-Zipper-Like Motifs Mediate Novel in Vivo Interactions between the Thyroid Hormone and Retinoic Acid Receptors, *Mol. Endo.*, 3:(10) 1610-1626, 1989.

Godowski et al., Signal Transduction and Transcriptional Regulation by Glucocorticoid Receptor-LexA Fusion Proteins, *Science*, 241:812-816, 1988.

Heery et al., Efficient transactivation by retinoic acid receptors in yeast requires retinoid X receptors, *Proc. Natl. Acad. Sci. USA*, 90:4281- 4285, 1993.

Herschman, H.R., Primary Response Genes Induced By Growth Factors And Tumor Promoters, *Annu. Rev. Biochem.*, 60:281-319, 1991.

Hiipakka, R.A. & Shutsung, L., Intracellar Inhibition of Chromatin Binding and Transformation of Androgen Receptor by 3'-Deoxyadenosine, The *J. Bio. Chem.*, 263:(33)17590-17595, 1988.

Kliewer et al., Convergence of 9-cis retinoic acid and peroxisome proliferator signalling pathways through heterodimer formation of their receptors, *Nature*, 358:771-774, 1992.

Kokontis et al., Expression and function of normal and LNCaP AR in androgen-insensitive human prostatic cancer cells: altered hormone and antihormone specificity in gene transactivation, *Receptor, 1:271-279, 1991.*

Kokontis et al., Transcriptional activation by TR3 receptor, a member of the steroid receptor superfamily, *Receptor*, 1:261-270, 1991.

Kozak, M., An analysis of 5'-noncoding sequences from 699 vertebrate messenger RNAs, *Nucleic Acid Research*, 15:(20) 8125-8132, 1087.

Lau, L.F. & Nathans, D., Expression of a set of growth-related immediate early genes in BALB/c 3T3 cells: Coordinate regulation with c-fos or c- myc, *Proc. Natl. Acad. Sci. USA*, 84:1182-1186, 1987.

Laudet et al., Evolution of the nuclear receptor gene superfamily, *EMBO J.*, 11:(3) 1003-1013, 1992.

Lazar, M.A., Thyroid Hormone Receptors: Multiple Forms, Multiple Possibilities, *Endocrine Reviews*, 14:(2) 184-193, 1993.

Leid et al., Purification, Cloning, and RXR Identity of the HeLa Cell Factor with Which RAR or TR Heterodimerizes to Bind Target Sequences Efficiently, Cell., 68:377-395, 1992.

Liao et al., Androgen Receptors: Structures, Mutations, Antibodies and Cellular Dynamics, *J. Steroid Biochem.*, 34:(1-6) 41-51, 1989.

Liao et al., RNA-dependent Release of Androgen * and Other Steroid * Receptor Complexes from DNA, *J. Biol. Chem., 255:(12) 5545-5551, 1980.*

(List continued on next page.)

Primary Examiner—Stephen G. Walsh
Assistant Examiner—John D. Ulm
Attorney, Agent, or Firm—Arnold White & Durkee

[57] ABSTRACT

The invention relates generally to compositions of and methods for obtaining ubiquitous, nuclear receptor (UR) polypeptides. The invention also relates to polynucleotides encoding UR polypeptides, recombinant host cells and vectors containing UR-encoding polynucleotide sequences, and recombinant UR polypeptides. By way of example, the invention discloses the cloning and functional expression of at least two different UR polypeptides. The invention also includes methods for using the isolated, recombinant receptor polypeptides in assays designed to select substances which interact with UR polypeptides for use in diagnostic, drug design and therapeutic applications.

17 Claims, 18 Drawing Sheets

PUBLICATIONS

Lucas, P.C. & Granner, D.K., Hormone Response Domains In Gene Transcription, *Annu. Rev. Biochem.*, 61:1131-1173, 1992.

McDonnell et al., Reconstitution of the Vitamin D-Responsive Osteocalcin Transcription Unit in *Saccharomyces cerevisiae*, 9:(8) 3517-3523, 1989.

Metzger et al., The human oestrogen receptor functions in yeast, *Nature*, 334:31-36, 1988.

Nakai et al., A Human Early Response Gene Homologous to Murine nur77 and Rat NGFI-B, and Related to the Nuclear Receptor Superfamily, *Mol. Endo.*, 4:(10) 1438-1443, 1990.

Nawaz et al., Identification of novel steroid-response elements, *Gene Expression*, 2:(1) 39-47, 1992.

Owen et al., Coordinate occupancy of AP-1 sites in the vitamin D-responsive and CCAAT box elements by Fos-Jun in the osteocalcin gene: Model for phenotype suppression of transcription, *Proc. Natl. Acad. Sci. USA*, 87:9990-9994, 1990.

Privalsky et al., The Viral erbA Oncogene Protein, a Constitutive Repressor in Animal Cells, Is a Hormone-Regulated Activator in Yeast, *Cell*, 63:1277-1286, 1990.

Purvis et al., An androgen-inducible expression system for *Saccharomyces cerevisiae*, *Gene*, 106:35-42, 1991.

Refetoff et al., The Syndromes of Resistance to Thyroid Hormone, *Endocrine Reviews*, 14:(3) 348-399, 1993.

Sai et al., An Exonic Point Mutation of the Androgen Receptor Gene in a Family with Complete Androgen Insensitivity, *Am. J. Hum. Genet.*, 46:1095-1100, 1990.

Schena, M. & Yamamoto, K.R., Mammalian Glucocorticoid Receptor Derivatives Enhance Transcription in Yeast, *Science*, 241:965-967, 1988.

Tasset et al., Distinct Classes of Transcriptional Activating Domains Function by Different Mechanisms, *Cell.*, 62:1177-1187, 1990.

Tora et al., The Human Estrogen Receptor Has Two Independent Nonacidic Transcriptional Activation Functions, *Cell.*, 59:477-487, 1989.

Truss, M. & Beato, M., Steroid Hormone Receptors: Interaction with Deoxyribonucleic Acid and Transcription Factors, *Endocrine Reviews*, 14:(4) 459-479, 1993.

Wang et al. COUP transcription factor is a member of the steroid receptor superfamily, *Nature*, 340:163-166, 1989.

Wilson et al., Identification of the DNA Binding Site for NGFI by Genetic Selection in Yeast, *Science*, 252:1296-1300, 1991.

Yang et al., Characterization of DNA binding and retinoic acid binding properties of retinoic acid receptor, *Proc. Natl. Acad. Sci. USA*, 88:3559-3563, 1991.

Yang-Yen et al., Transcriptional Interference between c-Jun and the Glucocorticoid Receptor: Mutual Inhibition of DNA Binding Due to Direct Protein-Protein Interaction, *Cell.*, 62:1205-1215, 1990.

Yu et al., RXRβ: A coregulator that enhances binding of retinoic acid, thyroid hormone, and vitamin D receptors to their cognate response elements, *Cell.*, 67:1251-1266, 1991.

Zelent et al., Cloning of murine α and β retinoic acid receptors and a novel receptor τ predominantly expressed in skin, *Nature*, 339:714-717, 1989.

Allan et al., "Ligand-dependent conformational changes in the progesterone receptor are necessary for events that follow DNA binding," *Proc. natl. Acad. Sci. USA*, 89:11750-11754, 1992.

Blanar and Rutter, "Interaction Cloning: Identification of a Helix-Loop-Helix Zipper Protein That Interacts with c-Fos," *Science*, 256:1014-1018, 1992.

Davis et al., "Transcriptional activation by Nur77, a growth factor-inducible member of the steroid hormone receptor superfamily," *Mol. Endocrinol*"., 5:854-859, 1991.

Freedman, "Anatomy of the Steroid Receptor Zinc Finger Region," *Endocrine Reviews*, 13(2):129-145, 1992.

Hiipakka et al., "Expression of a 5α-reductase in bacteria as a trp E fusion protein and its use in the production of antibodies for immunocytochemical localization of 5α-reductase, *J. Steroid Biochem.*, 45:539-548, 1993.

LaCasse et al., "Identification of Binding Proteins for Nuclear Localization Signals of the Glucocorticoid and Thyroid Hormone Receptors," *Endocrinology*, 132(3):1017-1025, 1993.

Lee et al., "Structure of the Retinoid X Receptor α DNA Binding Domain: A Helix Required for Homodimeric DNA Binding," *Science*, 260:1117-1121, 1993.

Liang and Pardee, "Differential Display of Eukaryotic Messenger RNA by Means of the Polymerase Chain Reaction," *Science*, 257:967-971, 1992.

Lynch et al., "Steroidogenic Factor 1, an Orphan Nuclear Receptor, Regulates the Expression of the Rat Aromatase Gene in Gonadal Tissues," *Molecular Endocrinology*, 7(6):776-786, 1993.

Marks et al., "H-2RIIBP (RXRβ) heterodimerization provides a mechanism for combinatorial diversity in the regulation of retinoic acid and thyroid hormone responsive genes," *The EMBO Journal*, 11(4):1419-1435, 1992.

Nakada et al., "The Androgen Receptor Status of Neuroendocrine Cells in Human Benign and Malignant Prostatic Tissue," *Cancer Research*, 53:1967-1970, 1993.

O'Malley and Conneely, "Orphan receptors: in search of a unifying hypothesis for activation," *Mol. Endocrinol.*, 6:1359-1361, 1992.

Rennie et al., "Characterization of Two Cis-Acting DNA Elements Involved in the Androgen Regulation of the Probasin Gene," *Molecular Endocrinology*, 7(1):23-36, 1993.

Wagner et al., "Myc-Mediated Apoptosis is Blocked by Ectopic Expression of Bcl-2," *Molecular and Cellular Biology*, 13(4):2432-2440, 1993.

Wilson et al., "Participation of Non-Zinc Finger Residues in DNA Binding by Two Nuclear Orphan Receptors," *Science*, 256:107-110, 1992.

Wilson et al., "The Orphan Receptors NGFI-B and Steroidogenic Factor 1 Establish Monomer Binding as a Third Paradigm of Nuclear Receptor-DNA Interaction," *Molecular and Cellular Biology*, 13(9):5794-5804, 1993.

| | |
|---|---:|
| MSSPTSSLDTPLPGNGPPQPGAPSSSPTVKEEGPEPWPGGPDPDVPGTDE | 50 |
| ASSACSTDWVIPDPEEEPERKRKKGPAPKMLGHELCRVCGDKASGFHYNV | 100 |
| LSCEGCKGFFRRSVVRGGARRYACRGGGTCQMDAFMRRKCQQCRLRKCKE | 150 |
| AGMREQCVLSEEQIRKKKIRKQQQEESQSQSPVGPQGSSSSASGPGAS | 200 |
| PGGSEAGSQGSGEGEGVQLTAAQELMIQQLVAAQLQCNKRSFSDQPKVTP | 250 |
| WPLGADPQSRDARQQRFAHFTELAIISVQEIVDFAKQVPGFLQLGREDQI | 300 |
| ALLKASTIEIMLLETARRYNHETECITFLKDFTYSKDDFHRAGLQVEFIN | 350 |
| PIFEFSRAMRRLGLDDAEYALLIAINIFSADRPNVQEPGRVEALQQPYVE | 400 |
| ALLSYTRIKRPQDQLRFPRMLMKLVSLRTLSSVHSEQVFALRLQDKKLPP | 450 |
| LLSEIWDVHE | 460 |

FIG. 1A

MSSPTSSLDTPLPGNGSPQPSTSTSPTIKEEVQETDPPPGSEGSSSAYI 50
VEPEDEPERKRKKGPAPKMLGHELCRVCGDKASGFHYNVLSCEGCKGFFR 100
RSVVHGGAGRYACRGSGTCQMDAFMRRKCQLCRLRKCKEAGMREQCVLSE 150
EQIRKKKIQKQQQQPPPTEPASGSSARPAASPGTSEASSQGSGEGEGI 200
QLTAAQELMIQQLVAVQLQCNKRSFSDQPKVTPWPLGADPQSRDARQQRF 250
AHFTELAIISVQEIVDFAKQVPGFLQLGREDQIALLKASTIEIMLLETAR 300
RYNHETECITFLKDFTYSKDDFHRAGLQVEFINPIFEFSRAMRRLGLDDA 350
EYALLIAINIFSADRPNVQEPSRVEALQQPYVEALLSYTRIKRPQDQLRF 400
PRMLMKLVSLRTLSSVHSEQVFALRLQDKKLPPLLSEIWDVHE 443

FIG. 1B

```
AGTTCCCTGG ATACCCCCCT GCCTGAAAT  GGCCCCCCTC AGCCTGGCGC CCCTTCTCT  TCACCCACTG TAAAGGAGGA   80
GGGTCCGGAG CCGTGGCCCG GGGGTCCGGA CCCTGATGTC CCAGGCACTG ATGAGGCCAG CTCAGCCTGC AGCACAGACT  160
GGGTCATCCC AGATCCCGAA GAGGAACCAG AGCGCAAGAG TTCCACTACA ACGTGCTCAG CCAGCCCCGA AGATGCTGGG CCACGAGCTT  240
TGCCGTGTCT GTGGGGACAA GGCCCTCCGC TTCCACTACA ACGTGCTCAG CTGCGAAGGC TGCAAGGGCT TCTTCCGGCG  320
CAGTGTGGTC CGTGGTGGGG CCAGGCGCTA TGCCTGCCGG GGTGGCCGGA CCTGCCAGAT GGACGCTTTC ATGCGGCGCA  400
AGTGCCAGCA GTGCCGGCTG CGCAAGTGCA AGGAGGCAGG GATGAGGGAG CAGTGCGTCC TTTCTGAAGA ACAGATCCGG  480
AAGAAGAAGA TTCGGAAACA GCAGCAGCAG GAGTCACAGT CACAGTCGCA GTCACCTGTG GGGCCGCAGG GCAGCAGCAG  560
CTCAGCCTCT GGGCCTGGGG CTTCCCCTGG TGGATCTGAG GCAGGCAGCC AGGGCTCCGG GGAAGGAGAG GGTGTCCAGC  640
TAACAGCGGC TCAAGAACTA ATGATCCAGC AGTTGGTGGC GGCCCAACTG CAGTGCAACA AACGCTCCTT CTCCGACCAG  720
CCCAAAGTCA CGCCCCTGGC CCTGGGGGCA GACCCCCAGT CCCGAGATGC CCGCCAGCAA CGCTTTGCCC ACTTCACGGA  800
GCTGGCCATC ATCTCAGTCC AGGAGATCGT GGACTTCGCT AAGCAAGTGC CTGGTTTCCT GCAGCTGGGC CGGGAGGACC  880
AGATCGCCCT CCTGAAGGCA TCCACTATCG AGATCATGCT GCTAGAGACA GCCAGGCGCT ACAACCACGA GACAGAGTGT  960
ATCACCTTCT TGAAGGACTT CACCTACAGC AAGGACGACT TCCACCGTGC AGGGAGTTCA GTGGAGTTCA TCAACCCCAT 1040
CTTCGAGTTC TCGCGGGCCA TGCGGCGGCT GGGCCTGGAC GACGCTGAGT ACGCCCTGCT CATCGCCATC AACATCTTCT 1120
CGGCCGACCG GCCTAATGTG CAGGAGCCGG GCCGGGTGGA GGCGTTGCAG CAGCCCTACG TGGAGGCGCT GCTGTCCTAC 1200
ACGCGCATCA AGAGGCCGCA GGACCAGCTG CGCTTCCCGC GCATGCTCAT GAAGAGCTGC CGCCTCTGCT GGGACGTCC  1280
TGTGCACTCG GAGCAGGTCT TCGCCTTGCG GCTCCAGGAC AAGAAGCTGC CGCCTCTGCT GTCGGAGATC CCCTTCCTCT 1360
ACGAGTGAGG GGCTGGCCAC CCAGCCCCAC AGCCCTTGCCT GACCACCCTC CAGCAGATAG ACGCCGGGAC CCCTTCCTCT 1440
ACGAGTGAGG GGCTGGCCAC CCAGCCCCAC AGCCCTTGCCT GACCACCCTC CAGCAGATAG ACGCCGGGAC CCCTTCCTCT 1440
TCCTAGGGTG GAAGGGCCCC TGGGCCGAGC CTGTAGACCT CTGTAGGGTT GAAAGGGT  ATAAGCCCCA GTCCAGGTCC 1520
AGGAGGCTCC CTCCCCTGCC AGCGAGTCTT CCAGAAGGGG TGAAAGGGT  GCAGGTCCCG ACCACTGACC CTTCCCGGCT 1600
GCCCTCCCTC CCCAGCTTAC ACCTCAAGCC CAGACGCAGT GCACCTTGAA GCACCTTGAA AAAAACTAAA TGGCTCTCCC 1680
CCCTAGCCCG GGAGACCAGG GGCCTTCCCTC TTCCTCTGCT TTTATTTAAT AAAAACTAAA AACAGAAAAA AAAAAAAAA 1760
AAAAAAAAAA AAAAAAAAAA AAAAAAAAAA AAAAAGGAAT TCC                                        1813
```

FIG. 1C

```
GGAATTCGGC ACGAGCACGC AAGGCTGTTG CTCCGAGCTA CTCCCAGGCT TCTGAAGTTA CTTCTGAAGT GCTGTGGAGG     80
AGCAATCACC GGTGCGGACA CAGAGCTCCC GCCTCCCACA GCCATTTCCA GGGTAACGAA GTAGGAGACC CCCTCCTGCG    160
ACCCCCTCAC GATCGCCGGT GCAGTCATGA CCCCTGGTGC ACGGAGAGGG ACGGAGACCTG GCGGGGCCTG GAACGAGGCT   240
GCTTCGTGAC CCACTATGTC TTCCCCCACA AGTTCTCTGG GCCTGGAAT GGTTCTCCCC AGCCCAGTAC                320
CTCCTCCACT TCACCCACTA TTAAGGAGGA GGTACAGAGA ACTGATCCAC CTCCAGGCTC TGAAGGGTCC AGCTCTGCCT    400
ACATCGTGGA GCCAGAGGAT GAACCTGAGC GCAAGCGGAA GAAGGGTCCG GCCCCGAAGA TGCTGGGCCA TGAGCTGTGC    480
CGCGTGTGCG GGGACAAGGC CTCGGGCTTC CACTACAATG TGCTCAGTTG TGAAGGCTGC AAAGGCTTCT TCCGGCGTAG    560
CGTGGTCCAT GGTGGGGCCG GGCGCTATGC CTGTCGGGGC AGCGGAACCT GCCAGATGGA TGCCCTTCATG CGGGCGAAGT   640
GCCAGCTCTG CAGACTGCGC AAGTGCAAGG AGGCTGGCAT GCGGGAGCAG TGCGTGCTTT CTGAGGAGCA GATTCGGAAG    720
AAAAAGATTC AGAAGCAGCA ACACCGGCCC CGACTGAGCC AGCATCCGGT AGCTCAGCCC GGCCTGCAGC                800
CTCCCCTGGC ACTTCGGAAG CAAGTAGCCA GGGCTCCGGG GAAGGAGAGG GCATCCAGCT GACAGCGGCT CAGGAGCTGA    880
TGATCCAACA GTTAGTTGCC GTGCAGCTGC AGTGCAACAA GCGATCTTTC TCCGACCAGC CTAAAGTCAC GCCCTGGCCC    960
TTGGGTGCAG ACCCTCAGTC CCGAGACGCT GCTTTGCCCA CTTCACTGAG CTAGCCATCA TCTCAGTCCA               1040
GGAGATCGTG GACTTCGCCA AGGGTTGCC CAGCTGGGCC GGGAGGACCA GATCGCCCTC CTGAAGGCAT                1120
CCACCATCGA GATCATGTTG CTAGAGACAG CCAGACGCTA CATGCGGCA TCACGTTCCT GAAGGACTTC                1200
ACCTACAGCA AGGACGACTT CCACCGTGCA GGCTTGCAGG TGGAGTTCAT CAATCCCCATC TTTGAGTTCT CTCGGGCTAT   1280
GCGTCGGCTG GCCTAGACG ATGCAGAGTA TGCCCTTGCTC AGCCCCTATGT GGAGGCCCTC CTCTCCTACA CGAGGATCAA GCGGCCGCAG 1360
AGGAGCCCAG CCGTCTGGAG GCTCTGCAGC ACTCTGGTGA AGCCCTATGT AAGCTGGTGA GCCTGGCGAC CGAGGATCAA GCGGCCGCAG 1440
GACCAGCTGC GCTTCCCACG AATGCTCATG AAGCTGGTGA GCCTTGGCTG CTGCACTCGG AGCAGTTTT                1520
CGCATTGCGT CTCCAGGACA AGAAGCTTCG GCCTTTGCTG ATGGACGCTT CCCTTTGCCTT TCCTGGGGTG GGAGGACACT GTCACAGCCG 1600
TGCCCCAGCC TTGGTGGTGT CTACTTGCAG ATGGACGCTT CCCTTTGCCTT TCCTGGGGTG GGAGGACACT GTCACAGCCG 1680
AGTCCCCTGG GCTCGGGCTG AGCGAGTGGC AGTTGGCACT ACCCACCTCC AGAAGGTCCC ACCCCACCCG CTGAGTCTTC CAGGAGTGT   1760
GAGGGTCACA GGCCCTAGCC TCTGATCTTT ACCAGCTGCC CTTCCTCCCG AGCTTACACC TCAGCCTACC ACACCATGCA              1840
CCTTGAGTGG AGAGAGGTTA GGGCAGGTGG CTCCCCACAG TTGGGAGACC ACAGGCCCCC TCTTCTGCCC CTTTTATTTA              1920
ATAAAAAAAAA TAAAATAAAA TAAAGCTCGT GCCGAATTC                                                          1959
```

FIG. 1D

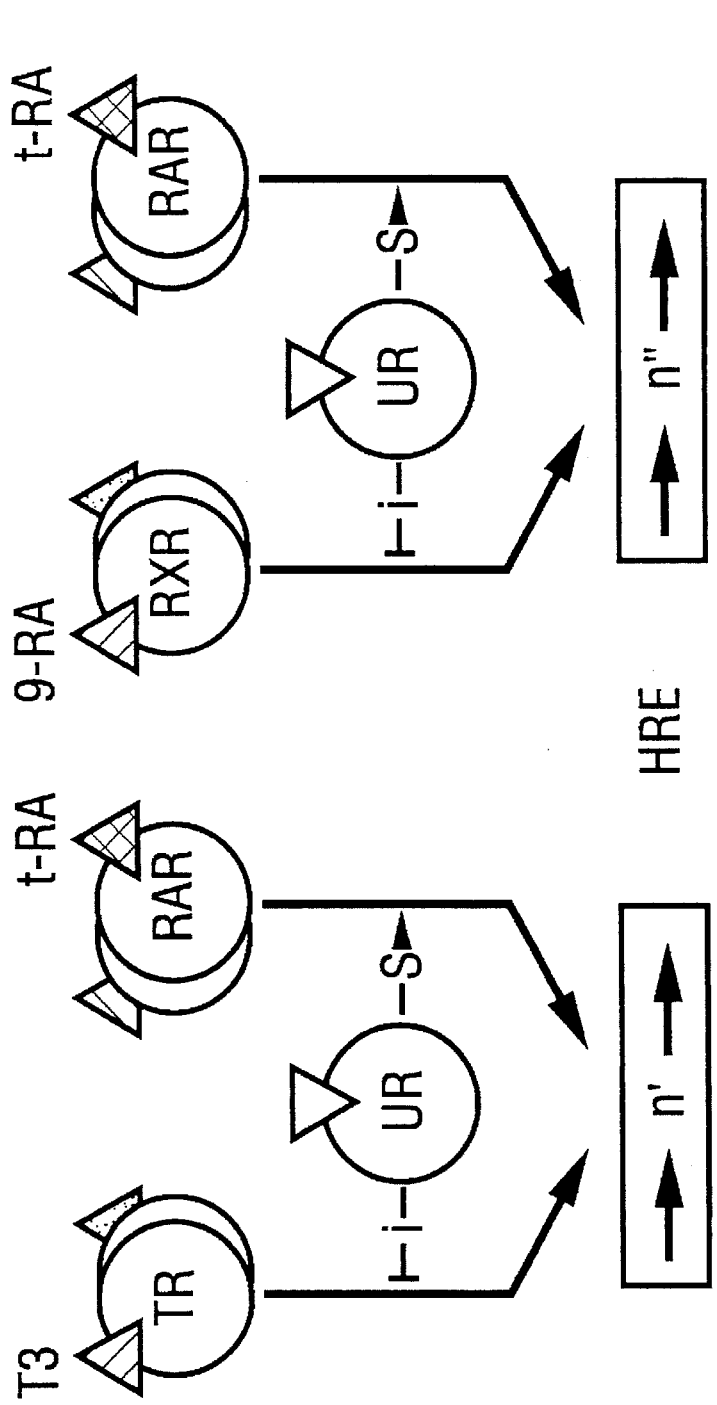
FIG. 7

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:
( A ) LENGTH: 1898 base pairs
( B ) TYPE: nucleic acid
( C ) STRANDEDNESS: single
( D ) TOPOLOGY: linear ( i x ) FEATURE:
( A ) NAME/KEY: CDS
( B ) LOCATION: 71..1450

( x i ) SEQUENCE DESCRIPTION: SEQ ID NO:1:

```
AAAAAGGAAC TTGAAGCCTT GATACTACTA CCTCTAGCAA GCTTACCTGA TCTAATCTGT         60

ATGACCCACC ATG TCT ACT CCC ACA AGT TCC CTG GAT ACC CCC CTG CCT          109
           Met Ser Thr Pro Thr Ser Ser Leu Asp Thr Pro Leu Pro
             1               5                   10

GGA AAT GGC CCC CCT CAG CCT GGC GCC CCT TCC TCT TCA CCC ACT GTA          157
Gly Asn Gly Pro Pro Gln Pro Gly Ala Pro Ser Ser Ser Pro Thr Val
         15                  20                  25

AAG GAG GAG GGT CCG GAG CCG TGG CCC GGG GGT CCG GAC CCT GAT GTC          205
Lys Glu Glu Gly Pro Glu Pro Trp Pro Gly Gly Pro Asp Pro Asp Val
 30                  35                  40                  45

CCA GGC ACT GAT GAG GCC AGC TCA GCC TGC AGC ACA GAC TGG GTC ATC          253
Pro Gly Thr Asp Glu Ala Ser Ser Ala Cys Ser Thr Asp Trp Val Ile
                 50                  55                  60

CCA GAT CCC GAA GAG GAA CCA GAG CGC AAG AGA AAG AAG GGC CCA GCC          301
Pro Asp Pro Glu Glu Glu Pro Glu Arg Lys Arg Lys Lys Gly Pro Ala
             65                  70                  75

CCG AGG ATG CTG GGC CAC GAG CTT TGC CGT GTC TGT GGG GAC AAG GCC          349
Pro Arg Met Leu Gly His Glu Leu Cys Arg Val Cys Gly Asp Lys Ala
         80                  85                  90

TCC GGC TTC CAC TAC AAC GTG CTC GAC TGC GAA GGC TGC AAG GGC TTC          397
Ser Gly Phe His Tyr Asn Val Leu Asp Cys Glu Gly Cys Lys Gly Phe
     95                 100                 105

TTC CGG CGC AGT GTG GTC CGT GGT GGG GCC AGG CGC TAT GCC TGC CGG          445
Phe Arg Arg Ser Val Val Arg Gly Gly Ala Arg Arg Tyr Ala Cys Arg
110                 115                 120                 125

GGT GGC GGA ACC TGC CAG ATG GAC GCT TTC ATG CGG CGC AAG TGC CAG          493
Gly Gly Gly Thr Cys Gln Met Asp Ala Phe Met Arg Arg Lys Cys Gln
                130                 135                 140

CAG TGC CGG CTG CGC AAG TGC AAG GAG GCA GGG ATG AGG GAG CAG TGC          541
Gln Cys Arg Leu Arg Lys Cys Lys Glu Ala Gly Met Arg Glu Gln Cys
            145                 150                 155

GTC CTT TCT GAA GAA CAG ATC CGG AAG AAG AAG ATT CGG AAA CAG CAG          589
Val Leu Ser Glu Glu Gln Ile Arg Lys Lys Lys Ile Arg Lys Gln Gln
        160                 165                 170

CAG CAG CAG TCA CAG TCA CAG TCG CAG TCA CCT GTG GGG CCG CAG GGC          637
Gln Gln Gln Ser Gln Ser Gln Ser Gln Ser Pro Val Gly Pro Gln Gly
    175                 180                 185

AGC AGC AGC TCA GCC TCT GGG CCT GGG GCT TCC CCT GGT GGA TCT GAG          685
Ser Ser Ser Ser Ala Ser Gly Pro Gly Ala Ser Pro Gly Gly Ser Glu
190                 195                 200                 205

GCA GGC AGC CAG GGC TCC GGG GAA GGA GAG GGT GTC CAG CTA ACA GCG          733
Ala Gly Ser Gln Gly Ser Gly Glu Gly Glu Gly Val Gln Leu Thr Ala
                210                 215                 220
```

| | |
|---|---|
| GCT CAA GAA CTA ATG ATC CAG CAG TTG GTG GCG GCC CAA CTG CAG TGC<br>Ala Gln Glu Leu Met Ile Gln Gln Leu Val Ala Ala Gln Leu Gln Cys<br>225 230 235 | 781 |
| AAC AAA CGC TCC TTC TCC GAC CAG CCC AAA GTC ACG CCC TGG CCC CTG<br>Asn Lys Arg Ser Phe Ser Asp Gln Pro Lys Val Thr Pro Trp Pro Leu<br>240 245 250 | 829 |
| GGC GCA GAC CCC CAG TCC CGA GAT GCC CGC CAG CAA CGC TTT GCC CAC<br>Gly Ala Asp Pro Gln Ser Arg Asp Ala Arg Gln Gln Arg Phe Ala His<br>255 260 265 | 877 |
| TTC ACG GAG CTG GCC ATC ATC TCA GTC CAG GAG ATC GTG GAC TTC GCT<br>Phe Thr Glu Leu Ala Ile Ile Ser Val Gln Glu Ile Val Asp Phe Ala<br>270 275 280 285 | 925 |
| AAG CAA GTG CCT GGT TTC CTG CAG CTG GGC CGG GAG GAC CAG ATC GCC<br>Lys Gln Val Pro Gly Phe Leu Gln Leu Gly Arg Glu Asp Gln Ile Ala<br>290 295 300 | 973 |
| CTC CTG AAG GCA TCC ACT ATC GAG ATC ATG CTG CTA GAG ACA GCC AGG<br>Leu Leu Lys Ala Ser Thr Ile Glu Ile Met Leu Leu Glu Thr Ala Arg<br>305 310 315 | 1021 |
| CGC TAC AAC CAC GAG ACA GAG TGT ATC ACC TTC TTG AAG GAC TTC ACC<br>Arg Tyr Asn His Glu Thr Glu Cys Ile Thr Phe Leu Lys Asp Phe Thr<br>320 325 330 | 1069 |
| TAC AGC AAG GAC GAC TTC CAC CGT GCA GGC CTG CAG GTG GAG TTC ATC<br>Tyr Ser Lys Asp Asp Phe His Arg Ala Gly Leu Gln Val Glu Phe Ile<br>335 340 345 | 1117 |
| AAC CCC ATC TTC GAG TTC TCG CGG GCC ATG CGG CGG CTG GGC CTG GAC<br>Asn Pro Ile Phe Glu Phe Ser Arg Ala Met Arg Arg Leu Gly Leu Asp<br>350 355 360 365 | 1165 |
| GAC GCT GAG TAC GCC CTG CTC ATC GCC ATC AAC ATC TTC TCG GCC GAC<br>Asp Ala Glu Tyr Ala Leu Leu Ile Ala Ile Asn Ile Phe Ser Ala Asp<br>370 375 380 | 1213 |
| CGG CCT AAT GTG CAG GAG CCG GGC CGC GTG GAG GCG TTG CAG CAG CCC<br>Arg Pro Asn Val Gln Glu Pro Gly Arg Val Glu Ala Leu Gln Gln Pro<br>385 390 395 | 1261 |
| TAC GTG GAG GCG CTG CTG TCC TAC ACG CGC TAC AAG AGG CCG CAG GAC<br>Tyr Val Glu Ala Leu Leu Ser Tyr Thr Arg Tyr Lys Arg Pro Gln Asp<br>400 405 410 | 1309 |
| CAG CTG CGC TTC CCG CGC ATG CTC ATG AAG CTG GTG AGC CTG CGC ACC<br>Gln Leu Arg Phe Pro Arg Met Leu Met Lys Leu Val Ser Leu Arg Thr<br>415 420 425 | 1357 |
| CTG AGC TCT GTG CAC TCG GAG CAG GTC TTC GCC TTG CGG CTC CAG GAC<br>Leu Ser Ser Val His Ser Glu Gln Val Phe Ala Leu Arg Leu Gln Asp<br>430 435 440 445 | 1405 |
| AAG AAG CTG CCG CCT CTG CTG TCG GAG ATC TGG GAC GTC GAC GAG<br>Lys Lys Leu Pro Pro Leu Leu Ser Glu Ile Trp Asp Val Asp Glu<br>450 455 460 | 1450 |
| TGAGGGGCTG GCCACCCAGC CCACAGCCT TGCCTGACCA CCCTCCAGCA GATAGACGCC | 1510 |
| GGCACCCCTT CCTCTTCCTA GGGTGGAAGG GGCCCTGGGC CGAGCCTGTA GACCTATCGG | 1570 |
| CTCTCATCCC TTGGGATAAG CCCCAGTCCA GGTCCAGGAG GCTCCCTCCC TGCCCAGCGA | 1630 |
| GTCTTCCAGA AGGGGTGAAA GGGTTGCAGG TCCCGACCAC TGACCCTTCC CGGCTGCCCT | 1690 |
| CCCTCCCCAG CTTACACCTC AAGCCCAGAC GCAGTGCACC TTGAACAGAG GGAGGGGAGG | 1750 |
| ACCCATGGCT CTCCCCCCTA GCCCGGGAGA CCAGGGGCCT TCCTCTTCCT CTGGTTTTAT | 1810 |
| TTAATAAAAA CTAAAACAG AAAAAAAAAA AAAAAAAAA AAAAAAAAA AAAAAAAAA | 1870 |
| AAAAAAAAAA AAAAAAAAA GGAATTCC | 1898 |

( 2 ) INFORMATION FOR SEQ ID NO:2:

( i ) SEQUENCE CHARACTERISTICS:
  ( A ) LENGTH: 460 amino acids
  ( B ) TYPE: amino acid
  ( D ) TOPOLOGY: linear ( x i ) SEQUENCE DESCRIPTION: SEQ ID NO:2:

```
Met  Ser  Thr  Pro  Thr  Ser  Ser  Leu  Asp  Thr  Pro  Leu  Pro  Gly  Asn  Gly
 1              5                   10                  15

Pro  Pro  Gln  Pro  Gly  Ala  Pro  Ser  Ser  Pro  Thr  Val  Lys  Glu  Glu
              20                  25                  30

Gly  Pro  Glu  Pro  Trp  Pro  Gly  Gly  Pro  Asp  Pro  Asp  Val  Pro  Gly  Thr
          35                  40                  45

Asp  Glu  Ala  Ser  Ser  Ala  Cys  Ser  Thr  Asp  Trp  Val  Ile  Pro  Asp  Pro
     50                  55                  60

Glu  Glu  Glu  Pro  Glu  Arg  Lys  Arg  Lys  Lys  Gly  Pro  Ala  Pro  Arg  Met
 65                  70                  75                               80

Leu  Gly  His  Glu  Leu  Cys  Arg  Val  Cys  Gly  Asp  Lys  Ala  Ser  Gly  Phe
               85                  90                  95

His  Tyr  Asn  Val  Leu  Asp  Cys  Glu  Gly  Cys  Lys  Gly  Phe  Phe  Arg  Arg
              100                 105                 110

Ser  Val  Val  Arg  Gly  Gly  Ala  Arg  Arg  Tyr  Ala  Cys  Arg  Gly  Gly  Gly
          115                 120                 125

Thr  Cys  Gln  Met  Asp  Ala  Phe  Met  Arg  Arg  Lys  Cys  Gln  Gln  Cys  Arg
     130                 135                 140

Leu  Arg  Lys  Cys  Lys  Glu  Ala  Gly  Met  Arg  Glu  Gln  Cys  Val  Leu  Ser
145                 150                 155                      160

Glu  Glu  Gln  Ile  Arg  Lys  Lys  Lys  Ile  Arg  Lys  Gln  Gln  Gln  Gln  Gln
              165                 170                 175

Ser  Gln  Ser  Gln  Ser  Gln  Ser  Pro  Val  Gly  Pro  Gln  Gly  Ser  Ser  Ser
          180                 185                 190

Ser  Ala  Ser  Gly  Pro  Gly  Ala  Ser  Pro  Gly  Gly  Ser  Glu  Ala  Gly  Ser
          195                 200                 205

Gln  Gly  Ser  Gly  Glu  Gly  Glu  Gly  Val  Gln  Leu  Thr  Ala  Ala  Gln  Glu
     210                 215                 220

Leu  Met  Ile  Gln  Gln  Leu  Val  Ala  Ala  Gln  Leu  Gln  Cys  Asn  Lys  Arg
225                 230                 235                      240

Ser  Phe  Ser  Asp  Gln  Pro  Lys  Val  Thr  Pro  Trp  Pro  Leu  Gly  Ala  Asp
              245                 250                 255

Pro  Gln  Ser  Arg  Asp  Ala  Arg  Gln  Gln  Arg  Phe  Ala  His  Phe  Thr  Glu
          260                 265                 270

Leu  Ala  Ile  Ile  Ser  Val  Gln  Glu  Ile  Val  Asp  Phe  Ala  Lys  Gln  Val
          275                 280                 285

Pro  Gly  Phe  Leu  Gln  Leu  Gly  Arg  Glu  Asp  Gln  Ile  Ala  Leu  Leu  Lys
     290                 295                 300

Ala  Ser  Thr  Ile  Glu  Ile  Met  Leu  Leu  Glu  Thr  Ala  Arg  Arg  Tyr  Asn
305                 310                 315                      320

His  Glu  Thr  Glu  Cys  Ile  Thr  Phe  Leu  Lys  Asp  Phe  Thr  Tyr  Ser  Lys
              325                 330                 335

Asp  Asp  Phe  His  Arg  Ala  Gly  Leu  Gln  Val  Glu  Phe  Ile  Asn  Pro  Ile
              340                 345                 350

Phe  Glu  Phe  Ser  Arg  Ala  Met  Arg  Arg  Leu  Gly  Leu  Asp  Asp  Ala  Glu
          355                 360                 365

Tyr  Ala  Leu  Leu  Ile  Ala  Ile  Asn  Ile  Phe  Ser  Ala  Asp  Arg  Pro  Asn
370                 375                 380
```

-continued

```
Val Gln Glu Pro Gly Arg Val Glu Ala Leu Gln Gln Pro Tyr Val Glu
385                 390                 395                 400

Ala Leu Leu Ser Tyr Thr Arg Tyr Lys Arg Pro Gln Asp Gln Leu Arg
            405                 410                 415

Phe Pro Arg Met Leu Met Lys Leu Val Ser Leu Arg Thr Leu Ser Ser
                420                 425                 430

Val His Ser Glu Gln Val Phe Ala Leu Arg Leu Gln Asp Lys Lys Leu
            435                 440                 445

Pro Pro Leu Leu Ser Glu Ile Trp Asp Val Asp Glu
450                 455                 460
```

(2) INFORMATION FOR SEQ ID NO:3:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 256..1584

(xi) SEQUENCE DESCRIPTION: SEQ ID NO:3:

```
GGAATTCGGC ACGAGCACGC AAGGCTGTTG CTCCGAGCTA CTCCCAGGCT TCTGAAGTTA      60

CTTCTGAAGT GCTGTGGAGG AGCAATCACC GGTGCGGACA CAGAGCTCCC GCCTCCCACA     120

GCCATTTCCA GGGTAACGAA GTAGGAGACC CCCTCCTGCG ACCCCCTCAC GATCGCCGGT     180

GCAGTCATGA GCCCGCCCTC CCCCTGGTGC ACGGAGAGGG GCGGGGCCTG AACGAGGCT      240

GCTTCGTGAC CCACT ATG TCT TCC CCC ACA AGT TCT CTG GAC ACT CCC TTG      291
                Met Ser Ser Pro Thr Ser Ser Leu Asp Thr Pro Leu
                                465                 470

CCT GGG AAT GGT TCT CCC CAG CCC AGT ACC TCC TCC ACT TCA CCC ACT       339
Pro Gly Asn Gly Ser Pro Gln Pro Ser Thr Ser Ser Thr Ser Pro Thr
            475                 480                 485

ATT AAG GAG GAG GTA CAG GAG ACT GAT CCA CCT CCA GGC TCT GAA GGG       387
Ile Lys Glu Glu Val Gln Glu Thr Asp Pro Pro Pro Gly Ser Glu Gly
    490                 495                 500

TCC AGC TCT GCC TAC ATC GTG GAG CCA GAG GAT GAA CCT GAG CGC AAG       435
Ser Ser Ser Ala Tyr Ile Val Glu Pro Glu Asp Glu Pro Glu Arg Lys
505                 510                 515                 520

CGG AAG AAG GGT CCG GCC CCG AAG ATG CTG GGC CAT GAG CTG TGC CGC       483
Arg Lys Lys Gly Pro Ala Pro Lys Met Leu Gly His Glu Leu Cys Arg
                525                 530                 535

GTG TGC GGG GAC AAG GCC TCG GGC TTC CAC TAC AAT GTG CTC AGT TGT       531
Val Cys Gly Asp Lys Ala Ser Gly Phe His Tyr Asn Val Leu Ser Cys
            540                 545                 550

GAA GGC TGC AAA GGC TTC TTC CGG CGT AGC GTG GTC CAT GGT GGG GCC       579
Glu Gly Cys Lys Gly Phe Phe Arg Arg Ser Val Val His Gly Gly Ala
            555                 560                 565

GGG CGC TAT GCC TGT CGG GGC AGC GGA ACC TGC CAG ATG GAT GCC TTC       627
Gly Arg Tyr Ala Cys Arg Gly Ser Gly Thr Cys Gln Met Asp Ala Phe
    570                 575                 580

ATG CGG CGC AAG TGC CAG CTC TGC AGA CTG CGC AAG TGC AAG GAG GCT       675
Met Arg Arg Lys Cys Gln Leu Cys Arg Leu Arg Lys Cys Lys Glu Ala
585                 590                 595                 600

GGC ATG CGG GAG CAG TGC GTG CTT TCT GAG GAG CAG ATT CGG AAG AAA       723
Gly Met Arg Glu Gln Cys Val Leu Ser Glu Glu Gln Ile Arg Lys Lys
                605                 610                 615
```

| | | | | | | | | | | | | | | | | |
|---|---|---|---|---|---|---|---|---|---|---|---|---|---|---|---|---|
| AAG | ATT | CAG | AAG | CAG | CAA | CAG | CAG | CAG | CCA | CCG | CCC | CCG | ACT | GAG | CCA | 771 |
| Lys | Ile | Gln<br>620 | Lys | Gln | Gln | Gln | Gln | Gln<br>625 | Pro | Pro | Pro | Pro<br>630 | Thr | Glu | Pro | |
| GCA | TCC | GGT | AGC | TCA | GCC | CGG | CCT | GCA | GCC | TCC | CCT | GGC | ACT | TCG | GAA | 819 |
| Ala | Ser | Gly<br>635 | Ser | Ser | Ala | Arg | Pro<br>640 | Ala | Ala | Ser | Pro | Gly<br>645 | Thr | Ser | Glu | |
| GCA | AGT | AGC | CAG | GGC | TCC | GGG | GAA | GGA | GAG | GGC | ATC | CAG | CTG | ACA | GCG | 867 |
| Ala | Ser | Ser<br>650 | Gln | Gly | Ser | Gly<br>655 | Glu | Gly | Glu | Gly<br>660 | Ile | Gln | Leu | Thr | Ala | |
| GCT | CAG | GAG | CTG | ATG | ATC | CAA | CAG | TTA | GTT | GCC | GTG | CAG | CTG | CAG | TGC | 915 |
| Ala<br>665 | Gln | Glu | Leu | Met | Ile<br>670 | Gln | Gln | Leu | Val | Ala<br>675 | Val | Gln | Leu | Gln | Cys<br>680 | |
| AAC | AAG | CGA | TCT | TTC | TCC | GAC | CAG | CCT | AAA | GTC | ACG | CCC | TGG | CCC | TTG | 963 |
| Asn | Lys | Arg | Ser | Phe<br>685 | Ser | Asp | Gln | Pro | Lys<br>690 | Val | Thr | Pro | Trp | Pro<br>695 | Leu | |
| GGT | GCA | GAC | CCT | CAG | TCC | CGA | GAC | GCT | CGT | CAG | CAA | CGC | TTT | GCC | CAC | 1011 |
| Gly | Ala | Asp | Pro<br>700 | Gln | Ser | Arg | Asp | Ala<br>705 | Arg | Gln | Gln | Arg | Phe<br>710 | Ala | His | |
| TTC | ACT | GAG | CTA | GCC | ATC | ATC | TCA | GTC | CAG | GAG | ATC | GTG | GAC | TTC | GCC | 1059 |
| Phe | Thr | Glu<br>715 | Leu | Ala | Ile | Ile | Ser<br>720 | Val | Gln | Glu | Ile | Val<br>725 | Asp | Phe | Ala | |
| AAG | CAG | GTG | CCA | GGG | TTC | CTG | CAG | CTG | GGC | CGG | GAG | GAC | CAG | ATC | GCC | 1107 |
| Lys | Gln | Val<br>730 | Pro | Gly | Phe | Leu<br>735 | Gln | Leu | Gly | Arg<br>740 | Glu | Asp | Gln | Ile | Ala | |
| CTC | CTG | AAG | GCA | TCC | ACC | ATC | GAG | ATC | ATG | TTG | CTA | GAG | ACA | GCC | AGA | 1155 |
| Leu | Leu<br>745 | Lys | Ala | Ser | Thr<br>750 | Ile | Glu | Ile | Met | Leu<br>755 | Leu | Glu | Thr | Ala | Arg<br>760 | |
| CGC | TAC | AAC | CAC | GAG | ACA | GAG | TGC | ATC | ACG | TTC | CTG | AAG | GAC | TTC | ACC | 1203 |
| Arg | Tyr | Asn | His | Glu<br>765 | Thr | Glu | Cys | Ile | Thr<br>770 | Phe | Leu | Lys | Asp | Phe<br>775 | Thr | |
| TAC | AGC | AAG | GAC | GAC | TTC | CAC | CGT | GCA | GGC | TTG | CAG | GTG | GAG | TTC | ATC | 1251 |
| Tyr | Ser | Lys | Asp<br>780 | Asp | Phe | His | Arg | Ala<br>785 | Gly | Leu | Gln | Val | Glu<br>790 | Phe | Ile | |
| AAT | CCC | ATC | TTT | GAG | TTC | TCT | CGG | GCT | ATG | CGT | CGG | CTG | GGC | CTA | GAC | 1299 |
| Asn | Pro | Ile<br>795 | Phe | Glu | Phe | Ser | Arg<br>800 | Ala | Met | Arg | Arg | Leu<br>805 | Gly | Leu | Asp | |
| GAT | GCA | GAG | TAT | GCC | TTG | CTC | ATT | GCC | ATC | AAC | ATC | TTC | TCA | GCG | GAC | 1347 |
| Asp | Ala<br>810 | Glu | Tyr | Ala | Leu | Leu<br>815 | Ile | Ala | Ile | Asn | Ile<br>820 | Phe | Ser | Ala | Asp | |
| CGG | CCT | AAT | GTG | CAG | GAG | CCC | AGC | CGT | GTG | GAG | GCT | CTG | CAG | CAG | CCC | 1395 |
| Arg<br>825 | Pro | Asn | Val | Gln | Glu<br>830 | Pro | Ser | Arg | Val | Glu<br>835 | Ala | Leu | Gln | Gln | Pro<br>840 | |
| TAT | GTG | GAG | GCC | CTC | CTC | TCC | TAC | ACG | AGG | ATC | AAG | CGG | CCG | CAG | GAC | 1443 |
| Tyr | Val | Glu | Ala | Leu<br>845 | Leu | Ser | Tyr | Thr | Arg<br>850 | Ile | Lys | Arg | Pro | Gln<br>855 | Asp | |
| CAG | CTG | CGC | TTC | CCA | CGA | ATG | CTC | ATG | AAG | CTG | GTG | AGC | CTG | CGC | ACC | 1491 |
| Gln | Leu | Arg | Phe<br>860 | Pro | Arg | Met | Leu | Met<br>865 | Lys | Leu | Val | Ser | Leu<br>870 | Arg | Thr | |
| CTC | AGC | TCC | GTG | CAC | TCG | GAG | CAG | GTT | TTC | GCA | TTG | CGT | CTC | CAG | GAC | 1539 |
| Leu | Ser | Ser<br>875 | Val | His | Ser | Glu | Gln<br>880 | Val | Phe | Ala | Leu | Arg<br>885 | Leu | Gln | Asp | |
| AAG | AAG | CTG | CCG | CCT | TTG | CTG | TCC | GAG | ATC | TGG | GAT | GTG | CAT | GAG | | 1584 |
| Lys | Lys | Leu<br>890 | Pro | Pro | Leu | Leu<br>895 | Ser | Glu | Ile | Trp | Asp<br>900 | Val | His | Glu | | |

| | |
|---|---|
| TAGGGGCCGC CACAAGTGCC CCAGCCTTGG TGGTGTCTAC TTGCAGATGG ACGCTTCCTT | 1644 |
| TGCCTTTCCT GGGGTGGGAG GACACTGTCA CAGCCCAGTC CCTGGGCTC GGGCTGAGCG | 1704 |
| AGTGGCAGTT GGCACTAGAA GGTCCCACCC CACCCGCTGA GTCTTCCAGG AGTGGTGAGG | 1764 |
| GTCACAGGCC CTAGCCTCTG ATCTTTACCA GCTGCCCTTC CTCCCGAGCT TACACCTCAG | 1824 |

```
CCTACCACAC CATGCACCTT GAGTGGAGAG AGGTTAGGGC AGGTGGCTCC CCACAGTTGG    1884

GAGACCACAG GCCCCTCTT CTGCCCCTTT TATTTAATAA AAAAAATAAA ATAAAATAAA    1944

GCTCGTGCCG AATTC                                                    1959
```

( 2 ) INFORMATION FOR SEQ ID NO:4:

( i ) SEQUENCE CHARACTERISTICS:
        ( A ) LENGTH: 443 amino acids
        ( B ) TYPE: amino acid
        ( D ) TOPOLOGY: linear ( x i ) SEQUENCE DESCRIPTION: SEQ ID NO:4:

```
Met  Ser  Ser  Pro  Thr  Ser  Ser  Leu  Asp  Thr  Pro  Leu  Pro  Gly  Asn  Gly
 1                   5                        10                        15

Ser  Pro  Gln  Pro  Ser  Thr  Ser  Ser  Thr  Ser  Pro  Thr  Ile  Lys  Glu  Glu
                20                        25                        30

Val  Gln  Glu  Thr  Asp  Pro  Pro  Gly  Ser  Glu  Gly  Ser  Ser  Ser  Ala
           35                        40                        45

Tyr  Ile  Val  Glu  Pro  Glu  Asp  Glu  Pro  Glu  Arg  Lys  Arg  Lys  Lys  Gly
      50                        55                        60

Pro  Ala  Pro  Lys  Met  Leu  Gly  His  Glu  Leu  Cys  Arg  Val  Cys  Gly  Asp
65                        70                        75                        80

Lys  Ala  Ser  Gly  Phe  His  Tyr  Asn  Val  Leu  Ser  Cys  Glu  Gly  Cys  Lys
                     85                        90                        95

Gly  Phe  Phe  Arg  Arg  Ser  Val  Val  His  Gly  Gly  Ala  Gly  Arg  Tyr  Ala
                100                       105                       110

Cys  Arg  Gly  Ser  Gly  Thr  Cys  Gln  Met  Asp  Ala  Phe  Met  Arg  Arg  Lys
           115                       120                       125

Cys  Gln  Leu  Cys  Arg  Leu  Arg  Lys  Cys  Lys  Glu  Ala  Gly  Met  Arg  Glu
     130                       135                       140

Gln  Cys  Val  Leu  Ser  Glu  Glu  Gln  Ile  Arg  Lys  Lys  Lys  Ile  Gln  Lys
145                       150                       155                       160

Gln  Gln  Gln  Gln  Gln  Pro  Pro  Pro  Thr  Glu  Pro  Ala  Ser  Gly  Ser
                     165                       170                       175

Ser  Ala  Arg  Pro  Ala  Ala  Ser  Pro  Gly  Thr  Ser  Glu  Ala  Ser  Ser  Gln
                180                       185                       190

Gly  Ser  Gly  Glu  Gly  Glu  Gly  Ile  Gln  Leu  Thr  Ala  Ala  Gln  Glu  Leu
           195                       200                       205

Met  Ile  Gln  Gln  Leu  Val  Ala  Val  Gln  Leu  Gln  Cys  Asn  Lys  Arg  Ser
     210                       215                       220

Phe  Ser  Asp  Gln  Pro  Lys  Val  Thr  Pro  Trp  Pro  Leu  Gly  Ala  Asp  Pro
225                       230                       235                       240

Gln  Ser  Arg  Asp  Ala  Arg  Gln  Gln  Arg  Phe  Ala  His  Phe  Thr  Glu  Leu
                     245                       250                       255

Ala  Ile  Ile  Ser  Val  Gln  Glu  Ile  Val  Asp  Phe  Ala  Lys  Gln  Val  Pro
                260                       265                       270

Gly  Phe  Leu  Gln  Leu  Gly  Arg  Glu  Asp  Gln  Ile  Ala  Leu  Leu  Lys  Ala
           275                       280                       285

Ser  Thr  Ile  Glu  Ile  Met  Leu  Leu  Glu  Thr  Ala  Arg  Arg  Tyr  Asn  His
     290                       295                       300

Glu  Thr  Glu  Cys  Ile  Thr  Phe  Leu  Lys  Asp  Phe  Thr  Tyr  Ser  Lys  Asp
305                       310                       315                       320

Asp  Phe  His  Arg  Ala  Gly  Leu  Gln  Val  Glu  Phe  Ile  Asn  Pro  Ile  Phe
                     325                       330                       335
```

```
Glu  Phe  Ser  Arg  Ala  Met  Arg  Arg  Leu  Gly  Leu  Asp  Asp  Ala  Glu  Tyr
               340                      345                     350

Ala  Leu  Leu  Ile  Ala  Ile  Asn  Ile  Phe  Ser  Ala  Asp  Arg  Pro  Asn  Val
          355                           360                     365

Gln  Glu  Pro  Ser  Arg  Val  Glu  Ala  Leu  Gln  Gln  Pro  Tyr  Val  Glu  Ala
     370                      375                     380

Leu  Leu  Ser  Tyr  Thr  Arg  Ile  Lys  Arg  Pro  Gln  Asp  Gln  Leu  Arg  Phe
385                      390                      395                          400

Pro  Arg  Met  Leu  Met  Lys  Leu  Val  Ser  Leu  Arg  Thr  Leu  Ser  Ser  Val
               405                      410                          415

His  Ser  Glu  Gln  Val  Phe  Ala  Leu  Arg  Leu  Gln  Asp  Lys  Lys  Leu  Pro
               420                      425                     430

Pro  Leu  Leu  Ser  Glu  Ile  Trp  Asp  Val  His  Glu
          435                      440
```

( 2 ) INFORMATION FOR SEQ ID NO:5:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: N
        ( B ) LOCATION: 7..9
        ( C ) IDENTIFICATION METHOD: N =A, G, C, or T ( x i ) SEQUENCE DESCRIPTION: SEQ ID NO:5:

AGAACANNNT GTTCT                                  15

( 2 ) INFORMATION FOR SEQ ID NO:6:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: N
        ( B ) LOCATION: 7..9
        ( C ) IDENTIFICATION METHOD: N =A, G, C, or T ( x i ) SEQUENCE DESCRIPTION: SEQ ID NO:6:

AGGTCANNNT GACCT                                  15

( 2 ) INFORMATION FOR SEQ ID NO:7:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

TTAAAGAAGA CTTTACAGCT TCCACA                  26

( 2 ) INFORMATION FOR SEQ ID NO:8:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

TTGAAGAATA CCTTGCAGCT CCCACA 26

( 2 ) INFORMATION FOR SEQ ID NO:9:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

TTAAAGAAGA CTTTACAGCT GCCACA 26

( 2 ) INFORMATION FOR SEQ ID NO:10:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i x ) FEATURE:
        ( A ) NAME/KEY: N
        ( B ) LOCATION: 9
        ( C ) IDENTIFICATION METHOD: N =Inosine ( i x ) FEATURE:
        ( A ) NAME/KEY: N
        ( B ) LOCATION: 21
        ( C ) IDENTIFICATION METHOD: N =Inosine ( x i ) SEQUENCE DESCRIPTION: SEQ ID NO:10:

CTAAAGAANC CCTTGCAGCC NTCACAGGT 29

( 2 ) INFORMATION FOR SEQ ID NO:11:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i x ) FEATURE:
        ( A ) NAME/KEY: N
        ( B ) LOCATION: 9
        ( C ) IDENTIFICATION METHOD: N =Inosine ( i x ) FEATURE:
        ( A ) NAME/KEY: N
        ( B ) LOCATION: 21
        ( C ) IDENTIFICATION METHOD: N =Inosine ( x i ) SEQUENCE DESCRIPTION: SEQ ID NO:11:

CTGAAGAANC CCTTGCAGCC NTCACAGGT 29

( 2 ) INFORMATION FOR SEQ ID NO:12:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i x ) FEATURE:
        ( A ) NAME/KEY: N
        ( B ) LOCATION: 27
        ( C ) IDENTIFICATION METHOD: N =Inosine ( x i ) SEQUENCE DESCRIPTION: SEQ ID NO:12:

TTAAAGAATA CTTTGCAGCT TCCACANGT 29

( 2 ) INFORMATION FOR SEQ ID NO:13:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i x ) FEATURE:
        ( A ) NAME/KEY: N
        ( B ) LOCATION: 27
        ( C ) IDENTIFICATION METHOD: N =Inosine ( x i ) SEQUENCE DESCRIPTION: SEQ ID NO:13:

TTAGAGAAGA CCTTGCAGCT GCCACANGT        29

( 2 ) INFORMATION FOR SEQ ID NO:14:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i x ) FEATURE:
        ( A ) NAME/KEY: N
        ( B ) LOCATION: 14
        ( C ) IDENTIFICATION METHOD: N =Inosine ( i x ) FEATURE:
        ( A ) NAME/KEY: N
        ( B ) LOCATION: 23
        ( C ) IDENTIFICATION METHOD: N =Inosine ( x i ) SEQUENCE DESCRIPTION: SEQ ID NO:14:

CCCCGTAGTG ACANCCAGAA GCNTCATC        28

( 2 ) INFORMATION FOR SEQ ID NO:15:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i x ) FEATURE:
        ( A ) NAME/KEY: N
        ( B ) LOCATION: 14
        ( C ) IDENTIFICATION METHOD: N =Inosine ( i x ) FEATURE:
        ( A ) NAME/KEY: N
        ( B ) LOCATION: 23
        ( C ) IDENTIFICATION METHOD: N =Inosine ( x i ) SEQUENCE DESCRIPTION: SEQ ID NO:15:

CTCCATAATG GCANCCTGAG GCNTCATC        28

( 2 ) INFORMATION FOR SEQ ID NO:16:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i x ) FEATURE:
        ( A ) NAME/KEY: N
        ( B ) LOCATION: 5
        ( C ) IDENTIFICATION METHOD: N =Inosine ( i x ) FEATURE:
        ( A ) NAME/KEY: N

```
            ( B ) LOCATION: 11
            ( C ) IDENTIFICATION METHOD: N =Inosine ( i x ) FEATURE:
            ( A ) NAME/KEY: N
            ( B ) LOCATION: 23
            ( C ) IDENTIFICATION METHOD: N =Inosine ( x i ) SEQUENCE DESCRIPTION: SEQ ID NO:16:

AGTGNAAGCC NGTGGCCCGG TCNCCACA                              28

( 2 ) INFORMATION FOR SEQ ID NO:17:

( i ) SEQUENCE CHARACTERISTICS:
            ( A ) LENGTH: 28 base pairs
            ( B ) TYPE: nucleic acid
            ( C ) STRANDEDNESS: single
            ( D ) TOPOLOGY: linear ( i x ) FEATURE:
            ( A ) NAME/KEY: N
            ( B ) LOCATION: 11
            ( C ) IDENTIFICATION METHOD: N =Inosine ( i x ) FEATURE:
            ( A ) NAME/KEY: N
            ( B ) LOCATION: 23
            ( C ) IDENTIFICATION METHOD: N =Inosine ( x i ) SEQUENCE DESCRIPTION: SEQ ID NO:17:

AGTGTTAACC NGTGGCTTGG TCNCCACA                              28

( 2 ) INFORMATION FOR SEQ ID NO:18:

( i ) SEQUENCE CHARACTERISTICS:
            ( A ) LENGTH: 48 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:18:

GCCTGGAACG AGGATCCTGA AGGAACCACC ATGTCTTCCC CCACAAGT        48

( 2 ) INFORMATION FOR SEQ ID NO:19:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:19:

ACAGGCATAG CGCCCGGCCC CACCATGGAC CACCGT                     36

( 2 ) INFORMATION FOR SEQ ID NO:20:

( i ) SEQUENCE CHARACTERISTICS:
            ( A ) LENGTH: 42 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:20:

GAGATCCCCG GGATCCTGA AGGAACCACC ATGTCTTCCC CC               42

( 2 ) INFORMATION FOR SEQ ID NO:21:

( i ) SEQUENCE CHARACTERISTICS:
            ( A ) LENGTH: 15 amino acids
            ( B ) TYPE: amino acid
```

( C ) STRANDEDNESS: single
( D ) TOPOLOGY: linear ( i i ) MOLECULE TYPE: peptide ( x i ) SEQUENCE DESCRIPTION: SEQ ID NO:21:

```
Glu Ala Gly Met Arg Glu Ser Ser Val Leu Ser Glu Glu Gln Ile
1               5                   10                  15
```

( 2 ) INFORMATION FOR SEQ ID NO:22:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:22:

```
Glu Ala Gly Arg Glu Gln Cys Val Leu Ser Glu Glu Gln Ile
1               5                   10
```

( 2 ) INFORMATION FOR SEQ ID NO:23:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

GATCCTCAGG TCAAGGTCAG AAGCT                                                       2 5

( 2 ) INFORMATION FOR SEQ ID NO:24:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

AGCTTCTGAC CTTGACCTGA GGATC                                                       2 5

( 2 ) INFORMATION FOR SEQ ID NO:25:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

GATCCTCAGG TCAGAGGTCA GAAGCT                                                  2 6

( 2 ) INFORMATION FOR SEQ ID NO:26:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

AGCTTCTGAC CTCTGACCTG AGGATC                                                  2 6

( 2 ) INFORMATION FOR SEQ ID NO:27:

( i ) SEQUENCE CHARACTERISTICS:

(A) LENGTH: 27 base pairs
(B) TYPE: nucleic acid
(C) STRANDEDNESS: single
(D) TOPOLOGY: linear (xi) SEQUENCE DESCRIPTION: SEQ ID NO:27:

GATCCTCAGG TCAAGAGGTC AGAAGCT              27

(2) INFORMATION FOR SEQ ID NO:28:

(i) SEQUENCE CHARACTERISTICS:
(A) LENGTH: 27 base pairs
(B) TYPE: nucleic acid
(C) STRANDEDNESS: single
(D) TOPOLOGY: linear (xi) SEQUENCE DESCRIPTION: SEQ ID NO:28:

AGCTTCTGAC CTCTTGACCT GAGGATC              27

(2) INFORMATION FOR SEQ ID NO:29:

(i) SEQUENCE CHARACTERISTICS:
(A) LENGTH: 28 base pairs
(B) TYPE: nucleic acid
(C) STRANDEDNESS: single
(D) TOPOLOGY: linear (xi) SEQUENCE DESCRIPTION: SEQ ID NO:29:

GATCCTCAGG TCAAGGAGGT CAGAAGCT             28

(2) INFORMATION FOR SEQ ID NO:30:

(i) SEQUENCE CHARACTERISTICS:
(A) LENGTH: 28 base pairs
(B) TYPE: nucleic acid
(C) STRANDEDNESS: single
(D) TOPOLOGY: linear (xi) SEQUENCE DESCRIPTION: SEQ ID NO:30:

AGCTTCTGAC CTCCTTGACC TGAGGATC             28

(2) INFORMATION FOR SEQ ID NO:31:

(i) SEQUENCE CHARACTERISTICS:
(A) LENGTH: 28 base pairs
(B) TYPE: nucleic acid
(C) STRANDEDNESS: single
(D) TOPOLOGY: linear (xi) SEQUENCE DESCRIPTION: SEQ ID NO:31:

GATCCTCAGG TCCAGGAGGT CAGAAGCT             28

(2) INFORMATION FOR SEQ ID NO:32:

(i) SEQUENCE CHARACTERISTICS:
(A) LENGTH: 29 base pairs
(B) TYPE: nucleic acid
(C) STRANDEDNESS: single
(D) TOPOLOGY: linear (xi) SEQUENCE DESCRIPTION: SEQ ID NO:32:

AGCTTCTGAC CTCCTGTGAC CTGAGGATC            29

(2) INFORMATION FOR SEQ ID NO:33:

(i) SEQUENCE CHARACTERISTICS:
(A) LENGTH: 30 base pairs
(B) TYPE: nucleic acid ( C ) STRANDEDNESS: single
( D ) TOPOLOGY: linear ( x i ) SEQUENCE DESCRIPTION: SEQ ID NO:33:

GATCCTCAGG TCACCAGGAG GTCAGAAGCT     30

( 2 ) INFORMATION FOR SEQ ID NO:34:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:34:

CGATTCTGAC CTCCTGGTGA CCTGAGGATC     30

( 2 ) INFORMATION FOR SEQ ID NO:35:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:35:

GATCCTCAGG TCACCAAGGA GGTCAGAAGC T     31

( 2 ) INFORMATION FOR SEQ ID NO:36:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:36:

AGCTTCTGAC CTCCTTGGTG ACCTGAGGAT C     31

( 2 ) INFORMATION FOR SEQ ID NO:37:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( x i ) SEQUENCE DESCRIPTION: SEQ ID NO:37:

AGCTTTCAGG TCACAGGAGG TCAGAG     26

( 2 ) INFORMATION FOR SEQ ID NO:38:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( x i ) SEQUENCE DESCRIPTION: SEQ ID NO:38:

AGCTCTCTGA CCTCCTGTGA CCTGAA     26

ISOLATED NUCLEIC ACID ENCODING A UBIQUITOUS NUCLEAR RECEPTOR

The present application is a continuation-in-part of U.S. Ser. No. 08/152,003, filed Nov. 10, 1993, abandoned, the entire text and figures of which disclosures are specifically incorporated herein by reference without disclaimer.

The United States government has certain rights in the present invention pursuant to Grant CA-58073 from the National Cancer Institute, and grants DDK-41670 and DDK37694 from the National Institutes of Health.

BACKGROUND OF THE INVENTION

1. Field of the Invention

The present invention relates to a ubiquitous, nuclear receptor (UR), polynucleotides encoding that receptor, antibodies against that receptor and the use of that receptor in screening assays.

2. Description of the Related Art

Normal growth and differentiation of all organisms is dependent on cells responding correctly to a variety of internal and external signals. Many of these signals produce their effects by ultimately changing the transcription of specific genes. One well-studied group of proteins that mediate a cell's response to a variety of signals is the family of transcription factors known as nuclear receptors. Members of this group include receptors for steroid hormones, vitamin D, ecdysone, cis and trans retinoic acid, thyroid hormone, fatty acids (and other peroxisomal proliferators), as well as so-called orphan receptors, proteins that are structurally similar to other members of this group, but for which no ligands are known. Orphan receptors may be indicative of unknown signaling pathways in the cell or may be nuclear receptors that function without ligand activation. There are indications that the activation of transcription by some of these orphan receptors may occur in the absence of an exogenous ligand and/or through signal transduction pathways originating from the cell surface.

Steroid hormones affect the growth and function of specific cells by binding to intracellular receptors (SR) and forming SR-hormone complexes. SR-hormone complexes then interact with a hormone response element (HRE) in the control region of specific genes and alter specific gene expression. cDNAs for many SRs have been isolated and characterized, making it possible to deduce the amino acid sequences of various steroid/thyroid/retinoic acid receptors and related members of the super family of nuclear receptors (Evans, 1988; Liao et al., 1989; Forman and Samuels, 1990).

Three functional domains have been defined in SRs using a combination of deletion and mutation analysis as well as the construction of chimeric receptors. An amino terminal domain is believed to have some regulatory function. A DNA-binding domain (DBD) has two zinc finger structural elements and recognizes a specific HRE in a responsive gene. Specific amino acid residues in the DNA-binding domain have been shown to confer DNA sequence binding specificity. A hormone-binding-domain (HBD) is at the carboxy-terminal region of the SR. In the absence of hormone, the HBD appears to interfere with the interaction of the DBD with its HRE. Hormone binding seems to result in a conformational change in the SR and relieve this interference. A SR without the HBD constitutively activates transcription but at a low level.

Both the amino-terminal domain and the HBD appear to have transcription activation functions (TAF) that have not been well defined or understood. Acidic residues in the amino-terminal domains of some SRs may be important for these transcription factors to interact with RNA polymerase. TAF activity may be dependent on interactions with other protein factors or nuclear components (Tora et al., 1989; Tasset et al., 1990; Diamond et al., 1990). Certain oncoproteins (e.g., c-Jun and c-Fos) can show synergistic or antagonistic activity with glucocorticoid receptors (GR) in transfected cells. Interaction of the GR with these oncoproteins appears to involve oligo (or di)mer formation through a leucine zipper-like interaction. Receptors for glucocorticoid, estrogen and vitamins A and D have been shown to interact, either physically or functionally, with the Jun and Fos components of AP-1 in the transactivation of steroid- or AP-1 regulated genes (Diamond et al., 1990; Yang-Yen et al., 1990; Owen et al., 1990).

Defects in the expression or mutations in SR genes are responsible for various abnormalities in hormone responses. For example, a defect in the X-chromosome-linked AR has been considered to be responsible for syndromes of androgen resistance, such as testicular feminization (tfm). Mutations in AR genes have been observed in more than 20 individuals with abnormal androgen responses. Mutations in the HBD of AR genes have resulted in changes in one amino acid, introduction of a premature stop codon, deletion of part or all of a domain, or alternative splicing. Such a mutation in AR genes also cause changes in affinities and specificities of the hormone binding and allow mutated AR to utilize other steroid hormones. For this reason, antiandrogens can act as androgens in AR-dependent transactivation of specific genes (Liao et al., 1989; Sai et al., 1990; Kokontis et al., 1991).

Although steroid hormones affect transcription of specific genes, steroid hormones are also known to regulate post-transcriptional processes such as the stabilization or de-stabilization of specific mRNAs. The mechanism by which steroids affect mRNA stability is not known. Intracellular receptor recycling may be involved in steroid hormone mediation of mRNA stabilization and other posttranscriptional effects (Liao et al., 1980; Hiipakka and Liao, 1988).

Some nuclear proteins having a typical three-domain receptor structure but without a known hormonal ligand are called orphan receptors (O'Malley, 1990; Kokontis et al., 1991). Some of these orphan receptors are constitutively active in transactivate target genes without the need to interact with a ligand. It is possible that the functions of some orphan receptors are regulated by binding of natural and/or synthetic compounds to the HBD. These orphan receptors may be useful in finding new hormones or pharmaceutically effective agents.

Based on extensive structure-function studies with receptors for steroid and thyroid hormones, vitamin D and retinoic acids, all nuclear receptors appear to be made up of three separate structural and functional domains (Evans, 1988; Carson-Jurica et al., 1990). The first domain, found in the N-terminal region of the protein, is usually important for gene trans-activation (Godowski et al., 1988; Folkers et al., 1993). This region is poorly conserved in sequence and length among different nuclear receptors and even between the same receptor in different species. How the N-terminal domain participates in gene transactivation is unknown, but interactions with other transcription factors have been proposed.

The second domain is a region adjacent to the N-terminal domain, consists of about 68 amino acids, is rich in basic amino acids, and is responsible for DNA-binding activity (Freedman, 1992). This domain binds two zinc ions, each bound through four sulfur atoms of eight cysteine residues in this domain. The zinc stabilizes secondary structural elements (called zinc fingers or modules) that are important for interaction of the protein with DNA. The sequence of the DNA-binding domain (DBD), although distinct for each receptor type, is highly conserved in all members of this family. In fact, several new nuclear receptors have been discovered, and are part of the present invention. This domain may also participate in the homodimerization of steroid receptors. Specific amino acid residues in the DBD confer DNA sequence-binding specificity (Danielsen et al., 1989; Umesono and Evans, 1989). Nuclear receptors, with the possible exception of the glucocorticoid receptor, appear to reside in the nucleus, even in the absence of ligand. A hinge region connecting the DBD to the C-terminal domain contains a nuclear localization signal. Proteins may interact with this signal sequence to shuttle receptors into nuclei through the nuclear pores. This process appears to be an energy-dependent mechanism for recycling receptors.

The third domain is found in the C-terminus of the protein and is responsible for ligand binding activity. Single amino acid changes (natural or experimentally-induced mutations) in this domain can drastically alter a receptor's binding specificity and ability to modulate gene transcription. This domain also modulates the ability of the receptor to control transcription in the absence of ligand and contains structures important for protein-protein interactions, such as with heat shock proteins and various nuclear receptors. Certain regions of the ligand-binding domain (LBD) are moderately conserved among nuclear receptors, which may reflect conserved function of these elements. In particular, structures called leucine zippers that consist of heptad repeats of leucine and other small hydrophobic amino acids may act as dimerization interfaces for receptor homo- or heterodimerization (Forman and Samuels, 1990). Many of the nuclear receptors have been shown to be phosphoproteins, however, the role of phosphorylation in receptor function remains unclear (Power et al., 1991; Lydon et al., 1992; O'Malley and Conneely, 1992).

Nuclear receptors modulate gene expression in target cells by binding to specific DNA HREs usually located upstream of hormonally-regulated genes (Truss and Beato, 1993). An HRE may be either simple or 'composite', where binding sites of other transcription factors overlap or lie adjacent to the HRE (Diamond et al., 1990; Lucas and Granner, 1992). Three classes of simple HREs have been described. The nuclear receptors for androgens, glucocorticoids, mineralocorticoids, and progestins bind inverted repeats of a 6-bp DNA element (AGAACA) separated by three non-conserved base pairs. The consensus sequence for this binding site is 5'-AGAACANNNTGTTCT-3' or (SEQ ID NO:5). The fact that these four different receptors bind to the same response element is consistent with the observation that amino acids in the DBD of these steroid receptors that are critical for DNA recognition are conserved.

Estrogen receptors also bind to a similar 6-bp inverted repeat (AGGTCA) with the consensus sequence 5'-AGGTCANNNTGACCT-3' (SEQ ID NO:6). The palindromic nature of these binding sites led to the hypothesis that steroid receptors bind to DNA as homodimers. This was confirmed by x-ray crystallography of the glucocorticoid receptor bound to its HRE (Luisi et al., 1991). Many of the nonsteroid nuclear receptors (thyroid hormone, retinoic acids, vitamin D, etc.) bind to inverted repeats identical to the estrogen receptor but with different spacing, or to direct repeats with optimal spacing dependent on the particular nuclear receptor. The repeat nature of these binding sites implies that these receptors may bind as head to head or head to tail dimers. A third group of nuclear receptors typified by NGFI-B (also known as NUR 77 or TR3) appear to bind to DNA as a protein monomer that requires only a single half-site for DNA binding (Wilson et al., 1991; Wilson et al., 1993). The sequence of its binding site, 5'-AAAGGTCA-3', is very similar to the half site of the estrogen receptor HRE.

In contrast to steroid receptors, which bind to DNA as homodimers, some members of the nuclear receptor family bind more effectively to DNA as heterodimers. For example, receptors for thyroid hormone (TR), vitamin D (VDR), all trans-retinoic acid (RAR), and peroxisomal proliferators (PPAR) bind to DNA in vitro more strongly and modulate transcription as heterodimers with the 9-cis-retinoic acid (9c-RA) receptor (RXR) (Yu et al., 1991; Kliewer et al., 1992; Leid et al., 1992). Response element specificity for these receptor dimers is complex, somewhat flexible, and dependent on the dimerization partner. Members of this subfamily can bind to direct repeats of the DNA consensus sequence element AGGTCA with variable spacing with the following generalized specificity: 1 bp spacing for RXR::RXR and RXR:PPAR; 2 bp for COUP:COUP; 3 bp for VDR:RXR; 4 bp for TR:RXR; 5 bp for RAR:RXR; and 6 bp for VDR:VDR (Carlberg et al., 1993). Homodimers of RAR and TR and heterodimers of RXR and TR or RAR also function on palindromic repeats with no spacing (Forman and Samuels, 1990).

Initially, it was proposed that a code based on spacing and orientation of half sites could provide transcriptional selectivity to each of these receptor types that bind to the same half site DNA sequence (Näär et al., 1991; Umesono et al., 1991). However, as more response element-receptor dimer combinations are investigated exceptions to the "rule" are appearing. For example, RAR:RXR dimers activate gene expression using response elements with 1- or 2-bp spacing (Durand et al., 1992) and the COUP-TF homodimer recognizes a number of direct repeats with variable spacing while acting as a repressor of gene transcription (Tran et al., 1992). Interactions between TR and RAR have also been documented and may have a role in controlling specific gene transcription (Forman et al., 1989; Forman et al., 1992). Specificity in transcriptional activation may ultimately be determined by a combination of several factors including the relative binding strength of receptor dimers, their relative affinity for a particular response element, and the relative intracellular concentration of receptors and their ligands. The discovery of new receptors will undoubtedly require modifications to present models of control of gene expression by members of this family.

Although nuclear receptors affect the transcription of specific genes by binding to DNA, some hormones are also known to regulate gene expression by posttranscriptional processes, such as altering the stability of specific mRNAs (Liao et al., 1989). The mechanism by which some hormones affect mRNA stability is unclear. It has been suggested that intracellular receptor recycling (Liao et al., 1989; Mendel et al., 1987; Picard et 1990; Rossini and Liao, 1982; Schmidt and Litwack, 1982) may be involved in steroid hormone mediation of mRNA stabilization and other post-transcriptional effects of steroids (Liao et al., 1973; Liao et al., 1980; Liao et al., 1972). Steroid receptor binding of RNA has been described by many investigators (Ali and Vedeckis, 1987; Rowley et al., 1986; Webb and Litwack, 1986). This hypothesis is consistent with the mechanism proposed later for the action of transcriptional factor IIIA (a protein with several zinc fingers) that regulates both the synthesis and stability of 5S RNA (Miller et al., 1985).

Orphan receptors are those member of the nuclear receptor family that do not have a known ligand. Some of these orphan receptors were cloned by taking advantage of the amino acid conservation in the DNA-binding domain of nuclear receptors, and screening cDNA libraries with a hybridization probe derived from this domain. Using this method, orphan receptor cDNAs have been isolated from human testis and prostate cDNA libraries. These orphan receptors were named testis receptor 2 (TR2) (with several isoforms) and TR3. TR3 is the human counterpart of mouse NUR77/N10 (Lau and Nathans, 1987) and rat NGFI-B, which are early response genes induced by nerve or serum growth factors, (Herschman, 1991; Nakai et al., 1990). The brain-specific transcription factor NURR1 is distinct from but related to NUR77 (Law et al., 1992). The estrogen receptor-related receptors, hERR1 and hERR2 were cloned by low stringency hybridization to cDNA libraries with a DNA probe coding for the DBD of the estrogen receptor (Giguére et al., 1988).

Related or different approaches have led to the discovery of other nuclear receptors including multiple isoforms of retinoic acid receptors (Zelent et al., 1989) and thyroid hormone receptors (Lazar, 1993), the peroxisomal proliferator activator receptor (PPAR), and chicken ovalbumin upstream promoter-transcription factor (COUP-TFI, EAR-3), and apolipoprotein AI regulatory protein (ARP-1, COUP-TFII) (Wang et al., 1989). Hepatocyte nuclear factor 4 (HNF-4) is a kidney, liver and intestinal transcription factor that binds to genes for several proteins synthesized in the liver (Sladek, 1990). GF-1/Eryf-1/NF-E1 is a human erythroid transcription factor that binds to many genes expressed in erythroid cells (Honda et al., 1993). SF-1/ELP/Ad4BP are orphan receptors involved in gene expression of various steroid metabolizing enzymes (Lynch et al., 1993). There are indications that the activation of transcription by some of these orphan receptors may occur in the absence of an exogenous ligand (Davis et al., 1991; Kokontis et al., 1991) and/or through signal transduction pathways originating from the cell surface (O'Malley and Conneely, 1992).

The evolutionary relationship of nuclear receptors and other transcription factors is not clear. Given the separate functional and structural domains in the family of nuclear receptors, one possibility is that different domains have independent origins. Another model suggests that nuclear receptors diverged from a single common ancestor (Amero et al., 1992). The precursor probably had multiple domains that initially mediated a simple, signal transduction mechanism, but subsequently acquired increasing complex functions. A phylogenetic tree built from the DNA-binding domain of about three dozen nuclear receptors shows a common precursor of all known nuclear receptors and suggests that these nuclear receptors do not share a common ancestor with other transcription factors, zinc finger proteins, or ligand-binding proteins (Laudet et al., 1992).

BRIEF SUMMARY OF THE INVENTION

The present invention relates generally to the discovery of a new member of the nuclear receptor family of transcription factors, which has been named Ubiquitous Receptor (UR), because of the many tissues in which it is expressed. UR is distinct from all known nuclear receptors and is not an isoform of known receptors. UR was detected predominantly in nuclei of embryonic and adult organs by immunocytochemical staining. UR interacts with the response elements and network of receptors in the thyroid hormone/retinoic acid receptor subfamily and forms heterodimers with RXR and stimulated reporter gene expression in the absence of 9c-RA, the ligand for RXR.

In one aspect, the present invention provides an isolated and purified UR polypeptide. Preferably, the receptor polypeptide is a recombinant polypeptide, and more preferably comprises the amino acid sequence of FIG. 1A (huR) (SEQ ID NO:1) or FIG. 1B (rUR) (SEQ ID NO:2).

In another aspect, the present invention provides an isolated and purified polynucleotide that encodes a UR polypeptide. Preferably, the polynucleotide is a DNA molecule. More preferably, an isolated and purified polynucleotide comprising the nucleotide base sequence of FIG. 1C (SEQ ID NO:3) or FIG. 1D (SEQ ID NO:4).

The present invention also contemplates an expression vector comprising a polynucleotide that encodes a URpolypeptide. In a preferred embodiment, the polynucleotide is operatively linked to an enhancer-promoter.

Also contemplated is a recombinant cell transfected with a polynucleotide that encodes a UR polypeptide. Preferably, the polynucleotide is under the transcriptional control of regulatory signals functional in the recombinant cell, and the regulatory signals appropriately control expression of the receptor polypeptide in a manner to enable all necessary transcriptional and post-transcriptional modification.

In yet another aspect, the present invention contemplates a process of preparing a UR polypeptide, by producing a transformed recombinant cell, and maintaining the transformed recombinant cell under biological conditions suitable for the expression of the polypeptide.

The present invention also contemplates an antibody immunoreactive with a UR polypeptide. The antibody may be either monoclonal or polyclonal. Preferably, the antibody is a monoclonal antibody produced by recovering the polypeptide from a cell host, expressing the polypeptides and then preparing antibody to the polypeptide in a suitable animal host.

In still another aspect, the present invention provides a process of detecting a UR polypeptide, which process comprises immunoreacting the polypeptide with an antibody of the present invention and a diagnostic assay kit for detecting the presence of a UR polypeptide in a biological sample, the kit comprising a first container means comprising a first antibody that immunoreacts with the UR polypeptide. The first antibody is present in an amount sufficient to perform at least one assay.

Still further, the present invention provides a process of detecting a DNA molecule or RNA transcript that encodes a UR polypeptide by hybridizing the DNA or RNA transcript with a polynucleotide that encodes the receptor polypeptide to form a duplex, and then detecting the duplex.

Still further, the present invention provides a process of screening a substance for its ability to interact witbUR itself.

Nucleic Acid Embodiments

In one aspect, the present invention provides an isolated and purified polynucleotide that encodes a UR polypeptide. In a preferred embodiment, a polynucleotide of the present invention is a DNA molecule. Even more preferably, a polynucleotide of the present invention encodes a polypeptide comprising the amino acid residue sequence of rUR or hUR (FIG. 1A and FIG. 1B). Most preferably, an isolated and purified polynucleotide of the invention comprises the nucleotide base sequence of FIG. 1C and FIG. 1D.

As used herein, the term "polynucleotide" means a sequence of nucleotides connected by phosphodiester linkages. Polynucleotides are presented herein in a 5' to 3' direction. A polynucleotide of the present invention may comprise about several hundred thousand base pairs. Preferably, a polynucleotide comprises from about 100 to about 100,000 base pairs. Preferred lengths of particular polynucleotides are set forth hereinafter.

A polynucleotide of the present invention may be a deoxyribonucleic acid (DNA) molecule or ribonucleic acid (RNA) molecule. Where a polynucleotide is a DNA molecule, that molecule may be a gene or a cDNA molecule. Nucleotide bases are indicated herein by a single letter code: adenine (A), guanine (G), thymine (T), cytosine (C), inosine (I) and uracil (U).

A polynucleotide of the present invention may be prepared using standard techniques well-known to one of skill in the art. The preparation of a cDNA molecule encoding a UR polypeptide of the present invention is described hereinafter in the examples. A polynucleotide may also be prepared from genomic DNA libraries using lambda phage technologies (see Example 17 for detailed protocols).

In another aspect, the present invention provides an isolated and purified polynucleotide that encodes a UR polypeptide, where the polynucleotide is preparable by a process comprising the steps of constructing a library of cDNA clones from a cell that expresses the polypeptide; screening the library with a labelled cDNA probe prepared from RNA that encodes the polypeptide; and selecting a clone that hybridizes to the probe. Preferably, a polynucleotide of the invention is prepared by the above process.

Probes and Primers

In another aspect, DNA sequence information provided by the present invention allows for the preparation of relatively short DNA (or RNA) sequences having the ability to specifically hybridize to gene sequences of the selected polynucleotide disclosed herein. In these aspects, nucleic acid probes of an appropriate length are prepared based on a consideration of a selected nucleotide sequence, e.g., a sequence such as that shown in FIG. 1C or FIG. 1D. The ability of such nucleic acid probes to specifically hybridize to a polynucleotide encoding a UR lends them particular utility in a variety of embodiments. Most importantly, the probes may be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a gene or polynucleotide that encodes a UR polypeptide from mammalian cells using PCR™ technology.

To provide certain of the advantages in accordance with the present invention, a preferred nucleic acid sequence employed for hybridization studies or assays includes probe molecules that are complementary to at least an about 14 to an about 70-nucleotide long stretch of a pollnucleotide that encodes a UR polypeptide, such as the nucleotide base sequences shown in FIG. 1C or FIG. 1D. A size of at least 14 nucleotides in length helps to ensure that the fragment is of sufficient length to form a duplex molecule that is both stable and selective. Molecules having complementary sequences over stretches greater than 14 bases in length are generally preferred, though, in order to increase stability and selectivity of the hybrid, and thereby improve the quality and degree of specific hybrid molecules obtained, one will generally prefer to design nucleic acid molecules having gene-complementary stretches of 25 to 40 nucleotides, 55 to 70 nucleotides, or even longer where desired. Such fragments may be readily prepared by, for example, directly synthesizing the fragment by chemical means, by application of nucleic acid reproduction technology, such as the PCR™ technology of U.S. Pat. No. 4,603,102, herein incorporated by reference, or by excising selected DNA fragments from recombinant plasmids containing appropriate inserts and suitable restriction enzyme sites.

In another aspect, the present invention contemplates an isolated and purified polynucleotide comprising a base sequence that is identical or complementary to a segment of at least 14 contiguous bases of FIG. 1C or FIG. 1D, wherein the polynucleotide hybridizes to a polynucleotide that encodes a UR polypeptide. Preferably, the isolated and purified polynucleotide comprises a base sequence that is identical or complementary to a segment of at least 25 to 70 contiguous bases of FIG. 1C or FIG. 1D. For example, the polynucleotide of the invention may comprise a segment of bases identical or complementary to 40 or 55 contiguous bases of the disclosed nucleotide sequences.

Accordingly, a polynucleotide probe molecule of the invention may be used for its ability to selectively form duplex molecules with complementary stretches of the gene. Depending on the application envisioned, one employs varying conditions of hybridization to achieve varying degree of selectivity of the probe toward the target sequence. For applications requiring a high degree of selectivity, one typically employs relatively stringent conditions to form the hybrids. For example, one selects relatively low salt and/or high temperature conditions, such as provided by about 0.02M to about 0.15M NaCl at temperatures of about 50° C. to about 70° C. Those conditions are particularly selective, and tolerate little, if any, mismatch between the probe and the template or target strand.

Of course, for some applications where one desires to prepare mutants employing a mutant primer strand hybridized to an underlying template or where one seeks to isolate a UR polypeptide coding sequence from other cells, functional equivalents, or the like, less stringent hybridization conditions are typically needed to allow formation of the heteroduplex. In these circumstances, one employs conditions such as about 0.15M to about 0.9M salt, at temperatures ranging from about 20° C. to about 55° C. Cross-hybridizing species may thereby be readily identified as positively hybridizing signals with respect to control hybridizations. In any case, it is generally appreciated that conditions may be rendered more stringent by the addition of increasing amounts of formamide, which serves to destabilize the hybrid duplex in the same manner as increased temperature. Thus, hybridization conditions may be readily manipulated, and thus will generally be a method of choice depending on the desired results.

In still another embodiment of the present invention, there is provided an isolated and purified polynucleotide comprising a base sequence that is identical or complementary to a segment of at least about 14 contiguous bases of rUR. The polynucleotide of the invention hybridizes to rUR, or a complement of rUR. Preferably, the isolated and purified polynucleotide comprises a base sequence that is identical or complementary to a segment of at least 25 to 70 contiguous bases of rUR. For example, the polynucleotide of the invention may comprise a segment of bases identical or complementary to 40 or 55 contiguous bases of rUR.

Alternatively, the present invention contemplates an isolated and purified polynucleotide that comprises a base sequence that is identical or complementary to a segment of at least about 14 contiguous bases of hUR. The polynucleotide of the invention hybridizes to hUR, or a complement of hUR. Preferably, the polynucleotide comprises a base sequence that is identical or complementary to a segment of at least 25 to 70 contiguous bases of hUR. For example, the polynucleotide may comprise a segment of bases identical or complementary to 40 or 55 contiguous bases of hUR.

In certain embodiments, it is advantageous to employ a polynucleotide of the present invention in combination with an appropriate label for detecting hybrid formation. A wide variety of appropriate labels are known in the art, including radioactive, enzymatic or other ligands, such as avidin/biotin, which are capable of giving a detectable signal.

In general, it is envisioned that a hybridization probe described herein is useful both as a reagent in solution hybridization as well as in embodiments employing a solid phase. In embodiments involving a solid phase, the test DNA (or RNA) is adsorbed or otherwise affixed to a selected matrix or surface. This fixed nucleic acid is then subjected to specific hybridization with selected probes under desired conditions. The selected conditions will depend on the particular circumstances and criteria required (e.g., the G+C content, type of target nucleic acid, source of nucleic acid, size of hybridization probe, etc.). Following washing of the matrix to remove nonspecifically bound probe molecules, specific hybridization is detected, or even quantified, by means of the label.

Ubiquitous Nuclear Receptor

In one embodiment, the present invention contemplates an isolated and purified UR polypeptide. Preferably, a UR polypeptide of the invention is a recombinant UR polypeptide. Even more preferably, a UR polypeptide of the present invention comprises an amino acid sequence of FIG. 1A or FIG. 1B (hUR and rUR, respectively). A UR polypeptide preferably comprises less than about 600 amino acid residues and, more preferably less than about 500 amino acid residues.

Polypeptides are disclosed herein as amino acid residue sequences. Those sequences are written left to right in the direction from the amino to the carboxy terminus. In accordance with standard nomenclature, amino acid residue sequences are denominated by either a single letter or a three letter code as indicated below (Table 1).

Modifications and changes may be made in the structure of a polypeptide of the present invention and still obtain a molecule having UR-like characteristics. For example, certain amino acids may be substituted for other amino acids in a sequence without appreciable loss of receptor activity. Because it is the interactive capacity and nature of a polypeptide that defines that polypeptide's biological functional activity, certain amino acid sequence substitutions may be made in a polypeptide sequence (or, of course, its underlying DNA coding sequence) and nevertheless obtain a polypeptide with like properties.

TABLE 1

| Amino Acid Residue | 3-Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |

TABLE 1-continued

| Amino Acid Residue | 3-Letter Code | 1-Letter Code |
|---|---|---|
| Tyrosine | Tyr | Y |
| Valine | Val | V |

In making such changes, the hydropathic index of amino acids may be considered. The importance of the hydropathic amino acid index in conferring interactive biologic function on a polypeptide is generally understood in the art (Kyte and Doolittle, 1982). It is known that certain amino acids may be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid may be substituted by another amino acid having a similar hydropathic index and still obtain a functionally equivalent polypeptide. In such changes, the substitution of amino acids whose hydropathic indices are within ±2 is preferred, those which are within ±1 are particularly preferred, and those within ±0.5 are even more particularly preferred.

Substitution of like amino acids may also be made on the basis of hydrophilicity, particularly where the biological functional equivalent polypeptide or peptide thereby created is intended for use in immunological embodiments. U.S. Pat. No. 4,554,101, incorporated herein by reference, states that the greatest local average hydrophilicity of a polypeptide, as governed by the hydrophilicity of its adjacent amino acids, correlates with its immunogenicity and antigenicity, i.e., with a biological property of the polypeptide.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid may be substituted for another having a similar hydrophilicity value and still obtain a biologically equivalent, and in particular, an immunologically equivalent polypeptide. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate;

serine and threonine; glutamine and asparagine; and valine, leucine and isoleucine (See Table 2, below). The present invention thus contemplates functional or biological equivalents of a UR polypeptide as set forth above.

Biological or functional equivalents of a polypeptide may also be prepared using site-specific mutagenesis. Site-specific mutagenesis is a technique useful in the preparation of second generation polypeptides, or biologically functional equivalent polypeptides or peptides, derived from the sequences thereof, through specific mutagenesis of the underlying DNA. As noted above, such changes may be desirable where amino acid substitutions are desirable. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 14 to 25 nucleotides in length is preferred, with about 5 to 10 residues on both sides of the junction of the sequence being altered.

TABLE 2

| Original Residue | Exemplary Substitutions |
| --- | --- |
| Ala | Gly; Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Met; Leu; Tyr |
| Ser | Thr |
| Thr | Ser |
| Trp | Tyr |
| Tyr | Trp; Phe |
| Val | Ile; Leu |

The technique of site-specific mutagenesis is generally well-known in the art (Adelman et al., 1983). As will be appreciated, the technique typically employs a phage vector which may exist in both a single stranded and double stranded form. Typical vectors useful in site-directed mutagenesis include vectors such as the M13 phage (Messing et al., 1981). These phage are commercially available and their use is generally known to those of skill in the art.

In general, site-directed mutagenesis in accordance herewith is performed by first obtaining a single-stranded vector which includes within its sequence a DNA sequence which encodes all or a portion of the UR polypeptide sequence selected. An oligonucleotide primer bearing the desired mutated sequence is prepared, generally synthetically, for example, by the method of Crea, et al., (1978). This primer is then annealed to the singled-stranded vector, and extended by the use of enzymes such as the Klenow fragment of E. coli polymerase I, to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as E. coli cells and clones are selected which include recombinant vectors bearing the mutation. Commercially available kits come with all the reagents necessary, except the oligonucleotide primers.

A UR polypeptide of the present invention is not limited to a particular source. As disclosed herein, the techniques and compositions of the present invention provide, for example, the identification and isolation of human and rodent sources. Thus, the invention provides for the general detection and isolation of the genus of UR polypeptides from a variety of sources while identifying specifically two species of that genus. It is believed that a number of species of the family of UR polypeptides are amenable to detection and isolation using the compositions and methods of the present inventions.

A polypeptide of the present invention is prepared by standard techniques well known to those skilled in the art. Such techniques include, but are not limited to, isolation and purification from tissues known to contain that polypeptide, and expression from cloned DNA that encodes such a polypeptide using transformed cells.

Expression Vectors

In an alternate embodiment, the present invention provides expression vectors comprising a polynucleotide that encodes a UR polypeptide. Preferably, an expression vector of the present invention comprises a polynucleotide that encodes a polypeptide comprising an amino acid residue sequence of FIG. 1A or FIG. 1B. More preferably, an expression vector of the present invention comprises a polynucleotide comprising a nucleotide base sequence of FIG. 1A or FIG. 1B. Even more preferably, an expression vector of the invention comprises a polynucleotide operatively linked to an enhancer-promoter. More preferably still, an expression vector of the invention comprises a polynucleotide operatively linked to a prokaryotic promoter. Alternatively, an expression vector of the present invention comprises a polynucleotide operatively linked to an enhancer-promoter that is a eukaryotic promoter, and the expression vector further comprises a polyadenylation signal that is positioned 3' of the carboxy-terminal amino acid and within a transcriptional unit of the encoded polypeptide.

A promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer may function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer may be located downstream from the initiation site and may be at a considerable distance from that site.

An enhancer-promoter used in a vector construct of the present invention may be any enhancer-promoter that drives expression in a cell to be transfected. By employing an enhancer-promoter with well-known properties, the level and pattern of gene product expression may be optimized.

A coding sequence of an expression vector is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (RNA). Transcription-terminating regions are well-known in the art. A preferred transcription-terminating region used in an adenovirus vector construct of the present invention comprises a polyadenylation signal of SV40 or the protamine gene.

An expression vector comprises a polynucleotide that encodes a UR polypeptide. Such a polynucleotide is meant to include a sequence of nucleotide bases encoding a UR polypeptide sufficient in length to distinguish said segment from a polynucleotide segment encoding a non-UR polypeptide. A polypeptide of the invention may also encode biologically functional polypeptides or peptides which have variant amino acid sequences, such as with changes selected based on considerations such as the relative hydropathic score of the amino acids being exchanged. These variant sequences are those isolated from natural sources or induced in the sequences disclosed herein using a mutagenic procedure such as site-directed mutagenesis.

An expression vector of the present invention comprises a polynucleotide that encodes a polypeptide comprising an amino acid residue sequence of FIG. 1A or FIG. 1B. An expression vector may include a UR polypeptide-coding region itself or any of the UR polypeptides noted above or it may contain coding regions bearing selected alterations or modifications in the basic coding region of such a UR polypeptide. Alternatively, such vectors or fragments may code larger polypeptides or polypeptides which nevertheless include the basic coding region. In any event, it should be appreciated that due to codon redundancy as well as biological functional equivalence, this aspect of the invention is not limited to the particular DNA molecules corresponding to the polypeptide sequences noted above.

Exemplary vectors include the mammalian expression vectors of the pCMV family including pCMV6b and pCMV6c (Chiron Corp., Emeryville, Calif.). In certain cases, and specifically in the case of these individual mammalian expression vectors, the resulting constructs may require co-transfection with a vector containing a selectable marker such as pSV2neo. Via co-transfection into a dihydrofolate reductase-deficient Chinese hamster ovary cell line, such as DG44, clones expressing opioid polypeptides by virtue of DNA incorporated into such expression vectors may be detected.

A DNA molecule of the present invention may be incorporated into a vector using standard techniques well known in the art. For instance, the vector pUC18 has been demonstrated to be of particular value. Likewise, the related vectors M13mp18 and M13mp19 may be used in certain embodiments of the invention, in particular, in performing dideoxy sequencing.

An expression vector of the present invention is useful both as a means for preparing quantities of the UR polypeptide-encoding DNA itself, and as a means for preparing the encoded polypeptide and peptides. It is contemplated that where UR polypeptides of the invention are made by recombinant means, one may employ either prokaryotic or eukaryotic expression vectors as shuttle systems. However, in that prokaryotic systems are usually incapable of correctly processing precursor polypeptides and, in particular, such systems are incapable of correctly processing membrane associated eukaryotic polypeptides, and since eukaryotic UR polypeptides are anticipated using the teaching of the disclosed invention, one likely expresses such sequences in eukaryotic hosts. However, even where the DNA segment encodes a eukaryotic UR polypeptide, it is contemplated that prokaryotic expression may have some additional applicability. Therefore, the invention may be used in combination with vectors which may shuttle between the eukaryotic and prokaryotic cells. Such a system is described herein which allows the use of bacterial host cells as well as eukaryotic host cells.

Where expression of recombinant UR polypeptides is desired and a eukaryotic host is contemplated, it is most desirable to employ a vector such as a plasmid, that incorporates a eukaryotic origin of replication. Additionally, for the purposes of expression in eukaryotic systems, one desires to position the UR encoding sequence adjacent to and under the control of an effective eukaryotic promoter such as promoters used in combination with Chinese hamster ovary cells. To bring a coding sequence under control of a promoter, whether it is eukaryotic or prokaryotic, what is generally needed is to position the 5' end of the translation initiation side of the proper translational reading frame of the polypeptide between about 1 and about 50 nucleotides 3' of or downstream with respect to the promoter chosen. Furthermore, where eukaryotic expression is anticipated, one would typically desire to incorporate into the transcriptional unit which includes the UR polypeptide, an appropriate polyadenylation side.

The pCMV plasmids are a series of mammalian expression vectors of particular utility in the present invention. The vectors are designed for use in essentially all cultured cells and work extremely well in SV40-transformed simian COS cell lines. The pCMV1, pCMV2, pCMV3, and pCMV5 vectors differ from each other in certain unique restriction sites in the polylinker region of each plasmid. pCMV4 differs from the other four plasmids in containing a translation enhancer in the sequence prior to the polylinker. While they are not directly derived from the pCMV1-pCMV5 series of vectors, the functionally similar pCMV6b and pCMV6c vectors are commercially available (Chiron Corp., Emeryville, Calif.) and are identical except for the orientation of the polylinker region which is reversed in one relative to the other.

The universal components of the pCMV vectors are as follows: The vector backbone is pTZ18R (Pharmacia, Piscataway, N.J.), and contains a bacteriophage f1 origin of replication for production of single stranded DNA and an ampicillin (amp)-resistance gene. The CMV region consists of nucleotides −760 to +3 of the powerful promotor-regulatory region of the human cytomegalovirus (Towne stain) major immediate early gene (Thomsen et al., 1984; Boshart et al., 1985). The human growth hormone fragment (hGH) contains transcription termination and poly-adenylation signals representing sequences 1533 to 2157 of this gene (Seeburg, 1982). There is an Alu middle repetitive DNA sequence in this fragment. Finally, the SV40 origin of replication and early region promoter-enhancer derived from the pcD-X plasmid (HindIII to PstI fragment) described in (Okayama et al., 1983). The promoter in this fragment is oriented such that transcription proceeds away from the CMV/hGH expression cassette.

The pCMV plasmids are distinguishable from each other by differences in the polylinker region and by the presence or absence of the translation enhancer. The starting pCMV1 plasmid has been progressively modified to render an increasing number of unique restriction sites in the polylinker region. To create pCMV2, one of two EcoRI sites in pCMV1 were destroyed. To create pCMV3, pCMV1 was modified by deleting a short segment from the SV40 region (StuI to EcoRI), and in so doing made unique the PstI, SalI, and BamHI sites in the polylinker. To create pCMV4, a synthetic fragment of DNA corresponding to the 5'- untranslated region of a mRNA transcribed from the CMV promoter was added C'. The sequence acts as a translational enhancer by decreasing the requirements for initiation factors in polypeptide synthesis (Jobling et al., 1987; Browning et al., 1988). To create pCMV5, a segment of DNA (HpaI to EcoRI) was deleted from the SV40 origin region of pCMV1 to render unique all sites in the starting polylinker.

The pCMV vectors have been successfully expressed in simian COS cells, mouse L cells, CHO cells, and HeLa cells. In several side by side comparisons they have yielded 5- to 10-fold higher expression levels in COS cells than SV40-based vectors. The pCMV vectors have been used to express the LDL receptor, nuclear factor 1, $G_s$ α polypeptide, polypeptide phosphatase, synaptophysin, synapsin, insulin receptor, influenza hemagglutinin, androgen receptor, sterol 26-hydroxylase, steroid 17- and 21-hydroxylase, cytochrome P-450 oxidoreductase, β-adrenergic receptor, folate receptor, cholesterol side chain cleavage enzyme, and a host of other cDNAs. It should be noted that the SV40 promoter in these plasmids may be used to express other genes such as dominant selectable markers. Finally, there is an ATG sequence in the polylinker between the HindIII and PstI sites in pCMU that may cause spurious translation initiation. This codon should be avoided if possible in expression plasmids. A paper describing the construction and use of the parenteral pCMV1 and pCMV4 vectors has been published (Anderson et al., 1989b).

Transfected Cells

In yet another embodiment, the present invention provides recombinant host cells transformed or transfected with a polynucleotide that encodes an UR polypeptide, as well as transgenic cells derived from those transformed or transfected cells. Preferably, a recombinant host cell of the present invention is transfected with a polynucleotide of FIG. 1C or FIG. 1D. Means of transforming or transfecting cells with exogenous polynucleotide such as DNA molecules are well known in the art and include techniques such as calcium-phosphate- or DEAE-dextran-mediated transfection, protoplast fusion, electroporation, liposome mediated transfection, direct microinjection and adenovirus infection (Sambrook et al., 1989).

The most widely used method is transfection mediated by either calcium phosphate or DEAE-dextran. Although the mechanism remains obscure, it is believed that the transfected DNA enters the cytoplasm of the cell by endocytosis and is transported to the nucleus. Depending on the cell type, up to 90% of a population of cultured cells may be transfected at any one time. Because of its high efficiency, transfection mediated by calcium phosphate or DEAE-dextran is the method of choice for studies requiring transient expression of the foreign DNA in large numbers of cells. Calcium phosphate-mediated transfection is also used to establish cell lines that integrate copies of the foreign DNA, which are usually arranged in head-to-tail tandem arrays into the host cell genome.

In the protoplast fusion method, protoplasts derived from bacteria carrying high numbers of copies of a plasmid of interest are mixed directly with cultured mammalian cells. After fusion of the cell membranes (usually with polyethylene glycol), the contents of the bacterium are delivered into the cytoplasm of the mammalian cells and the plasmid DNA is transported to the nucleus. Protoplast fusion is not as efficient as transfection for many of the cell lines that are commonly used for transient expression assays, but it is useful for cell lines in which endocytosis of DNA occurs inefficiently. Protoplast fusion frequently yields multiple copies of the plasmid DNA tandomly integrated into the host chromosome.

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation may be extremely efficient and may be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Liposome transfection involves encapsulation of DNA and RNA within liposomes, followed by fusion of the liposomes with the cell membrane. The mechanism of how DNA is delivered into the cell is unclear but transfection efficiencies may be as high as 90%.

Direct microinjection of a DNA molecule into nuclei has the advantage of not exposing DNA to cellular compartments such as low-pH endosomes. Microinjection is therefore used primarily as a method to establish lines of cells that carry integrated copies of the DNA of interest.

The use of adenovirus as a vector for cell transfection is well known in the art. Adenovirus vector-mediated cell transfection has been reported for various cells (Stratford-Perricaudet et al., 1992).

A transfected cell may be prokaryotic or eukaryotic. Preferably, the host cells of the invention are eukaryotic host cells. More preferably, the recombinant host cells of the invention are COS-1 cells. Where it is of interest to produce a human UR polypeptides, cultured mammalian or human cells are of particular interest.

In another aspect, the recombinant host cells of the present invention are prokaryotic host cells. Preferably, the recombinant host cells of the invention are bacterial cells of the DH5α™ (GelBCa BRL, Gaithersburg, Md.) strain of *E. coli*. In general, prokaryotes are preferred for the initial cloning of DNA sequences and constructing the vectors useful in the invention. For example, *E. coli* K12 strains may be particularly useful. Other microbial strains which may be used include *E. coli* B, and *E. coli* X1776 (ATCC No. 31537). These examples are, of course, intended to be illustrative rather than limiting.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* may be transformed using pBR322, a plasmid derived from an *E. coli* species (Bolivar et al., 1977). pBR322 contains genes for amp and tetracycline resistance and thus provides easy means for identifying transformed cells. The pBR322 or other microbial plasmid or phage must also contain, or be modified to contain, promoters which may be used by the microbial organism for expression of its own polypeptides.

Those promoters most commonly used in recombinant DNA construction include the β-lactamase (penicillinase) and β-galactosidase (β-Gal) promoter systems (Chang et al., 1978; Itakura et al., 1977; Goeddel et al., 1979; Goeddel et al., 1980) and a tryptophan (TRP) promoter system (EPO Appl. Publ. No. 0036776; Siebwenlist et al., 1980). While these are the most commonly used, other microbial promoters have been discovered and utilized, and details concerning their nucleotide sequences have been published, enabling a skilled worker to introduce promoters functional into plasmid vectors (Siebwenlist et al., 1980).

In addition to prokaryotes, eukaryotic microbes, such as yeast may also be used. *Saccharomyces cerevisiae* or common baker's yeast is the most commonly used among eukaryotic microorganisms, although a number of other strains are commonly available. For expression in Saccharomyces, the plasmid YRp7, for example, is commonly used (Stinchcomb et al., 1979; Kingsman et al., 1979; Tschemper et al., 1980). This plasmid already contains the trpL gene which provides a selection marker for a mutant strain of yeast lacking the ability to grow in tryptophan, for example ATCC No. 44076 or PEP4-1 (Jones, 1977). The presence of the trpL lesion as a characteristic of the yeast host cell genome then provides an effective environment for detecting transformation by growth in the absence of tryptophan.

Suitable promotor sequences in yeast vectors include the promoters for 3-phosphoglycerate kinase (Hitzeman et al., 1980) or other glycolytic enzymes (Hess et al., 1968; Holland et al., 1978) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also introduced into the expression vector downstream from the sequences to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin or replication and termination sequences is suitable.

In addition to microorganisms, cultures of cells derived from multicellular organisms may also be used as hosts. In principle, any such cell culture may be employed, whether from vertebrate or invertebrate culture. However, interest has been greatest in vertebrate cells, and propagation of vertebrate cells in tissue culture has become a routine procedure in recent years (Kruse and Peterson, 1973). Examples of such useful host cell lines are AtT-20, VERO and HeLa cells, Chinese hamster ovary (CHO) cell lines, and W138, BHK, COSM6, COS-7, 293 and MDCK cell lines. Expression vectors for such cells ordinarily include (if necessary) an origin of replication, a promoter located upstream of the gene to be expressed, along with any necessary ribosome binding sites, RNA splice sites, polyadenylation site, and transcriptional terminator sequences.

For use in mammalian cells, the control functions on the expression vectors are often derived from viral material. For example, commonly used promoters are derived from polyoma, Adenovirus 2, Cytomegalovirus (CMV) and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication may be provided with by construction of the vector to include an exogenous origin, such as may be derived from SV40 or other viral (e.g., Polyoma, Adeno, VSV, BPV, CMV) source, or may be provided by the host cell chromosomal replication mechanism. If the vector is integrated into the host cell chromosome, the latter is often sufficient.

Preparing a Recombinant UR Polypeptide

In yet another embodiment, the present invention describes a process of preparing an UR polypeptide comprising transfecting cells with a polynucleotide that encodes an UR polypeptide to produce a transformed host cell; and maintaining the transformed host cell under biological conditions sufficient for expression of the polypeptide. Preferably, the transformed host cell is a eukaryotic cell. Even more preferably, the polynucleotide transfected into the transformed cells comprises a nucleotide base sequence of FIG. 1C or FIG. 1D. Most preferably transfection is accomplished using a hereinbefore disclosed expression vector.

A host cell used in the process is capable of expressing a functional, recombinant UR polypeptide. A variety of cells are amenable to a process of the invention, for instance, yeasts cells, human cell lines, and other eukaryotic cell lines known well to those of the art.

Following transfection, the cell is maintained under culture conditions for a period of time sufficient for expression of an UR polypeptide. Culture conditions are well known in the art and include ionic composition and concentration, temperature, pH and the like. Typically, transfected cells are maintained under culture conditions in a culture medium. Suitable medium for various cell types are well-known in the art. In a preferred embodiment, temperature is from about 20° C. to about 50° C., more preferably from about 30° C. to about 40° C., and even more preferably, about 37° C.

pH is preferably from about a value of 6.0 to a value of about 8.0, more preferably from about a value of about 6.8 to a value of about 7.8, and most preferably, about 7.4. Osmolality is preferably from about 200 milliosmols per liter (mosm/L) to about 400 mosm/l and, more preferably from about 290 mosm/L to about 310 mosm/L. Other biological conditions needed for transfection and expression of an encoded protein are well-known in the art.

Transfected cells are maintained for a period of time sufficient for expression of an UR polypeptide. A suitable time depends inter alia upon the cell type used and is readily determinable by a skilled artisan. Typically, maintenance time is from about 2 to about 14 days.

Recombinant UR polypeptide is recovered or collected either from the transfected cells or the medium in which those cells are cultured. Recovery comprises isolating and purifying the UR polypeptide. Isolation and purification techniques for polypeptides are well-known in the art and include such procedures as precipitation, filtration, chromatography, electrophoresis and the like.

Antibodies

In still another embodiment, the present invention provides an antibody immunoreactive with an UR polypeptide (e.g., one which is specific for UR polypeptide). Preferably, an antibody of the invention is a monoclonal antibody. Preferably, an UR polypeptide comprises an amino acid residue sequence of FIG. 1A or FIG. 1B. Means for preparing and characterizing antibodies are well-known in the art (See, e.g., "Antibodies: A Laboratory Manual", E. Howell and D. Lane, Cold Spring Harbor Laboratory, 1988).

Briefly, a polyclonal antibody is prepared by immunizing an animal with an immunogen comprising a polypeptide or polynucleotide of the present invention, and collecting antisera from that immunized animal. A wide range of animal species may be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well-known in the art, a given polypeptide or polynucleotide may vary in its immunogenicity. It is often necessary therefore to couple the immunogen (e.g., a polypeptide or polynucleotide) of the present invention) with a carrier. Exemplary and preferred carriers are keyhole limpet hemocyanin (KLH) and bovine serum albumin (BSA). Other albumins such as ovalbumin, mouse serum albumin or rabbit serum albumin may also be used as carriers.

Means for conjugating a polypeptide or a polynucleotide to a carrier protein are well-known in the art and include glutaraldehyde, m-maleimidobencoyl-N- hydroxysuccinimide ester, carbodiimide and bis-biazotized benzidine.

As is also well-known in the art, immunogencity to a particular immunogen may be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies inter alia, upon the nature of the immunogen as well as the animal used for immunization. A variety of routes may be used to administer the immunogen (subcutaneous, intramuscular, intradermal, intravenous and intraperitoneal. The production of polyclonal antibodies is monitored by sampling blood of the immunized animal at various points following immunization. When a desired level of immunogenicity is obtained, the immunized animal may be bled and the serum isolated and stored.

In another aspect, the present invention contemplates a process of producing an antibody immunoreactive with an UR polypeptide comprising the steps of (a) transfecting a recombinant host cell with a polynucleotide that encodes an UR polypeptide; (b) culturing the host cell under conditions sufficient for expression of the polypeptide; (c) recovering the polypeptide; and (d) preparing an antibody to the polypeptide. Preferably, the host cell is transfected with a polynucleotide of FIG. 1C or FIG. 1D. The present invention also provides an antibody prepared according to the process described above.

A monoclonal antibody of the present invention may be readily prepared through use of well-known techniques such as those exemplified in U.S. Pat. No. 4,196,265, herein incorporated by reference. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptides. The selected clones may then be propagated indefinitely to provide the monoclonal antibody.

By way of specific example, to produce an antibody of the present invention, mice are injected intraperitoneally with between about 1 to about 200 µg of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radio-labeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they may be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as hypoxanthine-aminopterin-thymidine (HAT) medium. Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) may grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides and polynucleotide of the invention may be recognized as antigens, and thus identified. Once identified, those polypeptides and polynucleotide may be isolated and purified by techniques such as antibody-affinity chromatography. In antibody-affinity chromatography, a monoclonal antibody is bound to a solid substrate and exposed to a solution containing the desired antigen. The antigen is removed from the solution through an immunospecific reaction with the bound antibody. The polypeptide or polynucleotide is then easily removed from the substrate and purified.

Pharmaceutical Compositions

In a preferred embodiment, the present invention provides a pharmaceutical composition comprising an UR polypeptide and a physiologically acceptable carrier. More preferably, a pharmaceutical composition comprises an UR polypeptide comprising an amino acid residue sequence of FIG. 1A or FIG. 1B. Alternatively, pharmaceutical compositions include a polynucleotide that encodes an URpolypeptide and a physiologically acceptable carrier. An example of a useful pharmaceutical composition includes a polynucleotide that has the nucleotide sequence of FIG. 1C or FIG. 1D.

A composition of the present invention is typically administered parenterally in dosage unit formulations containing standard, well-known nontoxic physiologically acceptable carriers, adjuvants, and vehicles as desired. The term parenteral as used herein includes intravenous, intramuscular, intraarterial injection, or infusion techniques.

Injectable preparations, for example sterile injectable aqueous or oleaginous suspensions, are formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminant, such as defective interfering adenovirus particles or endotoxins and other pyrogens such that it does not cause any untoward reactions in the individual receiving the vector construct. Means of purifying the vector may involve the use of buoyant density gradients, such as cesium chloride gradient centrifugation.

A carrier may also be a liposome. Means for using liposomes as delivery vehicles are well-known in the art (See, e.g., Gabizon et al., 1990; Ferruti and Tanzi, 1986; Ranade, 1989).

A transfected cell may also serve as a carrier. By way of example, a liver cell may be removed from an organism, transfected with a polynucleotide of the present invention using methods set forth above and then the transfected cell returned to the organism (e.g., injected intravascularly).

Detecting the UR-Encoding Polynucleotide and UR Polypeptides

Alternatively, the present invention provides a process of detecting an UR polypeptide, wherein the process comprises immunoreacting the polypeptide with an antibody prepared according to a process described above to form an antibody-polypeptide conjugate, and detecting the conjugate.

In yet another embodiment, the present invention contemplates a process of detecting a messenger RNA transcript that encodes an UR polypeptide, wherein the process comprises (a) hybridizing the messenger RNA transcript with a polynucleotide sequence that encodes an UR polypeptide to form a duplex; and (b) detecting the duplex. Alternatively, the present invention provides a process of detecting a DNA molecule that encodes an UR polypeptide, wherein the process comprises (a) hybridizing a DNA molecule with a polynucleotide that encodes an UR polypeptide to form a duplex; and (b) detecting the duplex.

Screening Assays

In yet another aspect, the present invention contemplates a process of screening substances for their ability to interact with an UR polypeptide comprising the steps of providing an UR polypeptide, and testing the ability of selected substances to interact with the UR polypeptide.

Utilizing the methods and compositions of the present invention, screening assays for the testing of candidate substances such as agonists and antagonists of URs may be derived. A candidate substance is a substance which potentially may interact with or modulate, by binding or other intramolecular interaction, an UR polypeptide. In some instances, such a candidate substance will be an agonist of the receptor and in other instances may exhibit antagonistic attributes when interacting with the receptor polypeptide. In other instances, such substances may have mixed agonistic and antagonistic properties or may modulate the UR in other ways.

Recombinant receptor expression systems of the present invention possess definite advantages over tissue-based systems. Such a method of the present invention makes it possible to produce large quantities of URs for use in screening assays. More important, however, is the relative purity of the receptor polypeptides provided by the present invention. A relatively pure polypeptide preparation for assaying a protein-protein interaction makes it possible to use elutive methods without invoking competing, and unwanted, side-reactions.

Cloned expression systems such as those of the present invention are also useful where there is difficulty in obtaining tissue that satisfactorily expresses a particular receptor. Cost is another very real advantage, at least with regard to the microbial expression systems of the present invention. For antagonists in a primary screen, microorganism expression systems of the present invention are inexpensive in comparison to prior art tissue-screening methods.

Traditionally, screening assays employed the use of crude receptor preparations. Typically, animal tissue slices thought to be rich in the receptor of interest was the source of the receptor. Alternatively, investigators homogenized the tissue and used the crude homogenate as a receptor source. A major difficulty with this approach is the provision that the tissue contain only a single receptor type being expressed. The data obtained therefore could not be definitively correlated with a particular receptor. With the recent cloning of receptor sub-types and sub-sub-types, this difficulty is highlighted. A second fundamental difficulty with the traditional approach is the unavailability of human tissue for screening potential drugs. The traditional approach almost invariably utilized animal receptors. With the cloning of human receptors, there is a need for screening assays which utilize human receptors.

With the availability of cloned receptors, recombinant receptor screening systems have several advantages over tissue based systems. A major advantage is that the investigator may now control the type of receptor that is utilized in a screening assay. Specific receptor sub-types and sub-sub-types may be preferentially expressed and its interaction with a ligand may be identified. Other advantages include the availability of large amounts of receptor, the availability of rare receptors previously unavailable in tissue samples, and the lack of expenses associated with the maintenance of live animals.

Screening assays of the present invention generally involve determining the ability of a candidate substance to bind to the receptor and to affect the activity of the receptor, such as the screening of candidate substances to identify those that inhibit or otherwise modify the receptor's function. Typically, this method includes preparing recombinant receptor polypeptide, followed by testing the recombinant polypeptide or cells expressing the polypeptide with a candidate substance to determine the ability of the substance to affect its physiological function. In preferred embodiments, the invention relates to the screening of candidate substances to identify those that affect the enzymatic activity of the human receptor, and thus can be suitable for use in humans.

A screening assay provides a receptor under conditions suitable for the binding of an agent to the receptor. These conditions include but are not limited to pH, temperature, tonicity, the presence of relevant cofactors, and relevant modifications to the polypeptide such as glycosylation or prenylation. It is contemplated that the receptor can be expressed and utilized in a prokaryotic or eukaryotic cell. The host cell expressing the receptor can be used whole or the receptor can be isolated from the host cell. The receptor can be membrane bound in the membrane of the host cell or it can be free in the cytosol of the host cell. The host cell can also be fractionated into sub-cellular fractions where the receptor can be found. For example, cells expressing the receptor can be fractionated into the nuclei, the endoplasmic reticulum, vesicles, or the membrane surfaces of the cell.

pH is preferably from about a value of 6.0 to a value of about 8.0, more preferably from about a value of about 6.8 to a value of about 7.8, and most preferably, about 7.4. In a preferred embodiment, temperature is from about 20° C. to about 50° C., more preferably, from about 30° C. to about 40° C., and even more preferably about 37° C. Osmolality is preferably from about 5 milliosmols per liter (mosm/L) to about 400 mosm/l, and more preferably, from about 200 milliosmols per liter to about 400 mosm/l and, even more preferably from about 290 mosm/L to about 310 mosm/L. The presence of cofactors can be required for the proper functioning of the receptor. Typical cofactors include sodium, potassium, calcium, magnesium, and chloride. In addition, small, non-peptide molecules, known as prosthetic groups may also be required. Other biological conditions needed for receptor function are well-known in the art.

It is well-known in the art that proteins can be reconstituted in artificial membranes, vesicles or liposomes. (Danboldt et al., 1990). The present invention contemplates that the receptor can be incorporated into artificial membranes, vesicles or liposomes. The reconstituted receptor can be utilized in screening assays.

It is further contemplated that a receptor of the present invention can be coupled to a solid support, e.g., to agarose beads, polyacrylamide beads, polyacrylic beads or other solid matrices capable of being coupled to polypeptides. Well-known coupling agents include cyanogen bromide (CNBr), carbonyldiimidazole, tosyl chloride, and glutaraldehyde.

In a typical screening assay for identifying candidate substances, one employs the same recombinant expression host as the starting source for obtaining the receptor polypeptide, generally prepared in the form of a crude homogenate. Recombinant cells expressing the receptor are washed and homogenized to prepare a crude polypeptide homogenate in a desirable buffer such as disclosed herein. In a typical assay, an amount of polypeptide from the cell homogenate, is placed into a small volume of an appropriate assay buffer at an appropriate pH. Candidate substances, such as agonists and antagonists, are added to the admixture in convenient concentrations and the interaction between the candidate substance and the receptor polypeptide is monitored.

Where one uses an appropriate known substrate for the receptor, one can, in the foregoing manner, obtain a baseline activity for the recombinantly produced receptor. Then, to test for inhibitors or modifiers of the receptor function, one can incorporate into the admixture a candidate substance whose effect on the receptor is unknown. By comparing reactions which are carried out in the presence or absence of the candidate substance, one can then obtain information regarding the effect of the candidate substance on the normal function of the receptor.

Accordingly, this aspect of the present invention will provide those of skill in the art with methodology that allows for the identification of candidate substances having the ability to modify the action of UR polypeptides in one or more manner.

Additionally, screening assays for the testing of candidate substances are designed to allow the determination of structure-activity relationships of agonists or antagonists with the receptors, e.g., comparisons of binding between naturally-occurring hormones or other substances capable of interacting or otherwise modulating with the receptor; or comparison of the activity caused by the binding of such molecules to the receptor.

In certain aspects, the polypeptides of the invention are crystallized in order to carry out x-ray crystallographic studies as a means of evaluating interactions with candidate substances or other molecules with the UR polypeptide. For instance, the purified recombinant polypeptides of the invention, when crystallized in a suitable form, are amenable to detection of intra-molecular interactions by x-ray crystallography.

The recombinantly-produced UR polypeptide may be used in screening assays for the identification of substances which may inhibit or otherwise modify or alter the function of the receptor. The use of recombinantly-produced receptor is of particular benefit because the naturally-occurring receptor is present in only small quantities and has proven difficult to purify. Moreover, this provides a ready source of receptor, which has heretofore been unavailable.

A screening assay of the invention, in preferred embodiments, conveniently employs an UR polypeptide directly from the recombinant host in which it is produced. This is achieved most preferably by simply expressing the selected polypeptide within the recombinant host, typically a eukaryotic host, followed by preparing a crude homogenate which includes the enzyme. A portion of the crude homogenate is then admixed with an appropriate effector of the receptor along with the candidate substance to be tested. By comparing the binding of the selected effector to the receptor in the presence or absence of the candidate substance, one may obtain information regarding the physiological properties of the candidate substance.

The receptor has been expressed in both prokaryotic and eukaryotic cells. Receptors have been expressed in E. coli (Bertin et al., 1992), in yeast (King et al., 1990) and in mammalian cells (Bouvier et al., 1988). A cell expressing a receptor may be used whole to screen agents. For example, cells expressing the receptor of the present invention may be exposed to radiolabeled agent and the amount of binding of the radiolabeled agent to the cell may be determined.

There are believed to be a wide variety of embodiments which may be employed to determine the effect of the candidate substance on the receptor polypeptides of the invention, and the invention is not intended to be limited to any one such method. However, it is generally desirable to employ a system wherein one may measure the ability of the receptor polypeptide to bind to and or be modified by the effector employed in the presence of a particular substance.

The detection of an interaction between an agent and a receptor may be accomplished through techniques well-known in the art. These techniques include but are not limited to centrifugation, chromatography, electrophoresis and spectroscopy The use of isotopically labeled reagents in conjunction with these techniques or alone is also contemplated. Commonly used radioactive isotopes inclued $^3$H, $^{14}$C, $^{22}$Na, $^{32}$P, $^{35}$S, $^{45}$Ca, $^{60}$Co, $^{125}$I, and $^{131}$I. Commonly used stable isotopes include $^2$H, $^{13}$C, $^{15}$N, $^{18}$O.

For example, if an agent binds to the receptor of the present invention, the binding may be detected by using radiolabeled agent or radiolabeled receptor. Briefly, if radiolabeled agent or radiolabeled receptor is utilized, the agent-receptor complex may be detected by liquid scintillation or by exposure to x-ray film.

When an agent modifies the receptor, the modified receptor may be detected by differences in mobility between the modified receptor and the unmodified receptor through the use of chromatography, electrophoresis or centrifugation. When the technique utilized is centrifugation, the differences in mobility is known as the sedimentation coefficient. The modification may also be detected by differences between the spectroscopic properties of the modified and unmodified receptor. As a specific example, if an agent covalently modifies a receptor, the difference in retention times between modified and unmodified receptor on a high pressure liquid chromatography (HPLC) column may easily be detected. Alternatively, the spectroscopic differences between modified and unmodified receptor in the nuclear magnetic resonance (NMR) spectra may be detected. Or, one may focus on the agent and detect the differences in the spectroscopic properties or the difference in mobility between the free agent and the agent after modification of the receptor.

When a secondary polypeptide is provided, the agent-receptor-secondary polypeptide complex or the receptor-secondary polypeptide complex may be detected by differences in mobility or differences in spectroscopic properties as described above. The interaction of an agent and a receptor may also be detected by providing a reporter gene. Well-known reporter genes include β-Gal, chloramphenicol (Cml) transferase (CAT) and luciferase. The reporter gene is expressed by the host and the enzymatic reaction of the reporter gene product may be detected.

In one example, a mixture containing the polypeptide, effector and candidate substance is allowed to incubate. The unbound effector is separable from any effector/receptor complex so formed. One then simply measures the amount of each (e.g., versus a control to which no candidate substance has been added). This measurement may be made at various time points where velocity data is desired. From this, one determines the ability of the candidate substance to alter or modify the function of the receptor.

Numerous techniques are known for separating the effector from effector/receptor complex, and all such methods are intended to fall within the scope of the invention. Use of thin layer chromatographic methods (TLC), HPLC, spectrophotometric, gas chromatographic/mass spectrophotometric or NMR analyses. It is contemplated that any such technique may be employed so long as it is capable of differentiating between the effector and complex, and may be used to determine enzymatic function such as by identifying or quantifying the substrate and product.

Screening Assays for UR Polypeptides

The present invention provides a process of screening a biological sample for the presence of an UR polypeptide. A biological sample to be screened may be a biological fluid such as extracellular or intracellular fluid, a cell, a tissue extract, a tissue homogenate or a histological section. A biological sample may also be an isolated cell (e.g., in culture) or a collection of cells such as in a tissue sample or histology sample. A tissue sample may be suspended in a liquid medium or fixed onto a solid support such as a microscope slide.

In accordance with a screening assay process, a biological sample is contacted with an antibody specific for UR polypeptide whose presence is being assayed. Typically, one mixes the antibody and the UR polypeptide, and either the antibody or the sample with the UR polypeptide may be affixed to a solid support (e.g., a column or a microtiter plate). Optimal conditions for the reaction may be accomplished by adjusting temperature, pH, ionic concentration, etc.

Ionic composition and concentration may range from that of distilled water to a 2 molal solution of NaCl. Preferably, osmolality is from about 100 mosmols/l to about 400 mosmols/l, and more preferably, from about 200 mosmols/l to about 300 mosmols/l. Temperature preferably is from about 4° C. to about 100° C., more preferably from about 15° C. to about 50° C., and even more preferably from about 25° C. to about 40° C. pH is preferably from about a value of 4.0 to a value of about 9.0, more preferably from about a value of 6.5 to a value of about 8.5, and even more preferably, from about a value of 7.0 to a value of about 7.5. The only limit on biological reaction conditions is that the conditions selected allow for antibody-polypeptide conjugate formation and that the conditions do not adversely affect either the antibody or the UR polypeptide.

Incubation time varies with the biological conditions used, the concentration of antibody and polypeptide and the nature of the sample (e.g., fluid or tissue sample). Means for determining exposure time are well-known to one of ordinary skill in the art. Typically, where the sample is fluid and the concentration of polypeptide in that sample is about $10^{-10}$M, exposure time is from about 10 min to about 200 min.

UR polypeptide in the sample is determined by detecting the formation and presence of antibody-URpolypeptide conjugates. Means for detecting such antibody-antigen (e.g., receptor polypeptide) conjugates or complexes are well-known in the art and include such procedures as centrifugation, affinity chromatography and the like, binding of a secondary antibody to the antibody-candidate receptor complex. Detection may be accomplished by measuring an indicator affixed to the antibody. Exemplary and well-known such indicators include radioactive labels (e.g., $^{32}$P, $^{125}$I, $^{14}$C), a second antibody or an enzyme such as horse radish peroxidase. Methods for affixing indicators to antibodies are well-known in the art. Commercial kits are available.

Screening Assay for α-UR Antibody

The present invention provides a process of screening a biological sample for the presence of antibodies immunoreactive with an UR polypeptide (i.e., α-UR antibody). In accordance with such a process, a biological sample is exposed to an UR polypeptide under biological conditions and for a period of time sufficient for antibody-polypeptide conjugate formation and the formed conjugates are detected.

Screening Assay for a Polynucleotide Encoding UR Polypeptide

A DNA molecule and, particularly a probe molecule, may be used for hybridizing as oligonucleotide probes to a DNA source suspected of possessing an UR polypeptide encoding polynucleotide or gene. The probing is usually accomplished by hybridizing the oligonucleotide to a DNA source suspected of possessing such a receptor gene. In some cases, the probes constitute only a single probe, and in others, the probes constitute a collection of probes based on a certain amino acid sequence or sequences of the UR polypeptide and account in their diversity for the redundancy inherent in the genetic code.

A suitable source of DNA for probing in this manner is capable of expressing UR polypeptides and may be a genomic library of a cell line of interest. Alternatively, a source of DNA may include total DNA from the cell line of interest. Once the hybridization process of the invention has identified a candidate DNA segment, one confirms that a positive clone has been obtained by further hybridization, restriction enzyme mapping, sequencing and/or expression and testing.

Alternatively, such DNA molecules may be used in a number of techniques including their use as: (1) diagnostic tools to detect normal and abnormal DNA sequences in DNA derived from patient's cells; (2) means for detecting and isolating other members of the UR family and related polypeptides from a DNA library potentially containing such sequences; (3) primers for hybridizing to related sequences for the purpose of amplifying those sequences; and (4) primers for altering the native URDNA sequences; as well as other techniques which rely on the similarity of the DNA sequences to those of the UR DNA segments herein disclosed.

As set forth above, in certain aspects, DNA sequence information provided by the invention allows for the preparation of relatively short DNA (or RNA) sequences (e.g., probes) that specifically hybridize to encoding sequences of the selected UR gene. In these aspects, nucleic acid probes of an appropriate length are prepared based on a consideration of the selected UR encoding sequence (e.g., a nucleic acid sequence such as shown in FIG. 1C or FIG. 1D. The ability of such nucleic acid probes to specifically hybridize to UR encoding sequences lend them particular utility in a variety of embodiments.

Most importantly, the probes are useful in a variety of assays for detecting the presence of complementary sequences in a given sample. These probes are useful in the preparation of mutant species primers and primers for preparing other genetic constructions.

To provide certain of the advantages in accordance with the invention, a preferred nucleic acid sequence employed for hybridization studies or assays includes probe sequences that are complementary to at least an about 14 to about 40 or so long nucleotide stretch of the UR encoding sequence, such as shown in FIG. 1C or FIG. 1D. A size of at least 14 nucleotides in length helps to ensure that the fragment is of sufficient length to form a duplex molecule that is both stable and selective. Molecules having complementary sequences over stretches greater than 14 bases in length are generally preferred, though, to increase stability and selectivity of the hybrid, and thereby improve the quality and degree of specific hybrid molecules obtained. One will generally prefer to design nucleic acid molecules having gene-complementary stretches of about 14 to about 20 nucleotides, or even longer where desired. Such fragments may be readily prepared by, for example, directly synthesizing the fragment by chemical means, by application of nucleic acid reproduction technology, such as the PCR™ technology of U.S. Pat. No. 4,603,102, herein incorporated by reference, or by introducing selected sequences into recombinant vectors for recombinant production.

Accordingly, a nucleotide sequence of the present invention may be used for its ability to selectively form duplex molecules with complementary stretches of the gene. Depending on the application envisioned, one employs varying conditions of hybridization to achieve varying degrees of selectivity of the probe toward the target sequence. For applications requiring a high degree of selectivity, one typically employs relatively stringent conditions to form the hybrids. For example, one selects relatively low salt and/or high temperature conditions, such as provided by about 0.02M to about 0.15M NaCl at temperatures of about 50° C. to about 70° C. Such conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate UR coding sequences from related species, functional equivalents, or the like, less stringent hybridization conditions are typically needed to allow formation of the heteroduplex. Under such circumstances, one employs conditions such as from about 0.15M to about 0.9M salt, at temperatures ranging from about 20° C. to about 55° C. Cross-hybridizing species may thereby be readily identified as positively hybridizing signals with respect to control hybridizations. In any case, it is generally appreciated that conditions may be rendered more stringent by the addition of increasing amounts of formamide, which serves to destabilize the hybrid duplex in the same manner as increased temperature. Thus, hybridization conditions may be readily manipulated, and thus will generally be a method of choice depending on the desired results.

In certain embodiments, it is advantageous to employ a nucleic acid sequence of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred embodiments, one likely employs an enzyme tag such a urease, alkaline phosphatase or peroxidase, instead of radioactive or other environmentally undesirable reagents. In the case of enzyme tags, calorimetric indicator substrates are known which may be employed to provide a means visible to the human eye or spectrophotometrically, to identify specific hybridization with complementary nucleic acid-containing samples.

In general, it is envisioned that the hybridization probes described herein are useful both as reagents in solution hybridization as well as in embodiments employing a solid phase. In embodiments involving a solid phase, the sample containing test DNA (or RNA) is adsorbed or otherwise affixed to a selected matrix or surface. This fixed, single-stranded nucleic acid is then subjected to specific hybridization with selected probes under desired conditions. The selected conditions depend inter alia on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantified, by means of the label.

Assay Kits

In another aspect, the present invention contemplates a diagnostic assay kit for detecting the presence of UR polypeptide in a biological sample, where the kit comprises a first container containing a first antibody capable of immunoreacting with UR polypeptide, with the first antibody present in an amount sufficient to perform at least one assay. An assay kit of the invention further optionally includes a second container containing a second antibody that immunoreacts with the first antibody. The antibodies used in the assay kits of the present invention may be monoclonal or polyclonal antibodies. For convenience, one may also provide the first antibody affixed to a solid support. Additionally, the first and second antibodies may be combined with an indicator, (e.g., a radioactive label or an enzyme).

The present invention also contemplates a diagnostic kit for screening agents for their ability to interact with an UR. Such a kit will contain an UR of the present invention. The kit may further contain reagents for detecting an interaction between an agent and a receptor of the present invention. The provided reagent may be radiolabeled. The kit may also contain a known radiolabeled agent that binds or interacts with a receptor of the present invention.

The present invention provides a diagnostic assay kit for detecting the presence, in a biological sample, of a polynucleotide that encodes an UR polypeptide, the kits comprising a first container that contains a second polynucleotide identical or complementary to a segment of at least about 14 contiguous nucleotide bases of a polynucleotide of FIG. 1C or FIG. 1D.

In another embodiment, the present invention contemplates a diagnostic assay kit for detecting the presence, in a biological sample, of an antibody immunoreactive with an UR polypeptide, the kits comprising a first container containing an UR polypeptide that immunoreacts with the antibody, with the polypeptide present in an amount sufficient to perform at least one assay. The reagents of the kit may be provided as a liquid solution, attached to a solid support or as a dried powder. When the reagent is provided in a liquid solution, the liquid solution is an aqueous solution. When the reagent provided is attached to a solid support, the solid support may be chromatograph media or a microscope slide. When the reagent provided is a dry powder, the powder may be reconstituted by the addition of a suitable solvent. The solvent may also be included in the kit.

Process of Modifying the Function of a Nuclear Receptor using UR

In another aspect, the present invention provides a process of altering the function of a nuclear receptor. In accordance with that process, a nuclear receptor is exposed to an UR of the present invention. A preferred nuclear receptor used in such a process is the same as set forth above and includes nuclear receptors for thyroid hormone, vitamin D, retinoic acid and the like. Preferred URs and their corresponding DNA sequences are shown in FIG. 1A, FIG. 1B, FIG. 1C, and FIG. 1D.

BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein:

FIG. 1A. Amino acid sequence of hUR (SEQ ID NO:1).

FIG. 1B. Amino acid sequence of rUR (SEQ ID NO:2).

FIG. 1C. Nucleotide sequence of the gene encoding hUR (SEQ ID NO:3).

FIG. 1D. Nucleotide sequence of the gene encoding rUR (SEQ ID NO:4).

FIG. 7. Schematic diagram of the interaction of UR with other nuclear receptors (RAR, TR and RXR).

Figure 10A:
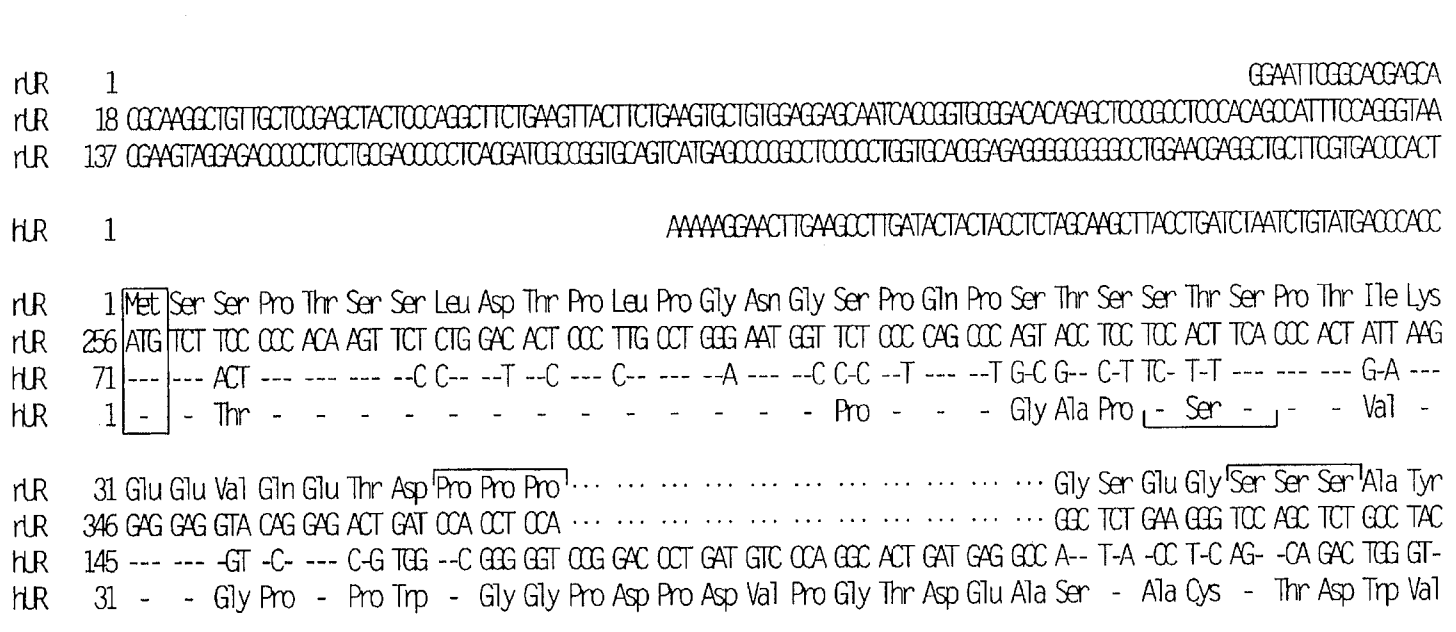
Figure 10B:
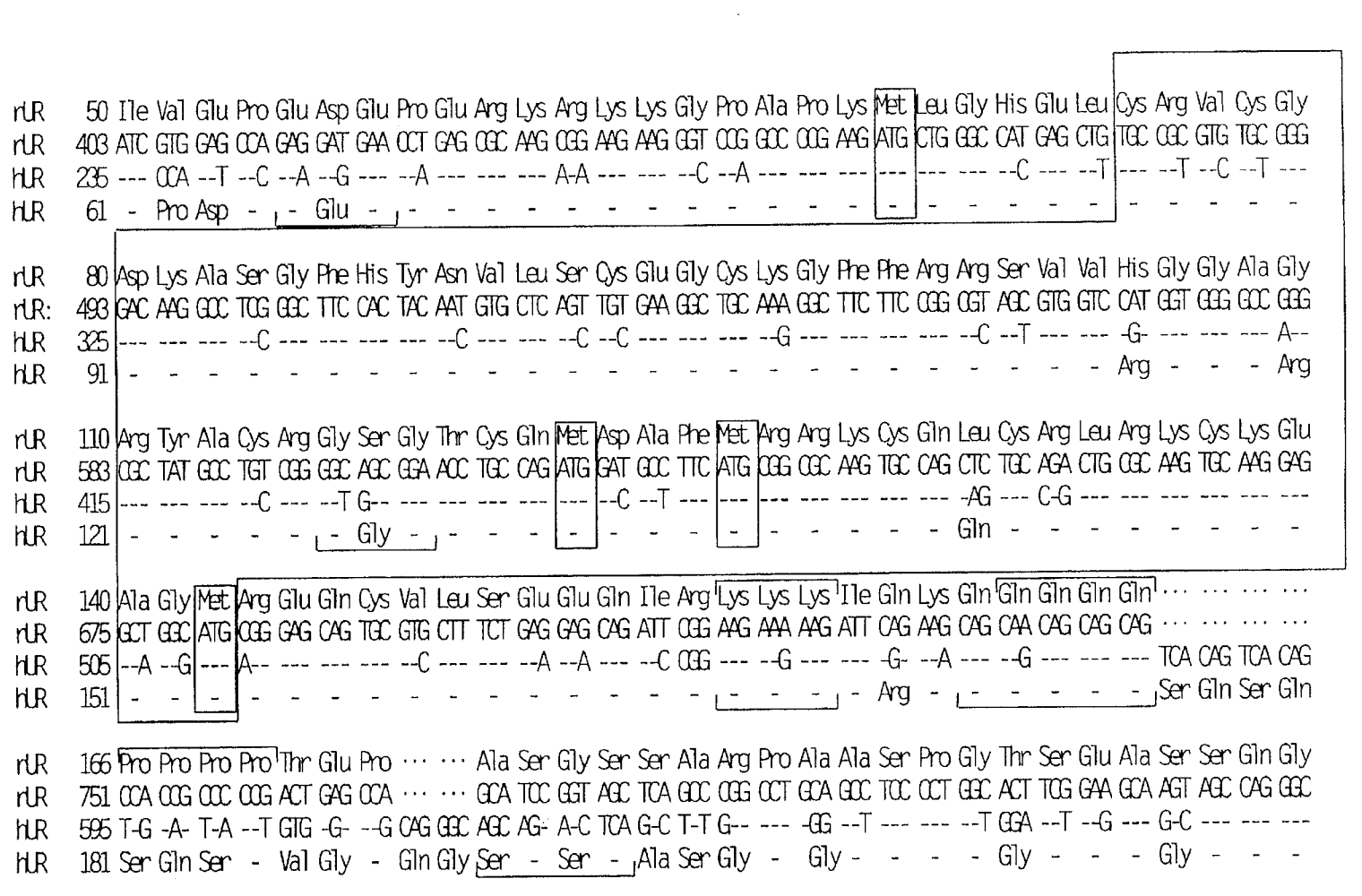
Figure 10C:
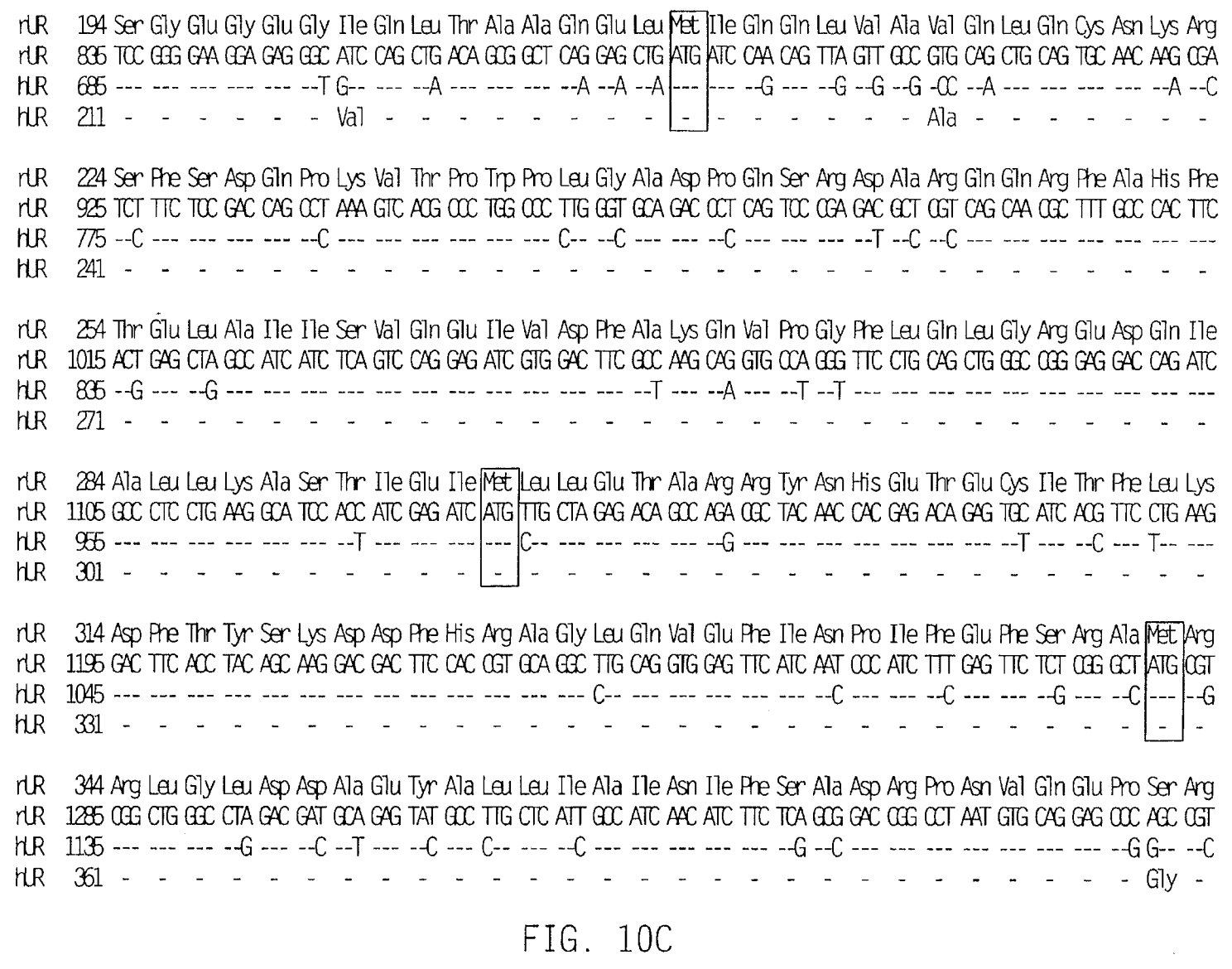
Figure 10D:
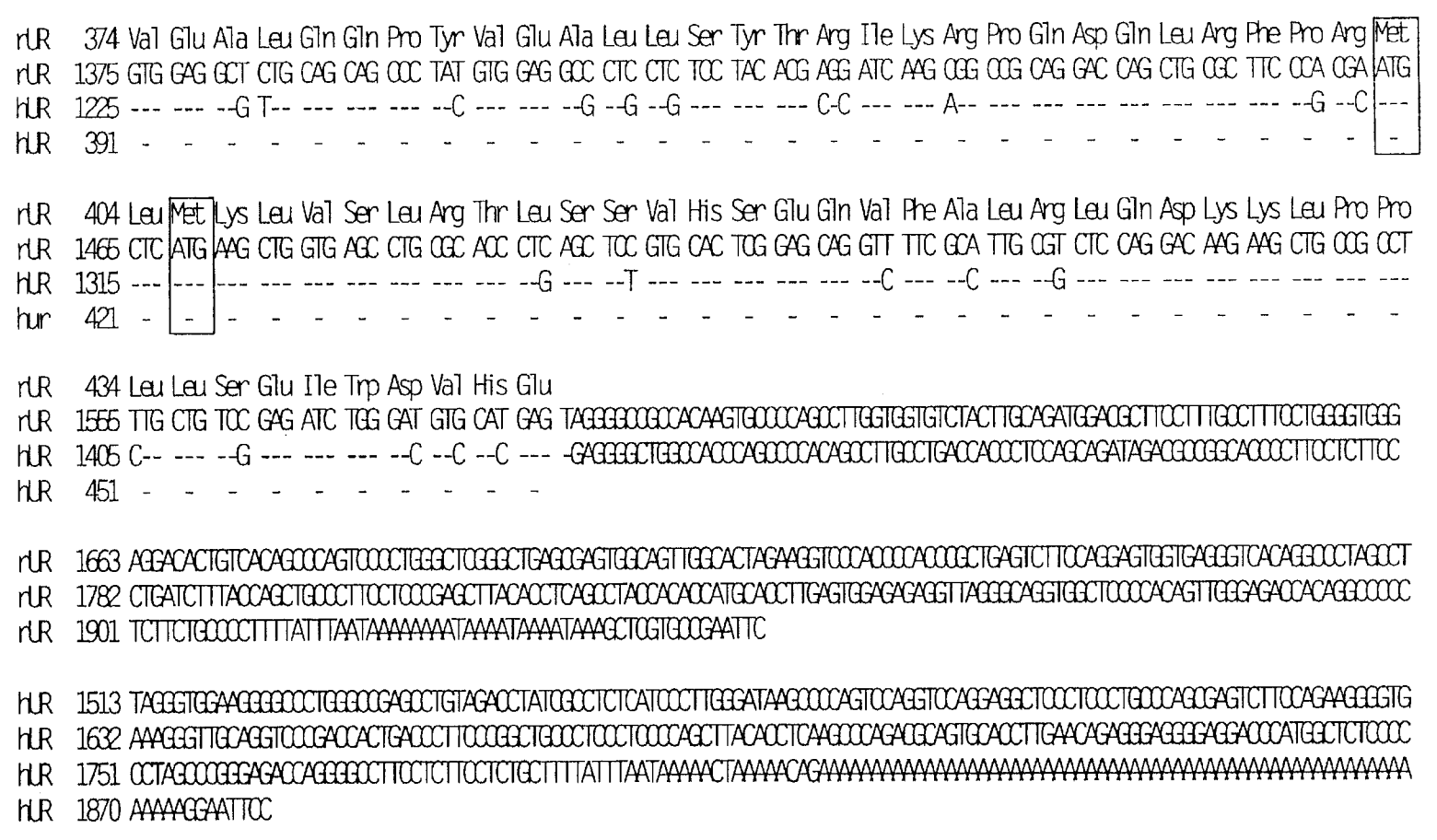

FIG. 10. Shown in four sheets (designated FIG. 10A, FIG. 10B, FIG. 10C and FIG. 10D) is the optimized DNA sequence alignment of rodent (rUR) (SEQ ID NO:3) and human (hUR) (SEQ ID NO:1) ubiquitous nuclear receptor. Beneath the DNA sequence alignment is the deduced amino acid residue sequence of both rUR (SEQ ID NO:2) and hUR (SEQ ID NO:2) polypeptides.

DETAILED DESCRIPTION OF THE PREFERRED EMBODIMENTS

Figure 2:
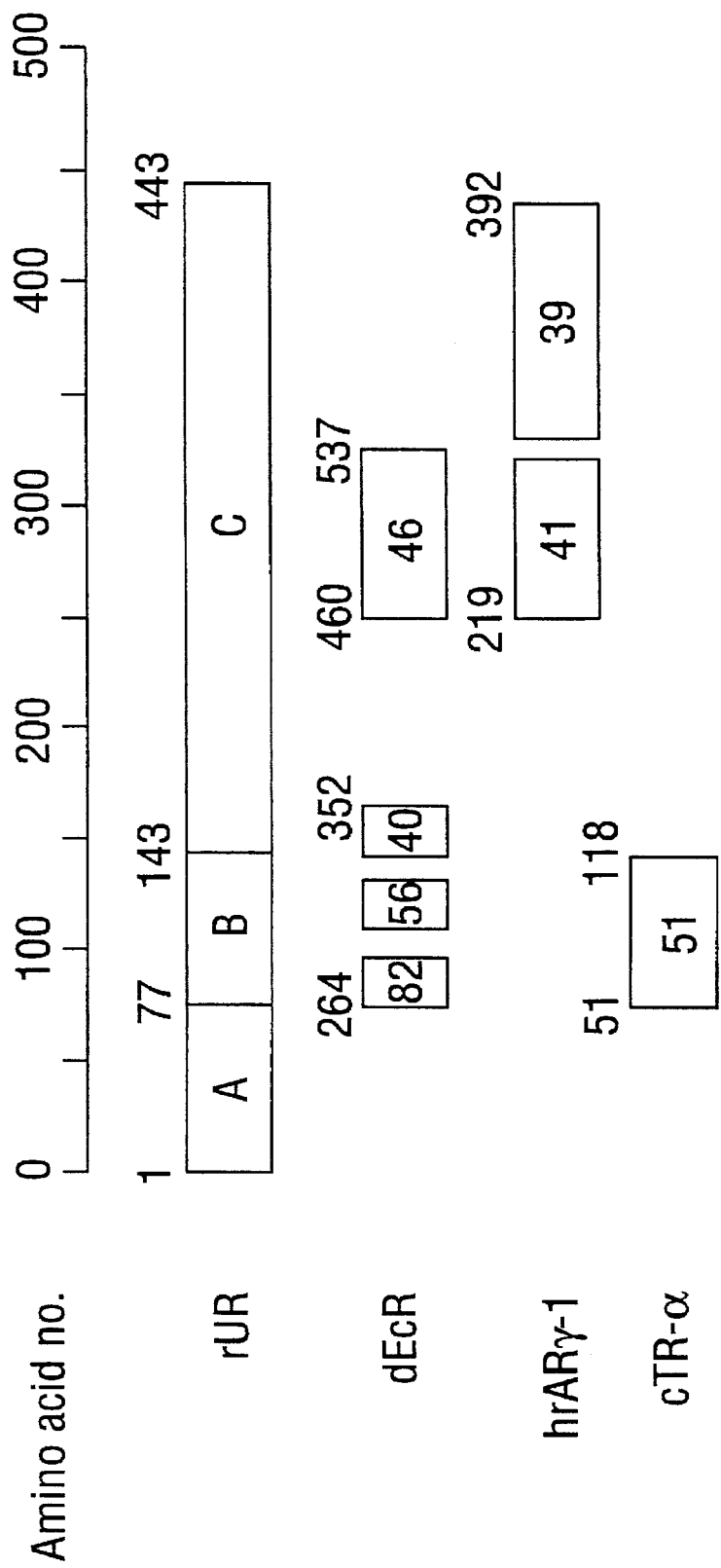
FIG. 2. Schematic comparison of rUR amino acid sequence and those of known receptors with the highest homology to rUR. Comparisons between domains are expressed as percent amino acid identity (bold numbers). Segment A is the amino-terminal domain; segment B is the DNA-binding domain; and segment C is the ligand-binding domain.

The present invention provides DNA segments, purified polypeptides, methods for obtaining antibodies, methods of cloning and using recombinant host cells necessary to obtain and use URs. Accordingly, the present invention concerns generally compositions and methods for the preparation and use of URs.

In a preferred embodiment, exposing a nuclear receptor to an ubiquitous nuclear receptor is accomplished in the presence of a second molecule. A preferred second molecule is all or portion of a second nuclear receptor such as RAR or RXR. A description of how UR affects the function of nuclear receptors may be found hereinafter in the examples.

UR Genes and Isoforms in Other Organisms

UR may be considered as a member of a subfamily of nuclear receptors that include TR and RAR. These subfamily members often have several isoforms coded by multiple genes located at different chromosomal loci. TRs have α and β isoforms while RARs have α, β and γ isoforms. It is probable that UR isoforms are also encoded by multiple genes. Since DBDs among different isoforms usually have a high homology, the DBD sequences of UR may be used as probes to screen cDNA libraries. Considering the fact that different isoforms of nuclear receptors may have different tissue distribution patterns and may be expressed to different extents in different tissues, the second zinc finger of hUR (which is usually coded by one exon), is used as a probe to screen genomic libraries for genes encoding UR isoforms.

The present invention has determined hybridization patterns in Southern analyses of restriction digests of human genomic DNAs under nonstringent conditions with a nearly full-length hUR cDNA as probe and has shown that more than one hUR gene is present. DNA sequence analysis of the appropriate restriction fragments of clones hybridizing to the URprobe may determine their relationship to UR.

The present invention also provides cDNA libraries which are useful for screening of additional UR isoforms. Using the nucleotide sequences of the present invention, it is possible to determine structural and genetic information (including restriction enzyme analysis and DNA sequencing) concerning these positive clones. Such information will provide important information concerning the role of these isoforms in vivo and in vitro. rUR & hUR sequence information may be used to analyze UR cDNAs and UR-like gene sequences in other organisms. Using PCR™ techniques, restriction enzyme analysis, and DNA sequencing, the structure of these UR-like isoform genes may be determined with relative facility.

Tumorigenicity Analysis

It is important to know whether altered prostate cells have different tumorigenicity patterns in thymic nude mice. The present invention is useful in analyzing such patterns. LNCaP cells (poor in UR) produce localized tumors while PC-3 cells (very rich in UR) produce metastatic tumors in nude mice and this pattern may be altered by UR expression. It has been suggested that aberrations in epithelial-stromal interactions occur during he course of neoplastic progression. Since tumor growth resulting from LNCaP or PC-3 cell inoculation is stimulated by mixing of these cells with bone- or prostate-derived fibroblasts, retroviral infection of these fibroblasts (URpoor) with URmay be performed to determine whether URmay play a role in stimulating or inhibiting tumor formation and metastasis.

Fibroblasts from kidney or other organs which are not permissive containing mutated or antisense UR sequences may be used as controls in the determination of UR effects upon tumorigenesis. Since androgens, estrogens and growth factors greatly affect fibroblast-mediated acceleration of epithelial tumor growth, these hormones as well as their antagonists (hydroxyflutamide, tamoxifine, etc.) may be used to analyze the hormonal effect on UR action in host animals.

Other Nuclear Reeeptors

UR may coordinate the functions of other nuclear receptors including RAR, RXR, TR, and VDR (FIG. 7). Studies using synthetic direct repeats with different spacing of nucleotides 0 to 6 (DR0 to DR6) and gel shift assays have been performed to find out whether UR may affect the interaction of other nuclear receptors. Studies have also been performed in which COS cells were co-transfected or infected with UR and other nuclear receptors genes, using reporter gene construct containing specific synthetic repeats, e.g., a promoter sequence of human c-fos and CAT gene).

These results demonstrated that UR stimulation or inhibition of CAT expression in the presence of nuclear receptors were dependent on the type of receptor. These observation suggest that UR provides specificity for the interaction of nuclear receptors and their partners with specific promoter construct: in the absence of UR, certain combinations of nuclear receptors may activate genes with very little specificity whereas in the presence of UR only certain genes are activated. The loss of such regulation, either due to the absence or lower levels of UR or its ligands or due to mutation of the UR gene may cause abnormality (including tumorigenesis and hormone insensitivity) during cell differentiation, growth or proliferation.

UR may be involved in cell-cell interaction especially between epithelial cell and basal or mesenchyme (stroma) cells, since UR is found predominantly in epithelial cells. This suggests that stroma cells produce hormonal ligands to epithelial cells to stimulate UR functions which are involved in regulation of the production of factors that are essential in cell-cell interaction.

Such an interaction is important in organogenesis and epithelial cell-dependent secretory functions. UR may also play a role during certain stages of cell life cycle. An indication supporting this view is that not all cells in the same organs or cells in cultures contain UR by immunocytochemical localization.

The following examples illustrate preferred embodiments of the invention. Certain aspects of the following examples are described in terms of techniques and procedures found or contemplated by the present inventors to work well in the practice of the invention. These examples are exemplified through the use of standard laboratory practices of the inventor.

It should be appreciated by those of skill in the art that the techniques disclosed in the examples which follow represent techniques discovered by the inventor to function well in the practice of the invention, and thus may be considered to constitute preferred modes for its practice. However, those of skill in the art should, in light of the present disclosure, appreciate that many changes may be made in the specific embodiments which are disclosed and still obtain a like or similar result without departing from the spirit and scope of the invention.

EXAMPLE 1

PREPARATION OF A cDNA LIBRARY

Vaginal tissue from ten female Sprague-Dawley rats (SASCO, Omaha, Nebr.) (three month old, body weight >200 g) were collected by cervical dislocation and frozen in liquid nitrogen. They were homogenized with mortar and pestle in guanidine thiocyanate buffer (4M guanidine thiocyanate, 0.5% N-lauryl sarcosine, 25 mM Tris-HCl (pH 7.5), and 0.1M 2-mercaptoethanol) and RNA was isolated using the methods of the manufacturer (RNA Isolation Kit, catalog #200345, Stratagene, La Jolla, Calif.). 5 mg of total RNA was used as templates for the construction of a Lambda ZAP™ II cDNA library (commercially prepared by Stratagene). Inserts were cloned at the EcoRI site of the vector. cDNA was also prepared in the same way by using total RNA isolated from androgen insensitive human prostate cancer cell (PC-3 cell line) cultures.

Screening of cDNA Library

Five synthetic oligonucleotide preparations shown in Table 3 were pooled together and used as probes to screen cDNA libraries. The sequences of these nucleotide probes were derived from the sequences in the conserved DNA binding region of steroid/thyroid receptor super family.

TABLE 3

| | | | | | | | | | | |
|---|---|---|---|---|---|---|---|---|---|---|
| A: | 5'-TT | AAA | GAA | GAC | TTT | ACA | GCT | TCC | ACA | (SEQ ID NO: 7) |
| | | G | | T | C | | G | C | | (SEQ ID NO: 8) |
| | | | | | | | | G | | (SEQ ID NO: 9) |
| I: | 5'-CT | AAA | GAA | NCC | CTT | GCA | GCC | NTC | ACA | GGT | (SEQ ID NO: 10) |
| | | G | | | | | | | | | (SEQ ID NO: 11) |
| II: | 5'-TT | AAA | GAA | TAC | TTT | GCA | GCT | TCC | ACA | NGT | (SEQ ID NO: 12) |
| | | G | | G | C | | | G | | | (SEQ ID NO: 13) |
| AA: | 5'-C | CCC | GTA | GTG | ACA | NCC | AGA | AGC | NTC | ATC | (SEQ ID NO: 14) |
| | | T | A | A | G | | T | G | | | (SEQ ID NO: 15) |
| BB: | 5'-A | GTG | NAA | GCC | NGT | GGC | CCG | GTC | NCC | ACA | (SEQ ID NO: 16) |
| | | | TT | A | | | TT | | | | (SEQ ID NO: 17) | where N = Inosine

A pool of these oligonucleotides was end-labeled with T4 polynucleotide kinase (New England Biolabs, Boston, Mass.) and [γ-$^{32}$P]ATP (New England Nuclear, Boston, Mass.). Free ATP was removed by Sep-Pak® $C_{18}$ cartridge (Millipore, Inc., Bedford, Mass.) solid phase extraction. Average specificity is $2 \times 10^8$ cpm/µg.

Nitrocellulose membranes (Schleicher and Schuell, Keene, N.H.) were used to blot phage DNA from plates. A total of $10^6$ phages from unamplified rat vagina Lambda ZAP™ II library were blotted and screened. The blotted membranes were incubated with H-Buffer (6× SSPE [52.62 g NaCl, 8.28 g $NaH_2PO_4$, 2.22 g EDTA/l, adjusted to pH 7.4 with NaOH] 1× Denhardt's Solution, 0.5% sodium dodecyl sulfate (SDS), 1 mM EDTA, 100 µg/ml denatured salmon testis DNA] without probe first and then incubated with radioactive probes ($10^5$ cpm/ml) at 42° C. overnight in H-Buffer.

The blotted nitrocellulose membranes were washed with 6× SSPE containing 0.5% SDS at room temperature for one hour (h) and then at 50° C. for 10 minutes (min). Autoradiography was performed using X-OMAT AR film (Eastman Kodak, Rochester, NY) at −80° C. overnight.

Positive clones were picked up and rescreened two more times to obtain pure single phage clones. pBluescript phage plasmids were excised from positive Lambda ZAP™ II phages using the phage system according to the methods of the manufacture (Stratagene ExAssist™/SOLR®).

EXAMPLE 2

DETERMINATION OF NUCLEOTIDE SEQUENCE OF cDNAs AND DEDUCED AMINO ACID SEQUENCES

For each positive clone prepared in accordance with the procedures of Example 1, two separate PCR™ reactions were carried out under the following conditions:

Set I PCR™ primer: M13-20 sequencing primer; oligonucleotide A.

Set II PCR™ primer: M13 reverse primer; oligonucleotide A.

Temperature profile for PCR™:

94° C., 5 min

94° C., 1 min; 60° C., 1 min; 72° C., 2 min; 45 cycles.

72° C., 7 min

4° C., soak

Each reaction was carried out in 10 μl with 1 U of cloned Pfu™ DNA polymerase (Strategene Catalog #60015), 3% glycerol, 1× pfu Buffer #3, 200 μM dNTP, 100 ng of each primer and $10^3$ phages. PCR™ products were analyzed by electrophoresis in 1% Agarose, 2% Nusieve GTG Agarose (FMC, Rockland, Md.) and 1× TAE buffer. Clones with a single amplification product were identified and further characterized by DNA sequencing.

PCR™ products were excised from agarose gels and purified with QIAEX™ extraction kit (Qiagen, Chatsworth, Calif.). Double-stranded linear DNA sequencing was performed using previously-described methods (Ali and Vedeckis, 1987; Amero et al., 1992). [α-$^{32}$P]dCTP was used as the radioisotope and autoradiography was performed on dried gels with Kodak X-OMAT AR film at room temperature overnight.

Double-stranded plasmids (recovered pBluescript® clones) were used as templates for DNA sequencing according to previously described procedures (Anderegg et al., 1988). [α-$^{35}$S]dCTP was used and autoradiographywas done at room temperature overnight with Hyperpaper® Amersham, Arlington Heights, Ill.).

The cDNA nucleotide and deduced amino acid sequences of hUR and rURs are shown in FIG. 1C and FIG. 1D, respectively. Optimized DNA sequence alignment analysis of hUR and rUR is shown in FIG. 10.1 and FIG. 10.2. Also shown in this illustration are the deduced amino acid sequences for both rUR and hUR polypeptides.

EXAMPLE 3

IN VITRO TRANSCRIPTION/TRANSLATION OF RAT UR-cDNA AND EXPRESSION OF TrpE-rUR GENE FUSION

Clone R6.2 was cut with HindIII, transcribed in vitro with $T_7$ RNA polymerase, and the RNA made was then translated in a rabbit reticulocyte lysate system (Promega) using [$^{35}$S]-methonine. 10 μl of the lysate was loaded and analyzed by 7.5% SDS-PAGE. The gel was dried after incubated with 1M sodium salicylate (pH 7), for 30 min and exposed to Kodak X-OMAT AR film at −80° C. overnight. The results indicated that the molecular weight of the radioactive protein was about 55 kDa, which was consistent with the expected valve from the deduced amino acid sequence of rUR.

Two oligo primers were constructed:
Oligo-R6.2ATG2:

5'-GCC TGG AAC GAG GAT CCT GAA GGA ACC ACC ATG
TCT TCC CCC ACA AGT-3'          (SEQ ID NO:18)

(Underlined sequence is rabbit α-globin sequence upstream of the 5'-end of the initiation codon. [Kozak, 1987]).
Oligo-R6.2NcoII:

5'-ACA GGC ATA GCG CCC GGC CCC ACC ATG GAC CAC
CGT-3'          (SEQ ID NO:19)

PCR™ was performed with above primers and the R6.2 clone as a template. An about 400-bp fragment was recovered from agarose gels using a QIAEX® (Qiagen) kit and digested with NcoI and BarnHI. The R6.2 clone in pBluescript® was also digested with NcoI and BamHI and the larger fragment was ligated to the PCR™ fragment purified from agarose gel electrophoresis. The reconstructed clone, named R6.2ATG2 was cut with BamHI and HindIII and cloned into PATH2 (Koerner, et al., 1987) vector through its multiple cloning site, giving PATH2/R6.2ATG2. The final gene fusion junction (beginning with the start codon of 322 of E. coli anthranilate synthase) was:

GAG ATC CCC GGG GAT CCT GAA GGA ACC ACC ATG
TCT TCC CCC          (SEQ ID NO:20)

The gene fusion codes for 331 amino acids of TrpE at the amino terminus which was followed by the entire rat UR amino acid sequence. The induction of the fusion gene was carried out in accordance with previously described procedures (Ausubel et al., 1990) with some modifications. In brief, E. coli RR1 was transfected with PATH2/R6.2ATG2 and plated on LB medium containing amp and tryptophan. A single colony was used to inoculate 50 ml 2× TY medium with Amp and 20 μg/ml tryptophan. The culture was grown for 10 h at 37° C. with shaking until the $OD_{600}$ was 1.0. The cells were centrifuged, suspended in M9 medium and added to four flasks each containing one liter of supplemented M9 medium. The culture was grown at 37° C. with vigorous shaking until $OD_{600}$ reached 0.7. Indolacetic acid was then added to the culture to a final concentration of 10 μg/ml. The culture was grown for an additional 3 h and then kept in a cold room overnight. The isolation of the fusion proteins was performed with modifications of the method previously described (Ausubel et al., 1990). In brief, 1 l of cells were pelleted by centrifugation, washed with PBS (10 mM $NaH_2PO_4$ [pH 7.5] and 150 mM NaCl) and suspended in 200 ml Buffer I (50 mM Tris-HCl [pH 7.5], 5 mM EDTA, and 3 mg/ml lysozyme). The suspension was kept on ice for 2 h, then NaCl and NP-40™ (Non-idet P-40) were added to a final concentration of 0.3M and 0.65% (vol/vol), respectively. The viscous suspension was sonicated and centrifuged at approximately 10,000× g for 10 min at 4° C. The pellet, which contained most of the fusion protein, was washed once with 10 mM Tris-HCl (pH 7.5) containing 1M NaCl, then once with 10 mM Tris-HCl (pH 7.5), and finally resuspended in 1 ml 10 mM Tris-HCl (pH 7.5). The fusion protein was used as an immunogen to generate antibodies (See Example 20 for details of this aspect of the present invention).

EXAMPLE 4

TISSUE DISTRIBUTION OF UR-mRNA

The presence of UR mRNA in different organs of rat was analyzed by Northern analysis. Total RNA from different rat tissues or cultured cells was isolated by a standard guanidine chloride/phenol extraction method, from which poly-A RNA was isolated through oligo(dT)-cellulose type 7 (Pharmacia). RNA electrophoresis was carried out with formaldehyde followed by capillary transfer to Zeta-Probe™ nylon membranes (Bio-Rad, Hercules, Calif.). A 1.6-kb rat clone was the template for generating probes using a MultiPrime® random priming kit (Amersham, Arlington Heights, Ill.). The efficiency of the labeling reaction was approximately $4 \times 10^{10}$ cpm incorporated per μg of template. The hybridization buffer contained 0.5M sodium phosphate, 7% SDS (wt/vol), 1% BSA (wt/vol), and 1 mM EDTA (Mahmoudi and Lin, 1989). Prehybridization was carried out in hybridization buffer at 65° C. for 2 h and $^{32}$P-labeled probe was added and incubation continued overnight. The filters were washed in Buffer A (40 mM sodium phosphate [pH 7.2], 5% SDS [wt/vol], 0.5% BSA [wt/vol], and 1 mM EDTA) at 65° C. for 1 h and then in Buffer B (40 mM sodium phosphate [pH 7.2], 1% SDS [wt/vol], and 1 mM EDTA) at 65° C. for 20 min. The filters were air-dried and exposed to Kodak X-OMAT AR film at −80° C. with intensifying screens.

The results indicated that UR mRNA was present in numerous organs, including ventral prostate, seminal vesicle, testis, vagina, uterus, kidney, adrenal, liver, spleen, brain and heart. UR, therefore, may be considered a ubiquitous receptor. Among the human prostate cell lines, UR-mRNA level in the androgen-insensitive metastatic PC-3 cells was much higher than that in the androgen-sensitive nonmetastic LNCaP cells, suggesting that UR-gene expression is likely regulated by hormones or other factors and may play important roles in the control of cellular functions.

EXAMPLE 5

IMMUNOLOCALIZATION OF DR IN VARIOUS TISSUES

Tissues were removed from 200- to 300-g Sprague-Dawley rats, immediately frozen in liquid nitrogen and stored at −135° C. Frozen human prostatic tissue and skin samples were obtained through the National Disease Research Interchange (Philadelphia, Pa.). Frozen tissues were embedded in Tissue-Tek O.C.T. compound (Miles, Elkhart, Ind.) and about 6- to about 8-µm sections were cut using a cryostat at −20° C. Sections were placed on gelatin-coated slides, air-dried for 3 min and then fixed in picric acid-formaldehyde for 10 min. Fixed tissue sections were washed in PBS (10 mM NaH$_2$PO$_4$ [pH 7.5], and 150 mM NaCl), and blocked with PBS containing 10% normal goat serum. Specificity of immunocytochemical staining was determined using purified rabbit IgG or antibody to 5α-reductase preincubated for 18 h at 4° C. with the purified TrpC-5α-reductase fusion protein. Bound antibody was detected by incubating tissue sections with biotinylated goat anti-rabbit IgG (Zymed, Co. San Francisco, Calif.) (5 µg/ml in PBS containing 1% normal goat serum) for 10 min at room temperature and then with horseradish peroxidase-conjugated streptavidin (Zymed) at a dilution of 1:100 for 5 min at room temperature. Peroxidase was visualized by incubating sections with 1.4 mM diaminobenzidine, 0.01% (vol/vol) H$_2$O$_2$ in 50 mM Tris-HCl (pH 7.2), for about 2 to about 5 min at room temperature. Slides were rinsed in water, dehydrated in ethanol, cleared in xylene, and mounted with a liquid coverslip.

All tissue samples taken from organs that were analyzed for the UR-mRNA level (including, seminal vesicles, liver, vagina, uterus, kidney) showed the presence of a nuclear stain indicating that UR is a nuclear protein. The epithelium cells but not the stroma or basal cells showed distinct UR stain in the cell nuclei.

Affinity-purified anti-peptide antibodies were used to study the immunocytochemical localization of UR in various rat and human tissues and cultured cells (FIG. 8A, FIG. 8B, FIG. 8C, and FIG. 8D). UR was detected in the nuclei of cells in numerous rat tissues including brain, kidney, testis, ventral prostate, epididymis, seminal vesicle, liver, vagina, uterus, and ovary. Epithelial cells but not stromal or basal cells showed distinct UR staining of nuclei. In general, fibroblasts of skin contained little or no detectable UR. UR was detected in human prostate and breast epithelia and in the following cell lines: HeLa, PC-3, LNCaP, MCF-7, SCC 13, and A431. The amount of UR mRNA in androgen-insensitive metastatic PC-3 cells was several times higher than that in androgen-sensitive nonmetastatic LNCaP cells; whether this difference is related to the androgen-sensitivity of these cells remains to be established. Antibodies detected a 50-kDa antigen on Western blots of cell extracts from COS-1 cells transiently transfected with a UR expression vector or from rat 1A cells infected with a retroviral expression vector. A 50-kDa antigen was also detected in high salt extracts of nuclei from various rat tissues.

EXAMPLE 6

ISOLATION OF UR cDNA cDNA libraries were constructed in the Lambda ZAP™ II vector from mRNA isolated from the vagina of adult female Sprague-Dawley rats and from human prostate cancer PC-3 cells. Libraries were screened with several synthetic $^{32}$P end-labeled oligonucleotides derived from sequences in the conserved DNA-binding region of nuclear receptors. Positive clones were screened further by PCR™ using primers from sequences within the DBD. Clones with single amplified bands were identified and the amplified DNA fragments were further analyzed by DNA sequencing. With this procedure cDNAs were obtained that encoded a putative full-length rUR. rUR cDNA encodes a protein with 443 amino acid residues with a calculated $M_r$ of about 50 kDa.

FIG. 2 is a comparison of the overall structure of rUR with some of the known nuclear receptor sequences that have high homology with rUR. The most closely related receptor is the ecdysone receptor (EcR) of Drosophila. EcR and UR have 82 and 56% amino acid identity in two regions of DBD, 40% in the hinge segment, and 46% in a small segment of LBD. The homology between fUR and other known receptors are considerably lower. A partial cDNA for hUR has been isolated and sequenced.

EXAMPLE 7

RELATIONSHIP OF UR TO OTHER NUCLEAR RECEPTORS

To identify the historical relationship of UR to other members of the nuclear receptor family, receptor sequences were analyzed by the "Unweighted Pair Group Method" (Nei, 1987). To construct the UPGM tree a pairwise position by position comparison of all of the sequences was performed to determine whether or not the sequences were identical at that position. This method clusters the two most similar sequences and calculates the average similarity of these two sequences to every other sequence. The DBD & CBD sequences were employed for this purpose.

Figure 3A:
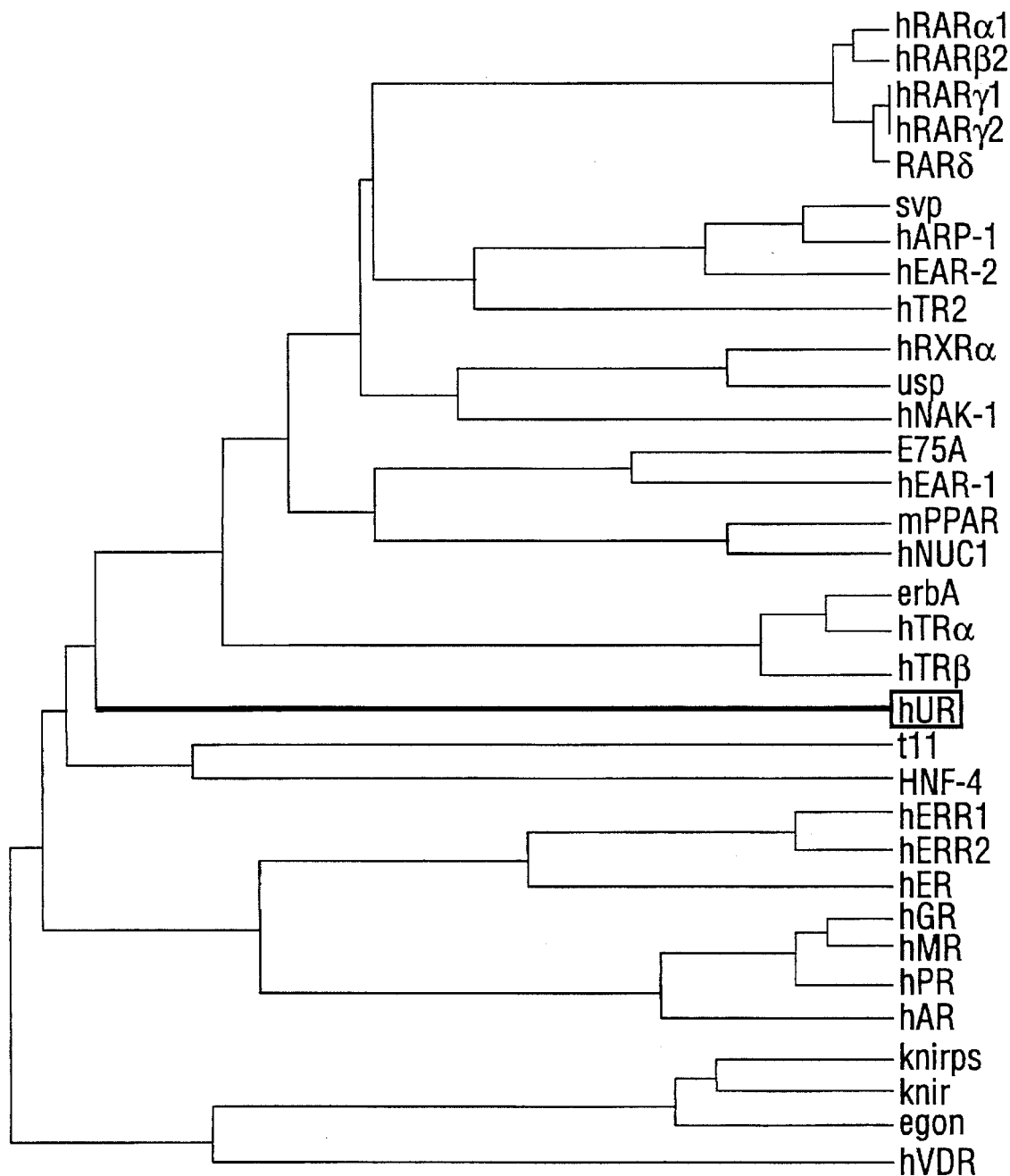
FIG. 3A. Evolutionary relationships of nuclear receptors by alignment of DNA-binding domain using Unweighted Pair Group analyses.
Figure 3B:
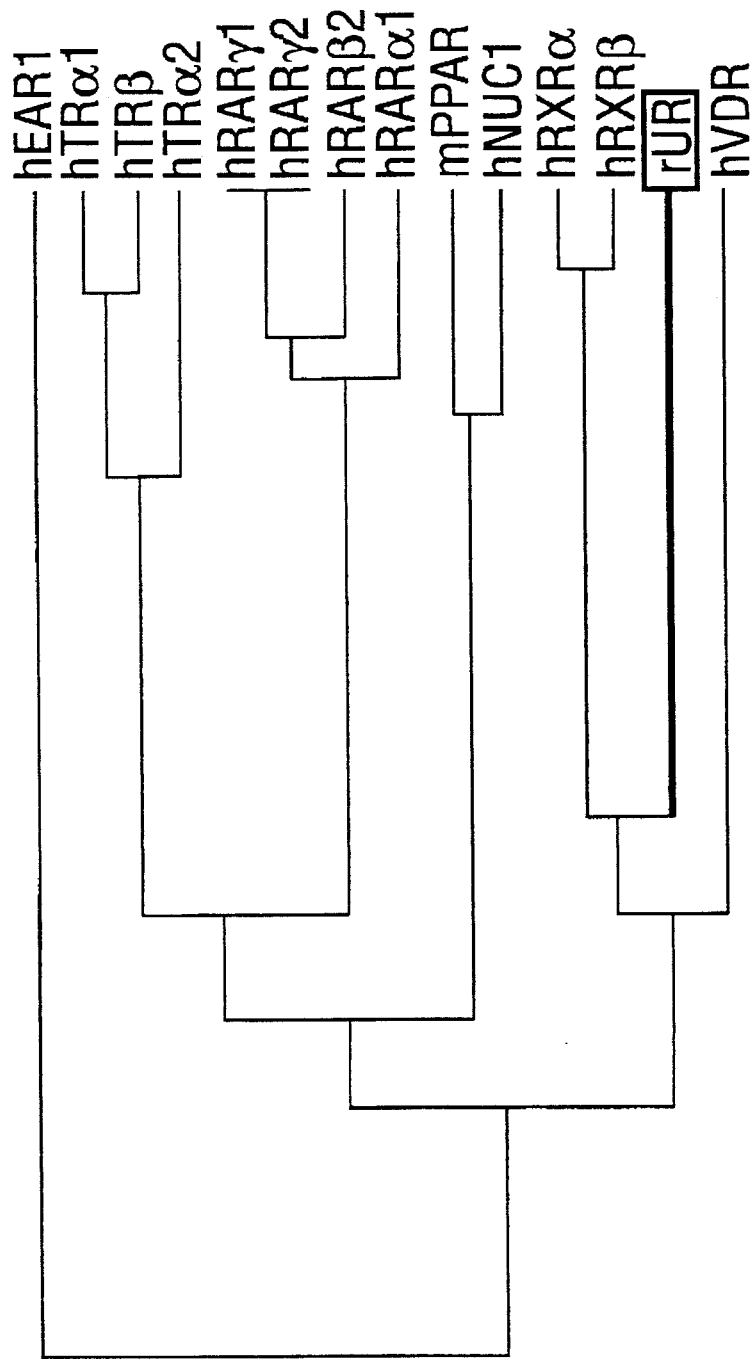
FIG. 3B. Evolutionary relationships of nuclear receptors by alignment of ligand-binding domain using Unweighted Pair Group analyses.

The results of these analyses are illustrated in FIG. 3A and FIG. 3B. The length of the horizontal lines connecting one sequence to another is proportional to the estimated genetic distance between sequences. The tree indicates that UR branched out from all other human or rodent nuclear receptors very early in evolution. This is consistent with the fact that overall sequence homology between UR and other human or rodent nuclear receptor family members is very low (<50%).

EXAMPLE 8

UR mRNA EXPRESSION IN VARIOUS ORGANS

The presence of UR mRNA in different rat organs and cultured cells was determined by Northern analysis of poly-A⁺ RNA. UR mRNA is present in many organs, including ventral prostate, seminal vesicle, testis, vagina, uterus, kidney, adrenal, liver, spleen, brain, and heart. UR, therefore, may be considered a ubiquitous receptor. UR mRNA level in androgen-insensitive metastatic PC-3 cells was several times higher than that in androgen-sensitive nonmetastatic LNCaP cells, suggesting that UR expression may be regulated by hormones or other factors and may play a role in the control of cellular functions.

Antibodies against UR were produced using both UR purified from bacteria expressing a TrpE-UR fusion protein, and synthetic peptides derived from the hinge region and N- and C-termini of UR as antigens. Affinity-purified antibodies were used to study the immunocytochemical localization of UR in various rat and human organs and cultured cells.

UR was detected in the nuclei of cells in numerous rat tissues including brain, kidney, testis, ventral prostate, epididymis, seminal vesicle, liver, vagina, uterus, ovary. Epithelial cells but not stromal or basal cells showed distinct UR-staining of nuclei. In general, fibroblasts of skin contained little or no detectable UR. UR was also detected in human prostate and breast epithelia. High levels of UR were also detected in the following cell lines: HeLa, PC-3, LNCaP, MCF-7, SCC 13, and A431.

EXAMPLE 9

EFFECT OF UR EXPRESSION ON GENE TRANSACTIVATION

Figure 5A:
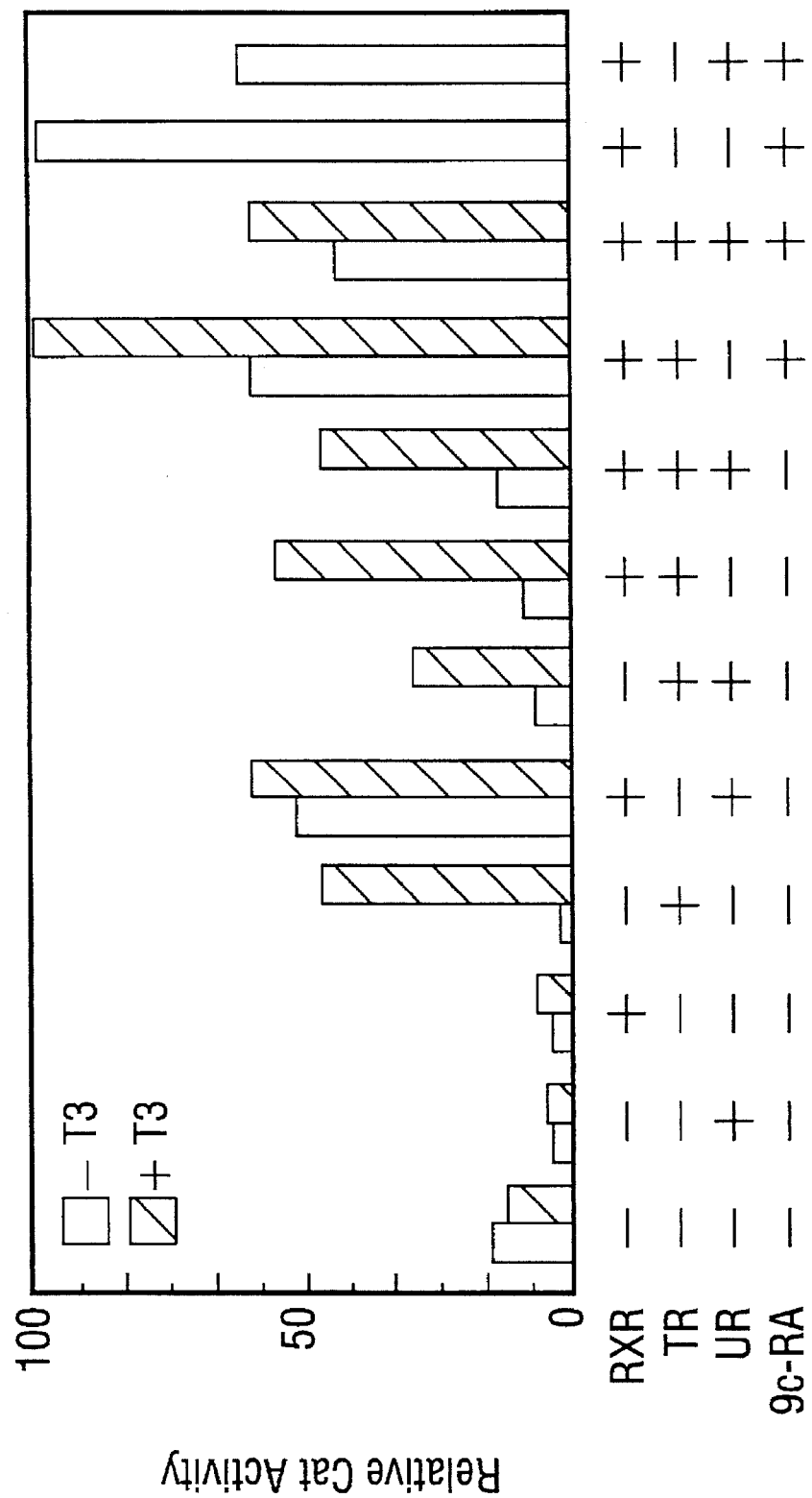
FIG. 5A. rUR modulation of hRXRα, hRARα, and hTRβ-dependent transactivation of reporter genes. Transcriptional activation of a DR-4-CAT reporter plasmid in COS-1 cells by transiently expressed rUR, in combination with hRXRα and hTRβ. If indicated, 100 nM T₃ and/or 50 nM 9c-RA were used.
Figure 5B:
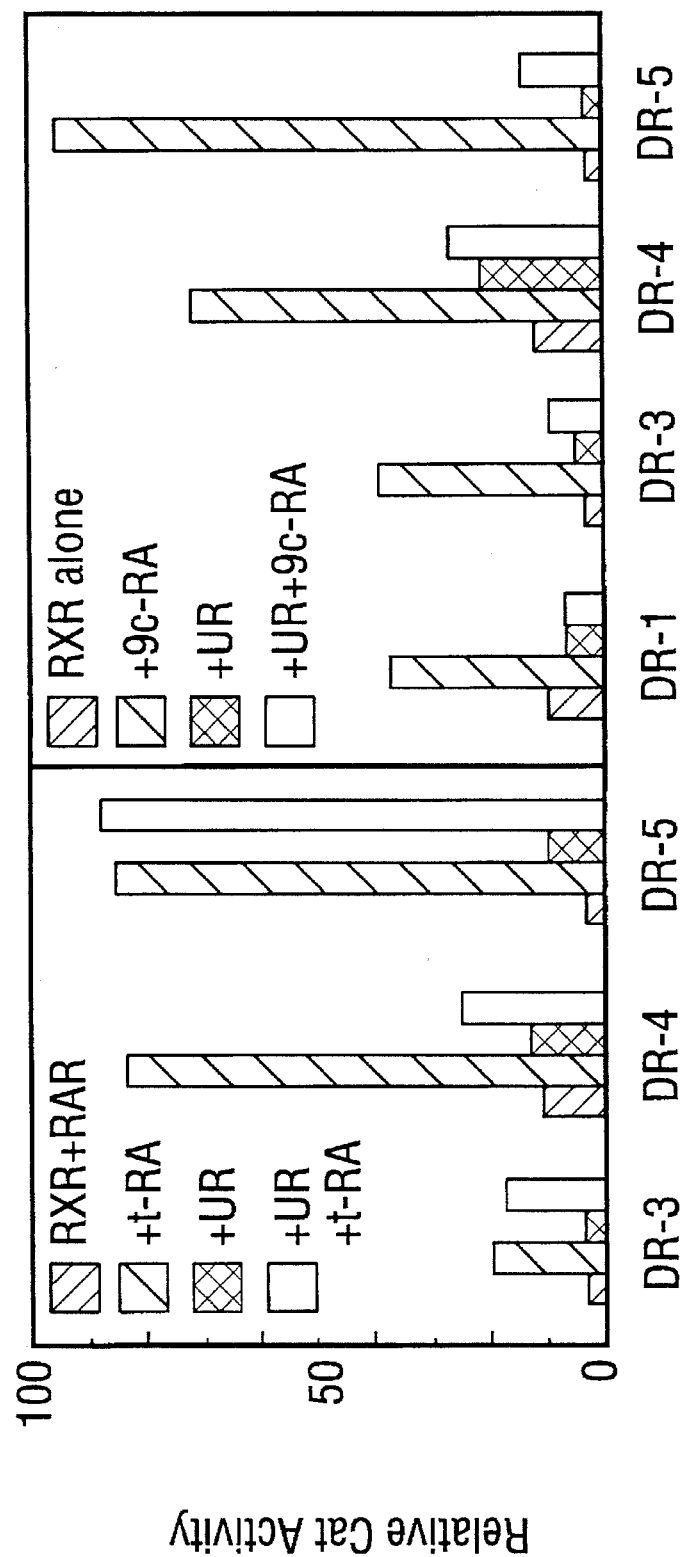
FIG. 5B. rUR modulation of hRXRα, hRARα, and hTRβ-dependent transactivation of reporter genes. Selective inhibition by rUR of gene transactivation by hRXRα/hRARα heterodimer (left panel) and hRXRα homodimer (right panel) in COS-1 cells. If indicated, 1 mM t-RA or 50 nM 9c-RA were used.

The effect of rUR on hTRβ and hRXRα-mediated gene transactivation was examined in COS-1 cells cotransfected with CAT reporter plasmids containing different DR elements. In the absence of exogeneous ligands, such as 9c-RA and 3,3'5'-triiodo-L-thyronine (T3), these receptors did not stimulate transactivation of a DR-4 reporter gene. In the presence of their ligands, hRXRα and hTRβ stimulated the expression of the reporter gene but this activity was partially repressed by rUR (FIG. 5A and FIG. 5B). This inhibition may be due to the ability of UR/RXR and UR/TR to compete with RXR or TR homodimers for binding to the DR-4 element. UR formed heterodimers with these receptors in gel thrift assays. UR may also compete with TR for endogenous RXR in COS-1 cells.

In the absence of T3, expression of rUR and hTRα did not stimulate CAT activity. In the absence of 9c-RA, however, the level of CAT activity in cells coexpressing rUR and hRXRα was 4- to 5-fold greater than that in COS-1 cells expressing either rUR or hRXRα alone (FIG. 5A). Whether UR function is dependent on a ligand in cells or in culture media was not clear, but it is possible that UR/RXR heterodimerization alters the LBD structure so that UR/RXR was able to bind to the response element and activates the reporter gene in the absence of a ligand.

t-RA-dependent CAT gene activation by hRARα/hRXRα was virtually abolished by coexpression of rUR in cells transfected with a DR-4 reporter plasmid but not in cells transfected with DR-3 or DR-5 reporter plasmids (FIG. 5B).

This specificity may reflect the response element-binding affinity and transactivation activity of various homo- and hetero-dimers present in the transfected cells. UR clearly is capable of producing positive or negative effects on gene expression and may participate in a mechanism that regulates TR, RAR and RXR function in cells. The ability of UR to selectively inhibit gene transactivation by RAR/RXR on select response elements is similar to the effect of the orphan receptor COUP-TF which also interacts with RXR and acts as a regulator of the retinoic acid response pathway with certain response elements.

EXAMPLE 10

SEQUENCE OF hUR AND rUR cDNAs, INTRON-EXON BOUNDARIES, AND 5'-PROMOTER SEQUENCE OF THE hUR GENE

A set of cDNAs from a rat vagina cDNA library have been isolated and sequenced to deduce the putative full-length sequence for rUR. rUR mRNA is about 2.0 to about 2.2 kb as determined by Northern hybridization analysis of mRNA performed under stringent hybridization and washing conditions from several rat tissues. These cDNA clones represent about 1.9 kb of the total mRNA. The sequence for hUR from the human prostate cancer PC3 cell cDNA library also includes portions encoding the open reading frame.

Restriction mapping of the hUR gene has been performed using a genomic library prepared from human placenta. Appropriate subclones were sequenced to determine the sequence of the 5'-promoter region and exon/intron boundaries. Sequence information was then analyzed for potential abnormalities (or mutations) in prostate cancer cells and cells from patients with abnormality in thyroid hormone or retinoic acid response.

The chromosomal location of UR has been determined. To localize the UR gene, three different genomic clones containing UR sequences, were used as probes to perform fluorescence in situ chromosomal hybridization on phytohemagglutinin-stimulated human metaphase peripheral blood lymphocytes. Biotin-labeled probes were prepared by nick-translation and hybridized probe detected with fluorescein-conjugated avidin. Chromosomes were identified by staining with 4',6-diamidino-2-phenylindole dihydrochloride, using a modification of the previously described procedure (Rowley et al., 1990). The human UR gene was localized to chromosome 19, band q13.3–13.4. Localization of the UR gene may provide some insight into the biological function of UR, if this chromosomal location may be linked to any human diseases. Other genes located in this region include the genes for located human prostate specific antigen, muscle creatine kinase, receptor for Fc fragment of IgA, ATP-dependent DNA ligase I, carcinoembryonic antigens, apolipoprotein C-I, C-II and E, cytochrome P450 subfamily IIA, IIB, and IIF, bcl-3, protein kinase Cg, luteinizing hormone b, and interleukin 11. Interestingly, an unstable CTG repeat in the 3' untranslated region of an unknown-function gene, which localized to 19q13.3 was recently found to be responsible for myotonic dystrophy. The UR gene has CTG repeats on the anti-sense strand that codes for poly-serine and poly-glutamic acid, however, the relationship of UR with myotonic dystrophy is unclear.

EXAMPLE 11

UR INTERACTION WITH SYNTHETIC HRE SEQUENCES

The UR DBD exhibits some homology to the TR DBD, and shares in common with members of the TR subfamily three amino acids in the DBD at positions which determine half-site binding specificity (Umesono and Evans, 1989). Since nuclear receptors in the TR subfamily form heterodimers with RXRs, and bind to response elements consisting of direct AGGTCA repeats separated by base pair spacings of differing length, in vitro gel-shift DNA binding assays have been utilized to study the specific DNA-binding ability of UR in the absence and presence of other receptors. In these studies, UR DBD, full-length UR, and UR/RXR heterodimers were, for example, allowed to interact with perfect direct repeats of consensus half-sites. The sequences of oligonucleotides used in the gel mobility-shift assays are described in Table 4.

It has been shown that truncated RAR with only 66 amino acid residues of the zinc finger-domain may bind to DNA in a sequence specific fashion (Yang et al., 1991). However, additional amino acids outside the zinc finger-domain of RXR are required for specific recognition of DNA sequences (Wilson et al. 1992; Lee et al., 1993). The DBD of rUR containing a few amino acids in the hinge region (rUR amino acid residues 72 to.168) was expressed as a fusion protein using the *E. coli* expression vector PET15β and purified by affinity chromatography.

Figure 4:
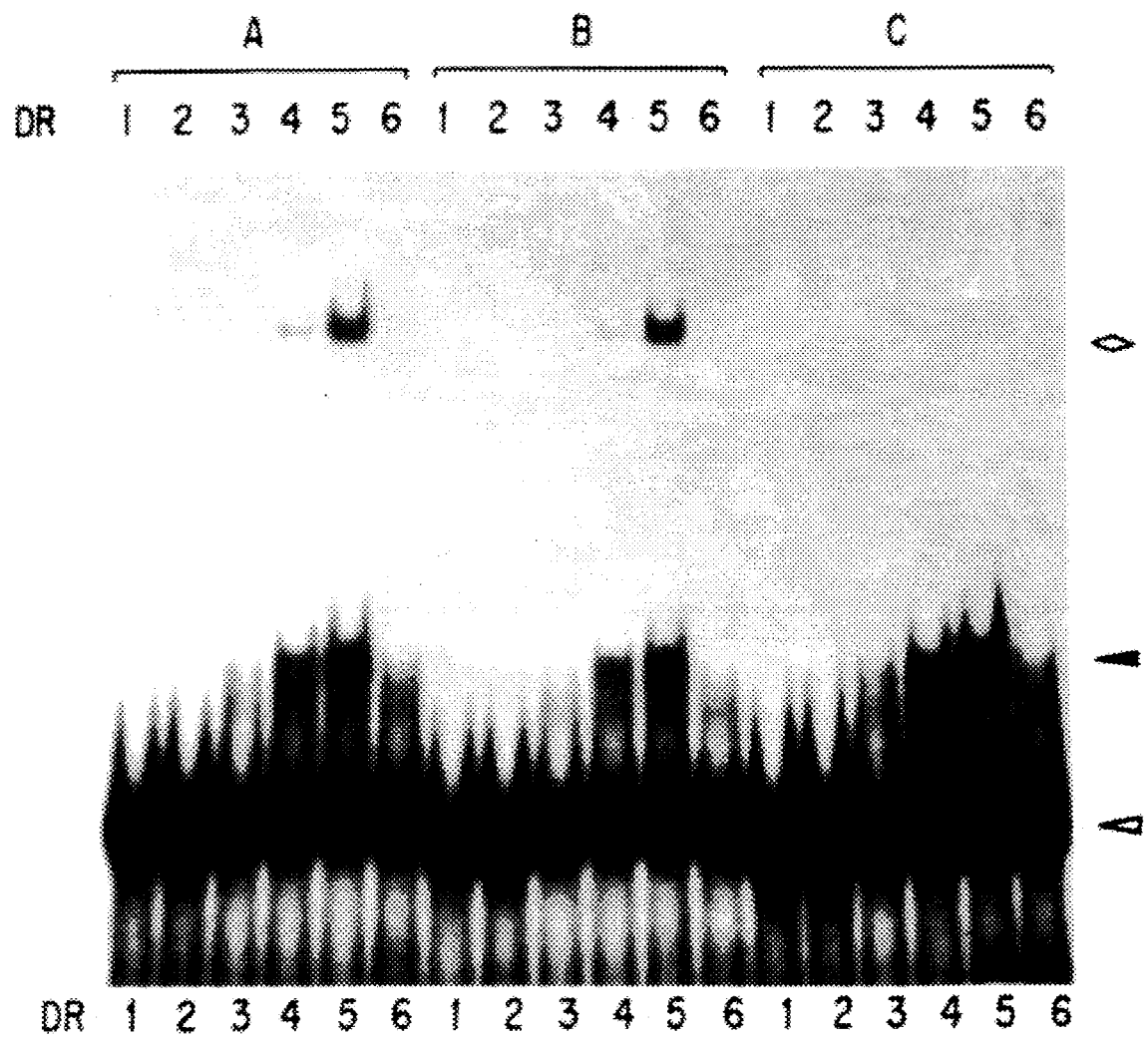
FIG. 4. Interaction of UR-DBD with oligonucleotides DR0–DR6 using a gel-shift assay. UR-DBD may bind to all oligonucleotides (DR0–DR6) as monomers. Homodimer binding to oligonucleotides was best with DR4 and DR5. Homodimer-DNA complexes were not observed without UR-DBD. Only homodimers bound to DNA were supershifted by a hinge-region antibody. Free probe ran off the gel.

The DNA-binding ability of this domain was tested by gel-shift analyses with a set of oligonucleotides that contained AGGTCA direct repeats with 0 to 6 oligonucleotide spacing (shown above). Results suggest that this UR fusion protein binds to all these direct repeats, probably as monomer, and optimum spacing for homodimer binding is 5 nucleotides, which is identical to a Retinoic Acid Receptor response Element (RARE) (FIG. 4).

erodimers and that rUR may form heterodimers with hTRβ1 and hTRα1. Antibodies against the N-terminus of rUR super-shifted rUR/hRXRα heterodimers without reducing the total amount of rUR bound to DR-4.

EXAMPLE 12

REPORTER GENE EXPRESSION IN UR-TRANSFECTED CELLS

To investigate the role of DR in intact cells in transactivation of genes, COS-1 cells were employed in a number of studies for transient transfection. For this purpose, rUR, hRARα, and hRXRα were inserted into the pSG5 expression vector (Stratagene), while human TRα$_1$ and TRβ$_1$ cDNAs were inserted into pCDM8 (Invitrogen, San Diego, Calif.). (See Example 17 for a detailed description of techniques which are used in the construction of expression vectors and reporter plasmids). The 4×DR-4 response elements were inserted into HindIII-digested Δ56-c-fos CAT plasmid (Gilman et al., 1986). Receptor expression vectors (4 µg) were cotransfected in duplicate plates alone or in combination with 8 µg of Δ56-c-fos CAT reporter plasmid containing 4×DR-4 response elements and 4 µg of pCH110 vector (Pharmacia) to provide β-Gal activity for normalization of transfection efficiency.

TABLE 4

| | | |
|---|---|---|
| DR-0: | 5'-GATCCTCAGGTCAAGGTCAGAagct-3' | (SEQ ID NO: 23) |
| | 3'-ctagGAGTCCAGTTCCAGTCTTCGA-5' | (SEQ ID NO: 24) |
| DR-1: | 5'-GATCCTCAGGTCAGAGGTCAGAagct-3' | (SEQ ID NO: 25) |
| | 3'-ctagGAGTCCAGTCTCCAGTCTTCGA-5' | (SEQ ID NO: 26) |
| DR-2: | 5'-GATCCTCAGGTCAAGAGGTCAGAagct-3' | (SEQ ID NO: 27) |
| | 3'-ctagGAGTCCAGTTCTCCAGTCTTCGA-5' | (SEQ ID NO: 28) |
| DR-3: | 5'-GATCCTCAGGTCAAGGAGGTCAGAagct-3' | (SEQ ID NO: 29) |
| | 3'-ctagGAGTCCAGTTCCTCCAGTCTTCGA-5' | (SEQ ID NO: 30) |
| DR-4: | 5'-GATCCTCAGGTCACAGGAGGTCAGAagct-3' | (SEQ ID NO: 31) |
| | 3'-ctagGAGTCCAGTGTCCTCCAGTCTTCGA-5' | (SEQ ID NO: 32) |
| DR-5: | 5'-GATCCTCAGGTCACCAGGAGGTCAGAagct-3' | (SEQ ID NO: 33) |
| | 3'-ctagGAGTCCAGTGGTCCTCCAGTCTTCGA-5' | (SEQ ID NO: 34) |
| DR-6: | 5'-GATCCTCAGGTCACCAAGGAGGTCAGAagct-3' | (SEQ ID NO: 35) |
| | 3'-ctagGAGTCCAGTGGTTCCTCCAGTCTTCGA-5' | (SEQ ID NO: 36) |

In contrast, full-length rUR bound to all direct repeats from DR-0 to DR-6 with similar affinity mainly as homodimers and a small amount as monomer. hRXRα enhanced rUR binding to all direct repeats by heterodimerization, but with highest affinity to DR-4, a thyroid hormone response element. Both rUR homodimer and hRXRα/rUR heterodimer may bind to TREpal, but less strongly than to DR-4. This result is similar to the behavior of RAR/RXR heterodimers, which bind to DR-5 more strongly than to TREpal.

A rabbit polyclonal antibody against UR (C-terminal epitope) super-shifted dimers but significantly inhibited the formation of rUR heterodimers bound to DR-4. A heptad repeat leucine zipper structure in the C-terminal LBD of rUR, which is believed to be important in heterodimerization of other nuclear receptors, may be involved in UR heterodimerization and the C-terminus antibody may have blocked this process. Inhibition of homodimer formation and heterodimer formation between DR and RXR indicate that the carboxyl-terminal of UR may be important for heterodimerization. This is in agreement with the fact that RXR heterodimerization involves the carboxyl-terminal residues of receptors (Kliewer et al., 1992; Leid et al., 1992; Marks et al., 1992).

Data also indicate that binding of hRXRα/rUR heterodimers to DR-4 is stronger than hRXRα/hTRs het- The day after transfection, T3 was added (100 nM) to appropriate plates. 30 h later, cells were collected by scraping and subjected to 3 freeze-thaw cycles. Aliquots of cytosolic extracts normalized for β-Gal activity were used in 2 h CAT assays. Acetylated $^{14}$C-Cml was separated from non-acetylated reactant by thin layer chromatography and quantitated using an AMBIS radioanalytic imaging system (AMBIS Systems, San Diego, Calif.).

Studies have shown that UR alone in the presence or absence of T3 was not effective in transactivating the DR-4-linked reporter gene (FIG. 5A and FIG. 5B). Surprisingly, UR in combination with RXRα activated DR-4-driven CAT gene expression in a T3-independent manner. In cells transfected with TR, T3-dependent CAT gene expression was inhibited by UR. These findings strongly indicate the importance of UR in the mechanism that regulates TR and RXR function in cells. It is not possible to clearly suggest a molecular mechanism for this unusual relationship, but UR clearly is capable of interacting with or forming heterodimers to produce positive or negative effects on gene expression. Considering the fact that the C-terminal antibodies may inhibit UR/RXR heterodimer formation in gel-shift assays, the HBD of UR is probably involved in this mechanism. UR mutants are used in determining domain involvement.

Additional reporter plasmids containing DR-0 through DR-3, DR-5, DR-6 and TREpal response elements are constructed for these studies. As noted above, UR homodimers may bind to DR-0 through DR-6 synthetic HREs in vitro with equal affinity; perhaps cell transfection studies will reveal a transcription activation function of UR homodimers on an element other than DR-4, similar to RXR homodimer activation through DR-1 (Mangelsdorf et al., 1991). Anti-UR antibodies have been used that recognize different epitopes of UR (and different nuclear receptors) to systematically analyze in vitro interactions of these receptors and their binding to different HREs. (Anti-PR antibodies to a specific epitope of PR have been shown to induce a PR conformational change and enhance binding of PR to DNA presumably by enhancement of PR dimerization [Allan et al., 1992]). In addition to using the simple, synthetic direct repeat response elements described above, "natural" HREs may be inserted upstream of the CAT reporter gene to examine the effect of UR on an HRE in the context of interactions with other transcription factors and their proximal binding sites. Examples of such natural HREs are the MHC-L, —S, —D, —N TREs and the HREs found in the malic enzyme and RARβ promoters and in the MLV-LTR (Umesono et al., 1991).

EXAMPLE 13

UR FUNCTION IN UR-CONTAINING, RETROVIRUS-INFECTED CELLS

A most striking example of the differentiation effects of RA is provided by the embryonal carcinoma cell system. F-9 cells derived from mouse embryonal carcinoma cells (De Luca, 1991) respond to RA by differentiating into primitive endoderm tissue which progresses to become visceral endoderm. This progression is characterized by an increase in the expression of genes for α-fetoprotein and apolipoprotein E, laminin, keratin K8 and K18, and several other proteins. RA also profoundly affects formation and interaction of F9 cells and fibroblast cell lines with extracellular matrix and thus influences cell interaction with basement membrane and eventually differentiation pathways. Since it has been found by western analysis and immunocytochemical studies that F-9 cells and fibroblasts have low levels of UR expression, they may be ideal for studying UR function. Immunochemical and biochemical assays for these protein markers have been employed in a number of studies.

High titer retrovirus expressing rUR (or mouse UR) gene will be used to infect F9 and fibroblast cell lines. Infected cells will be assessed for UR expression. A comparison may be made between cells infected with MV7-rUR and control MV7 retrovirus in the appearance of RA-induced differentiation markers. Those lines expressing high level UR will also be used for detection of UR-induced or repressed genes in comparison with control MV7-infected F9 cells using the differential RNA display method (Liang and Pardee, 1992) ('RNA map' by GenHunter Corp., Brookline, Mass.; see Example 17). This method is a rapid, reproducible method of screening and comparing mRNA populations of two or more cell types. The differentially expressed fragments may be isolated, subcloned and sequenced. By this method, genes which are positively or negatively regulated through a network involving UR may be identified. cDNA fragments isolated by this procedure may be used as probes for the isolation of full length UR-regulated cDNAs from cDNA libraries and upstream regulatory sequences from genomic libraries. This represents one of the best methods for obtaining authentic and natural response elements recognized by the UR protein. The differential RNA display method would not discriminate, however, between genes which are directly regulated by UR and those which are indirectly regulated by UR.

By comparing UR-regulated gene expression in different cell types under different hormonal environments (including steroids, T3, retinoic acid, serum factors, growth factors, etc.), it may be possible to find an unique relationship among UR, other nuclear receptors, and specific genes.

EXAMPLE 14

STRUCTURE-FUNCTION ANALYSIS OF UR

Figure 6:
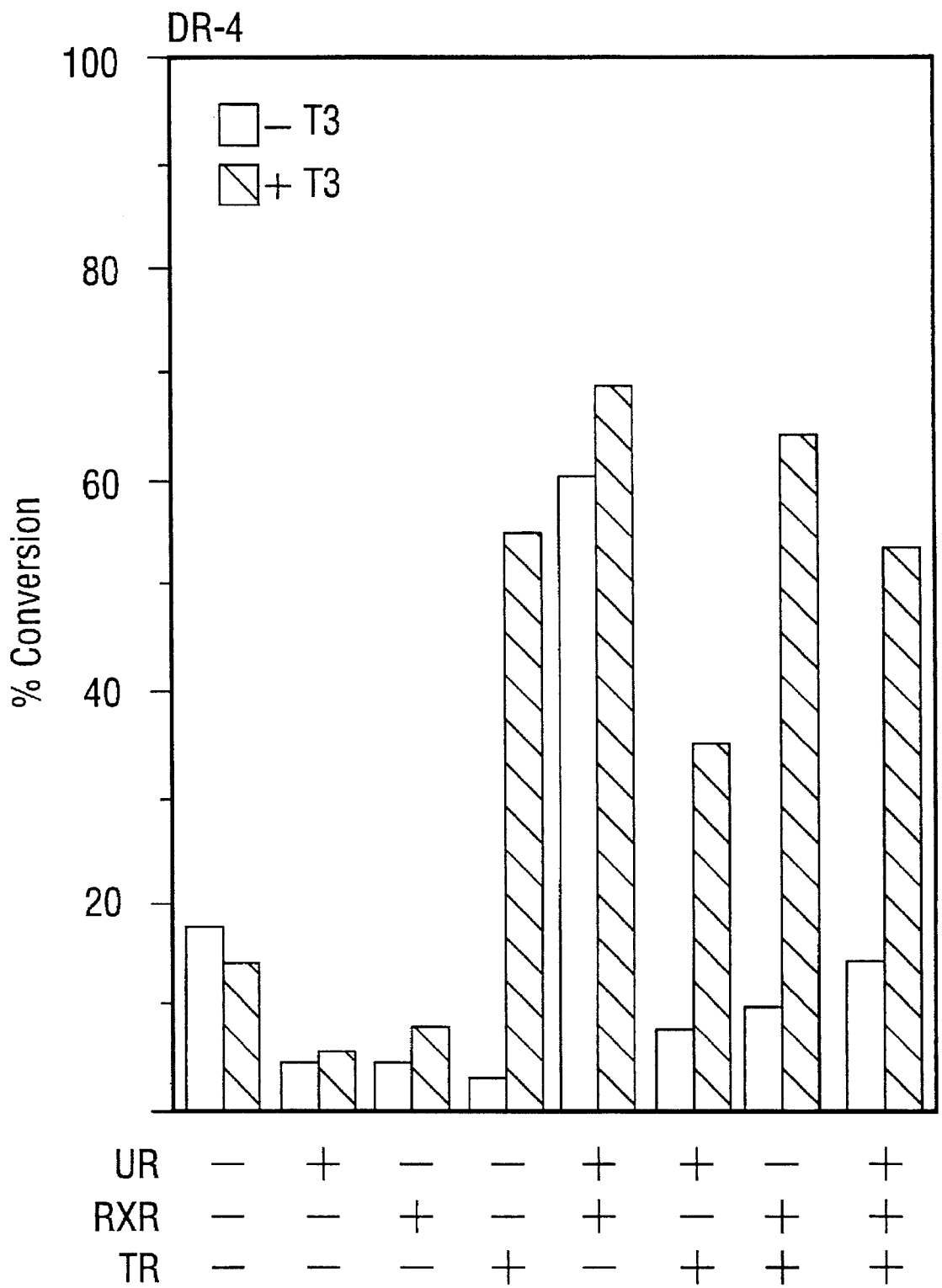
FIG. 6. Effects of co-transfection of rUR, hRXRα and hTRβ expression vectors with a 4×DR4 Δ56-c-fos CAT reporter plasmid into COS-1 cells. Cells were incubated in the absence or presence of 100 nM T3 for 30 h.
Figure 8A:
FIG. 8A. Immunocytochemical localization of UR. Cells and fixed tissue sections were incubated with affinity-purified antibodies. Bound antibodies were detected by incubating tissue sections with biotinylated goat anti-rabbit IgG and then with horseradish peroxidase-conjugated streptavidin. Peroxidase was visualized by diaminobenzidine and $H_2O_2$. UR protein is detected mainly in the nuclei of E18 mouse embryonic cells. Sections were stained with P-antibodies and X and Y with F-antibodies. Shown is a frozen-section of a rat ovary, having a secondary follicle.
Figure 8B:
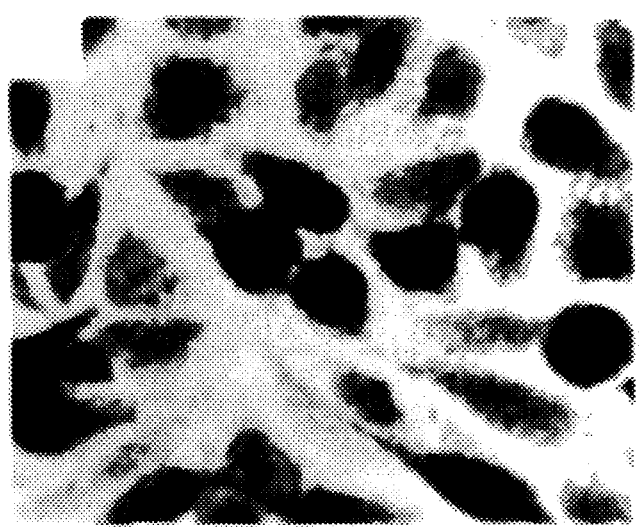
FIG. 8B. Immunocytochemical localization of UR. Cells and fixed tissue sections were incubated and detection performed as described in the legend to FIG. 8A. Shown is a transverse frozen-section of a rat epididymis.
Figure 8C:
FIG. 8C. Immunocytochemical localization of UR. Cells and fixed tissue sections were incubated and detection performed as described in the legend to FIG. 8A. Shown are PC-3 cells.
Figure 8D:
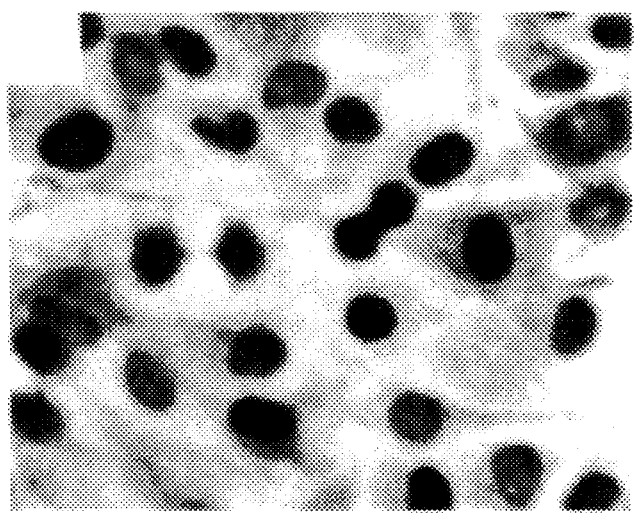
FIG. 8D. Immunocytochemical localization of UR. Cells and fixed tissue sections were incubated and detection performed as described in the legend to FIG. 8A. Shown are rat 1A cells infected with retrovirus MV7/rUR.

It has been found that UR expressed with RXR in COS cells may activate gene expression on a DR4 thyroid response element (a direct repeat separated by 4 nucleotides), and this transactivation is independent of T3 (FIG. 6). Other UR-rich and UR-poor cell lines, including fibroblasts and others identified through immunocytochemical localization studies of organs and embryos, may also be used to determine whether these phenomena are cell line-dependent. From these studies appropriate cell lines are selected for studying: (a) the involvement of different receptor domains and possible involvement of other factors regulating domain function; (b) UR-associated factors by protein-interaction screening of expression libraries; and (c) ligands for UR.

The ligand-binding domain of many nuclear receptors appears to have a peptide region that in the absence of a ligand inhibits transactivation (Forman and Samuels, 1990). This inhibition may be abolished by receptor binding of a specific ligand. When the ligand-binding property of the receptor is abolished by removing a part of the ligand-binding domain (especially a short sequence of the carboxy-terminal segment), the receptor exhibits an inhibitory effect even in the presence of the ligand. If the whole ligand-binding domain is deleted, the mutant receptor becomes ligand-independent and is constitutively active. The same strategy may be used to make deletion mutants of UR and test their ability to transactivate (with RXR) or inhibit (TR-mediated) DR-4-driven transcription. The possibility exits that UR requires a ligand for transactivation. Similarly, the presence of transcription activation factors (TAFs) that may recognize individual domains may be predicted.

Figure 9:
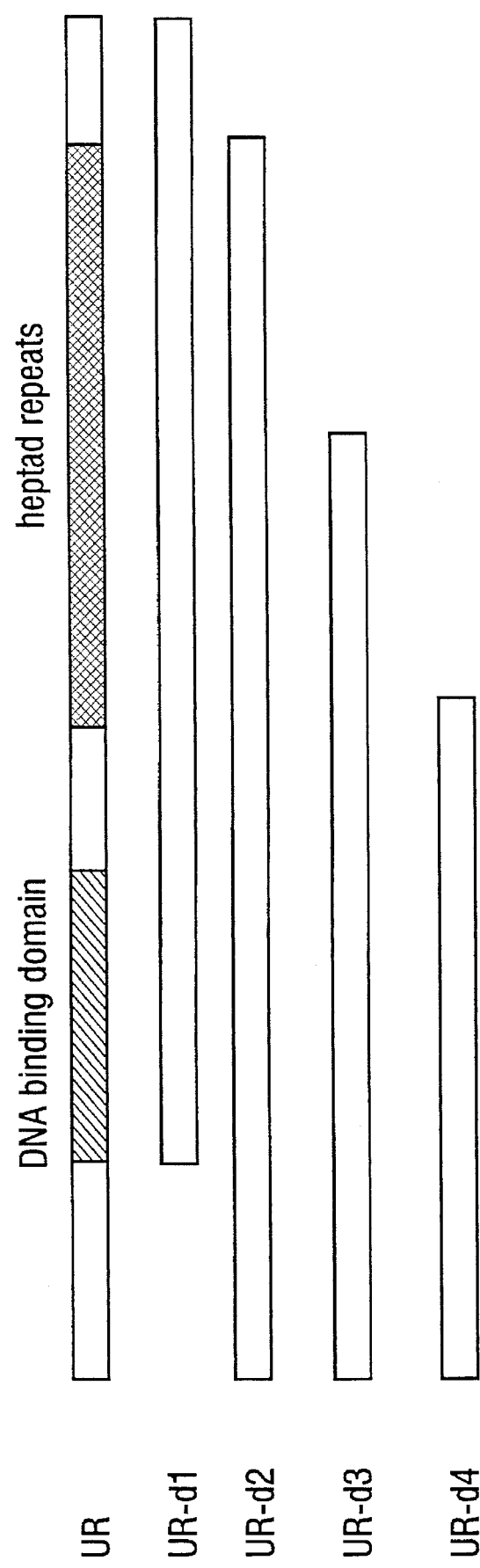
FIG. 9. Schematic summary of construction of deletion mutants of UR.

Deletion mutants have been employed to study the overall effect of domain deletion. For more detailed studies, smaller regions have been deleted, and individual amino acids have been replaced to determine their importance in the transcriptional activity of UR (FIG. 9). These mutants are also useful in studies of cellular localization signals of UR and their role in the transcriptional activity of UR and in other studies of UR, such as the role of specific amino acid phosphorylation in UR function. It is important to realize that amino acid deletion (or replacement) may induce gross changes in the secondary and tertiary structure of a protein and this change may be responsible for the observed effects.

Introduction and/or expression into cells of DNA encoding domains of UR may be helpful in the study of domain functions and identification of DNA- or receptor-binding transcription factors. Chimeric receptors may be constructed so that a domain of a well-studied steroid receptor (GR, AR, or PR) is replaced with a corresponding domain of UR. Transactivation of a reporter gene (CAT) with appropriate HRE, such as MMTV promoter, may be used to study the functions of normal and mutated UR domains. Many of the techniques used for steroid receptors are well-known to those of skill in the art.

Previously it was suggested that intracellular recycling of androgen receptor (AR) plays important roles in androgen action in prostate cells (Liao et al., 1989; Liao et al., 1965;

Liao et al., 1980; Liao et al., 1972). The regulation of the distribution of transcription factors between the cytoplasm and nucleus is a potentially-powerful way to control gene transcription. Many nuclear proteins contain one or more short amino acid sequences that direct them to the nucleus. These sequences, called nuclear localization signals (NLS), have been shown by deletion analysis play a role in nuclear localization of various receptors, including GR, ER, PR, AR, and TR (Picard et al., 1990). More recently a 60-kDa protein that may specifically bind to and presumably modulate NSL of GR and TR has been isolated (LaCasse et al., 1993). In these studies $^{125}$I-labeled NLS peptide was cross-linked with the NLS-binding protein in the cytosol and nuclear extract by bis-(sulfosuccininidyl) suberate.

Many of the fusion proteins containing NLS peptides may be useful for isolation of NLS binding proteins if these NLS-associated proteins have a high affinity for NLS containing fusion proteins. Insoluble fusion proteins may be useful in batch-wise isolation of binding proteins, while soluble ones may be employed in affinity-column purification of the NLS-associated proteins from cytosol and nuclear fractions of liver or kidney, which contain high levels of UR. Microsequencing of these proteins will be useful in determining their identity and their role in these and related studies.

Protein interaction screening has proven to be a powerful technique for isolating cDNAs encoding factors which physically associate with a given labeled protein probe on a nitrocellulose filter (Blanar and Rutter, 1992; Kaelin et al., 1992). It is possible that UR may not only heterodimerize with RXR but may also heterodimerize with other as yet unknown partners. In addition, factors which interact with N-terminal and C-terminal sequences may be important in the function of UR. Radioisotopically-labeled GST-UR fusion protein has been used as a probe to screen cDNA expression libraries (Carlberg et al., 1993; Carson-Jurica et al., 1990). Construction of cDNAs encoding glutathione-S-transferase-UR fusion proteins (GST-UR) using the pGEX-KG vector has also been performed (Guan and Dixon, 1991). This vector contains a peptide recognition sequence (RRASV) for cyclic AMP-dependent protein kinase from heart muscle (Carlberg et al., 1993) located between the GST leader sequence and the C-terminal UR sequence. The bacterially-expressed fusion protein may be easily purified by glutathione-Sepharose affinity chromatography and labeled to high specific activity with $^{32}$p. Uni-Zap® (Stratagene) cDNA libraries have been constructed in various cell lines for screening and other uses as well.

Two GST-UR fusion protein constructs have been made which contain: 1) N-terminal UR peptides extending from the initial ATG to a specific restriction site in or near the DNA-binding domain; and 2) a C-terminal UR peptide extending from a restriction site near the C-terminus of the DNA-binding domain to another restriction site at the C terminus of the hormone-binding domain. These two peptides cover the entire UR peptide sequence with the exception of the complete DNA-binding domain. Having an intact DNA-binding domain present is not desirable, because non-specific binding of the GST-UR protein to phage DNA may occur. After using these two probes, smaller GST-UR fusion proteins are constructed to identify proteins that may associate with specific regions in the N- and C-terminal domains of UR. cDNA libraries are also used from cells rich in UR (PC-3 cells) or over-expressing UR (UR-poor cells infected with pMV7-UR) to compare the type and amount of UR-associated proteins.

For finding a potential ligand for UR, several approaches have been utilized:

1) A chimetic receptor containing the N-terminaus and DBD of a well-studied steroid receptor (GR or AR) and HBD of UR has been used to study its ability to transactivate a reporter gene (CAT gene) in the absence and presence of potential ligands. This method has been utilized to study the ligand requirement for another orphan receptor, TR3 and the ligand specificity of a mutated AR.

2) T3-independent transactivation of UR-RXR may be used. In one study, it has been found that transactivation of a DR-4 driven CAT reporter gene by UR and RXR is serum dependent. Since RXR forms heterodimers with RAR, TR and VDR to transactivate target genes with simple response elements (DR-5, DR-4 and DR-3 in the absence of 9c-RA), it is possible that UR-RXR heterodimers may transactivate the reporter gene in the presence of the ligand for UR and not the ligand for RXR. If serum is needed for UR-RXR transactivation, the factor(s) in the serum may be extracted, fractionated, and purified. The structure of the purified factor may then be determined.

3) Yeast expression systems have been constructed to test whether UR and RXR together may transactivate a reporter gene expression bearing DR-4 response elements. It has been shown that RXR and RAR together may activate gene expression with a simple RARE DR-5 in yeast, and this activation is retinoic acid dependent (Heery et al., 1993). (See Example 17 for a detailed description of the methodology involved in setting up and using a yeast expression system.)

Many members of the steroid receptor family of transcription factors retain at least some of their functions (DNA binding, hormone binding, nuclear localization, transcriptional activation) when expressed in yeast. For example, androgen (Purvis et al., 1991), estrogen (Metzger et al., 1988), glucocorticoid (Schena and Yamamoto, 1988), progestin, retinoid (Heery et al., 1993), thyroid hormone (Privalsky et al., 1990), and vitamin D (McDonnell et al., 1990) receptors, as well as the orphan receptor NGFI-B (Wilson et al., 1991), activate gene transcription when expressed in yeast containing a reporter gene linked to a cognate hormone response element. In most cases, activation of gene transcription is enhanced by the presence of the appropriate ligand for the receptor. As an model system yeast provide a powerful genetic screening and selection system to dissect the structure-function relationships of various transcription factors without the complications of interference by other mammalian proteins that may affect receptor function. Yeast expression and reporter systems may be used to analyze three aspects of UR function: (a) determination of DNA sequences acting as response elements for gene transactivation by UR; (b) identification of other proteins (e.g., other members of the steroid receptor super family) that form complexes with UR; (c) define amino acid residues important in transcriptional activation and DNA- and ligand-binding by random mutagenesis.

Although no ligand for UR is currently known, mutation of the putative ligand-binding domain of UR may alter its function (i.e., transcriptional activation) and provide insight into whether a ligand is necessary for UR gene transactivation. Mutation may also create the need for a new ligand for transactivation of genes. In collaboration with the laboratory of S. Lindquist, who has published on the role of yeast heat shock protein 90 in glucocorticoid receptor gene transactivation in yeast additional studies using yeast have been undertaken to examine the role of heat shock proteins in androgen receptor function (Picard et al., 1990). DNA manipulations (Sambrook et al., 1989) and yeast methodology (Sherman et al., 1981) are well-known to those of skill in the art.

EXAMPLE 15

PREPARATION OF α-UR ANTIBODIES AND THEIR USE IN IMMUNOCYTOLOCALIZATION OF UR IN SITU

An important tool for monitoring UR function is the development of antibodies against various UR domains. Antibodies against UR were raised in rabbits using an oligopeptide from the DBD/hinge junction of UR (P-antibodies) or full-length UR (F-antibodies) as antigens. To generate antibodies with appropriate specificity, the following methodology has been employed. TrpE and other fusion proteins and various oligopeptides (10 to 15-mers of N- and C-terminal and internal sequences) are used as antigens to generate polyclonal (in rabbits) and monoclonal antibodies (in rats or mice). Many of these are available through commercial sources.

A 15-mer peptide, N-EAGMRESSVLSEEQI-amide (SEQ ID NO:21) was custom synthesized (Research Genetics, Huntsville, Ala.) and coupled to multiple antigen peptide (MAP). Rabbit polyclonal anti-serum was generated by standard immunization of two rabbits with above peptide antigen. Serum from one of the two rabbits showed, by ELISA, a high titer and was used for affinity purification.

Another 15-mer peptide, N-EAGREQCVLSEEQI-amide (SEQ ID NO:22) was synthesized and coupled to CNBr-activated Sepharose 4B (Pharmacia) using the method of the manufacturer. 5 mg of peptide was coupled to 7 ml wet Sepharose. About 65 ml of serum was loaded onto the column by an electric pump in a closed recycle system for 2 h at a rate of 5 ml/min. The column was washed for 1 h (at a pumping rate of 5 ml/min) and step eluted with elution buffer (3M $MgCl_2$, 75 mMHEPES [pH 7.2], and 25% ethylene glycol [vol/vol]) at a rate of 2.5 ml/min. The first 33 ml were collected and pooled. The effluent was dialyzed against 2 l PBS twice overnight and concentrated by vacuum dialysis for 36 h. The final volume was 15 ml (10 mg total). All the purification procedures were carried out at 4° C.

The creation of antibodies to UR provides an important utility in immunolocalization studies, and may play an important role in the diagnosis and treatment of receptor disorders. That these antibodies recognize different epitopes make them useful for rigorous immunochemical characterization and immunocytochemical localization of UR in a host of mammalian organs and cells. The utility of these antibodies in determining the intracellular location of receptor polypeptides in situ and in vivo is exemplified in FIG. 8A, FIG. 8B, FIG. 8C, and FIG. 8D. These results show that the antibodies of the present invention may be employed to identify tissues, organs, and cells which express UR. As exemplified in Example 16, the presence of UR may be related to developmental stages or the identification of hormonal abnormalities.

EXAMPLE 16

THE USE OF UR IN DETERMINING DEVELOPMENTAL STAGES IN SITU

To identify cells or organs in which UR plays a role, the UR antibodies of the present invention are useful in determining not only the intracellular localization of UR polypeptide in situ (See Example 15), but also in detecting changes in both the level and distribution of UR in cells of different organs during organ development.

One may, therefore, relate UR polypeptide level, and the expression of the UR-encoding genes to a developmental process of interest in these organs. One example of the use of the present invention in this manner concerns the detection of UR in mouse embryos at different stages of development. Immunocytochemical localization indicated that many but not all organs were stained at all stages. Different types of UR antibodies may be used to confirm the absence, presence, and relative amounts of UR in different cells.

The combined use of UR mutants and antibodies that recognize different epitopes of UR will be useful for this purpose. Required cells may be obtained from transgenic mice that harbor the SV40 tsA58 early region (Jat et al., 1991). The TAg gene is associated with tumorigenesis, however, the use of the thermolabile tsA58 in these transgenic mice reduces the level of functional TAg present, in vivo, at the body temperature of mice. Cells obtained from skin, thymus, brain, and liver expressed tsA58, were able to grow under permissive conditions (i.e., growth at 33° C. in the presence of IFN-γ), but not under nonpermissive conditions (i.e., growth at 39.5° C. in the absence of IFN-γ).

The $H-2K^b$-tsA58 transgenic mice will allow direct derivation of cell lines from a wide variety of tissues and cell types, including prostate cells. As cells from these transgenic mice are genetically homogeneous, they may be obtained in large numbers and may be synchronously exposed to interferon in vitro. Cells have been obtained from skin (poor in UR) and other organs from these "immortalized" transgenic mice and have established many cell lines.

Since immunocytochemical localization studies suggest that UR is expressed very weakly in skin compared to other organs, transgenic mice that over-express UR in skin cells will be obtained. For this purpose, a chimeric gene containing the keratin gene K14-promoter linked to UR cDNA will be constructed. Production of transgenic mice and subsequent analysis will follow the mouse embryo microinjection procedures outlined by Hogan, et al., (Hogan et al., 1986) and Murphy and Hanson (Murphy and Hanson, 1987).

Isolation, injection and other manipulations of preimplantation mouse embryos from transgenic mice may be examined for visual abnormality (including hair growth) and then with a light microscope to find any structural abnormality in the makeup of skin. Histopathological examination including hypertrophy, thickness, shape of cells and various layers of skins at different locations of the animals and also tongue, corneal, esophageal, and mammary epithelia, as well as liver, kidney and sexual organs may be coordinated with expression of UR to provide a complete diagnostic profile.

Antibodies to other receptors, such as AR, ER and various keratins may also be used to detect alterations in cellular localization of these proteins. Abnormality in skin histology and morphology (including psoriasis) or tumor formation may indicate UR involvement in the normal or abnormal skin development and differentiation.

EXAMPLE 17

GENERAL METHODS

Descriptions of general techniques commonly used in molecular biology are found in "Molecular Cloning, A Laboratory Manual" (Sambrook et al., 1989) and "DNA Cloning, C Practical Approach" vols. I, II, and III (Glover, 1985–1987).
Preparation and Screening of cDNA Libraries cDNA libraries were obtained commercially or constructed in the lambda phage Lambda ZAP™ II vector using commercially available kits. As probes, five synthetic oligonucleotide preparations whose sequences were derived from the sequences in the conserved DNA binding domain of steroid/thyroid receptor super family were prepared and pooled together. A pool of these oligonucleotides was end-labeled with T4 polynucleotide kinase and [γ-$^{32}$P]ATP.

For hybridization, nitrocellulose membranes (Schleicher and Schuell, Keene, N.H.) were used to blot phage DNA from plates. A total of $10^6$ phages from unamplified rat vagina Lambda ZAP™ II library were blotted and screened. The blotted membranes were incubated with the hybridization buffer (6× SSPE, 1× Denhardt's solution, 0.5% SDS, 1 mM EDTA, 100 μg/ml denatured salmon testis DNA) without probe first and then incubated with radioactive probes ($10^5$ cpm/ml) at 42° C. overnight in hybridization-buffer. The blotted nitrocellulose membranes were washed with 6× SSPE containing 0.5% SDS at room temperature for 1 h and then 50° C. for 10 min. Autoradiography was carried out at −80° C. overnight. Positive clones were picked and rescreened twice to obtain pure single phage clones. pBluescript® plasmids were excised from positive Lambda ZAP™ II phages according to methods of the manufacturer.

DNA and Deduced Amino Acid Sequence Analysis, PCR™ Techniques

For each positive clone, two separate PCR™ reactions were performed with one of the five oligonucleotide and either one of M13 −20 primer or M13 reverse primer. PCR™ products were analyzed by electrophoresis. Clones with amplified bands were identified and the amplified DNA fragments were further analyzed by DNA sequencing. PCR™ products were excised from agarose gels and purified. Double-stranded linear DNA sequencing was carried out under conditions described previously (Casanova et al., 1990; Hsiao, 1991). [α-$^{32}$P]dCTP was used as the radioisotope and autoradiography was performed on dried gels with Kodak X-OMAT AR film at room temperature overnight. Double-stranded plasmids (recovered pBluescript® plasmids) were used as templates for DNA sequencing using the alkaline denaturation method. [α-$^{35}$S]dCTP was used, with autoradiography being performed overnight at room temperature.

Analysis of UR genomic structure

To isolate UR gene segments for sequencing and determination of the UR genomic structure, a Lambda FixII™ human genomic library (Stratagene) was screened with $^{32}$P-labeled human UR cDNA (random priming labeling) Nitrocellulose filters were hybridized overnight in 5× SSPE, 5× Denhardt's reagent, 0.1% SDS and 100 μg/ml denatured sonicated salmon testis DNA at 42° C. Filters were washed twice with 2× SSC at room temperature for 30 min and washed twice for 1 h at 65° C. with 0.2× SSC. Filters were exposed to film for 18 h at −80° C.

Phage DNA was isolated, digested with endonucleases, and analyzed by Southern hybridization analysis with different fragments of hUR cDNA fragments as probes. Selected restriction fragments were subcloned into plasmids and sequenced.

Construction of Vectors and Retrovirus Encoding UR.

Untranslated sequence at the 5' terminus of the rUR cDNA was removed by introduction of a BamHI site by PCR™ immediately upstream of the initiation ATG. At the same time, a 12-bp adult rabbit α-globulin sequence was introduced upstream of the ATG.

PCR™ was performed with the above primers and R6.2 clone as template. A band of about 400-bp was recovered from agarose gels and digested with NcoI and BamHI. The R6.2 clone in pBluescript®is also digested with NcoII and BamHI and the larger fragment was ligated to the PCR™ fragment. The reconstructed clone was named R6.2ATG2. To remove most of the 3' untranslated sequence and the natural polyadenylation site, R6.2ATG2 was digested with AccI. An AccI site is located about 50 bp past the termination codon and an AccI site is also present in the vector multicloning site on the 3' side. The large fragment consisting of the vector and the R6.2ATG2 reading frame was blunt-ended and religated to create R6.2ATG2.ACCI. R6.2ATG2.ACCI was cut with XbaI and KpnI and the insert was cloned into the pGEM-7Z™ vector in the same sites to create pGEM7Z.R6.2.ATG2.ACCI. pGEM7Z.R6.2.ATG2ACCI was cut with BamHI and cloned into pSG5 to make pSG5/rUR; pGEM7Z.R6.2.ATG2.ACCI was also cut with BamHIi and blunt-ended and cloned into EcoRI site of the retroviral vector pMV7, a Moloney murine sarcoma virus-derived vector (Kirschmeier et al., 1988).

Retrovirus encoding rUR (pMV7-UR) was generated by transfection of the pMV7-R6.2.ATG2.ACCI vector into the mouse y2 packaging cell line using the calcium phosphate precipitation technique (Brown and Scott, 1987). After 2 weeks of selection in medium containing 0.4 mg/ml geneticin, low titer ecotrophic viral progeny produced from geneticin-resistant cells are used to infect mouse PA317 cells, which produced high titer amphotrophic retrovirus capable of infecting rodent and non-rodent cells lines.

Preparation of Fusion Proteins

PCR™ was performed with two primers using a rUR clone as template. An about 400-bp fragment was recovered from agarose gels and digested with NcoI and BamHI. The UR fragment was ligated to the PCR™ fragment after purified from agarose gels. The reconstructed clone, named R6.2ATG2, was cut with BamHI and HindIII and cloned into PATH2 (Koerner et al., 1991) vector through its multiple cloning site, giving PATH2/R6.2.ATG2. The fusion gene codes for 331 amino acids of the TrpE at the amino terminal which was followed by the entire rUR amino acid sequence.

The induction of the fusion gene was performed by a modification of the previously described method (Koerner et al., 1991). The fusion protein was analyzed by SDS-PAGE and used as antigen to generate polyclonal antibodies. The fusion protein may also be used to produce Monoclonal antibodies.

rUR may also be expressed as a glutathione-S-transferase fusion protein with pGEX vector. pGEM7Z/R6.2.ATG2.ACCI is cut with XbaI and XhoI and cloned inframe into pGEX-KG. Induction and purification procedures have been previously described (Smith and Corcoran, 1990). The GST fusion protein is soluble and may also be used in DNA binding assays as well as antibody purification.

A 15-mer amino terminal peptide custom synthesized has been and coupled to a multiple-antigen peptide (MAP) to generate polyclonal antibodies in rabbits. Serum from rabbits showed a high titer by ELISA, and was used for affinity-purification. The affinity purified antibodies were then used in immunocytochemical localization studies. A 15-mer peptide, representing the hinge region of rUR was synthesized and coupled to MAP and used as an antigen to immunize rabbits to obtain anti-UR antibodies. The peptide was coupled to CNBr-activated Sepharose 4B and used in the affinity purification of the antibodies.

Immunocytochemical Localization of UR

Tissues were removed from 200 to 300-g Sprague-Dawley rats, immediately frozen in liquid nitrogen and stored at −135° C. Frozen tissue was embedded in Tissue-Tek O.C.T. compound (Miles, Elkhart, Ind.) and about 6- to 8-μm sections cut on a cryostat at −20° C. Sections were placed on gelatin-coated slides, air-dried for 3 min. and then placed in a picric acid-formaldehyde fixative for 10 min. Fixed tissue sections were washed in PBS (10 mM $NaH_2PO_4$, (pH 7.5), containing 150 mM NaCl), blocked with 10% normal goat serum in PBS for 10 min at room temperature and then incubated for 15–18 h at 4° C. with affinity-purified antibody to UR (1 μg/ml for rat tissues and 10 μg/ml for human tissues) in 1% normal goat serum in PBS. Cultured cells were grown on chamber slides and fixed in cold methanol before processing with antibody as described. Specificity of immunocytochemical staining was determined using purified rabbit IgG or antibody to UR preincubated for 18 h at 4° C. with the oligopeptides. Bound antibody was detected by incubating tissue sections with biotinylated goat anti-rabbit IgG (Zymed, So. San Francisco, Calif.) at 5 μg/ml in 1% normal goat serum in PBS for 10 min at room temperature and then with horseradish peroxidase-conjugated streptavidin (Zymed) at a dilution of 1:100 for 5 min at room temperature (Casanova et al., 1990). Peroxidase was visualized by incubating sections with 1.4 mM diaminobenzidine, 0.01% $H_2O_2$ in 50 mM Tris-HCl, (pH 7.2), for 2–5 min at room temperature. Slides were rinsed in PBS, dehydrated in ethanol, cleared in xylene, and mounted with a liquid cover.

Preparation of rUR DNA-Binding Domain

A segment of UR containing the DBD and a few amino acids of the hinge region (rUR amino acid residues 72 to 168) was expressed as a fusion protein using the E. coli expression vector PET15b and purified by affinity ($Ni^{+2}$/His-tag) chromatography. The DNA-binding ability of this domain was tested by gel shift analysis with a set of oligonucleotides that contained AGGTCA direct repeats with 0 to 6 oligonucleotide spacing. The UR fusion protein bound to all these direct repeats as a monomer, and optimum spacing for homodimer binding was 4 and 5 nucleotides, which is identical to a retinoic acid receptor response element (RARE). A hinge region peptide antibody super-shifted UR DBD homodimers bound to DR-4 and DR-5. Supershifting of monomer was not observed.

Gel-Shift Assays

In these studies gel-shift assays were carried out in a buffer containing 10 mM Tris-HCl, pH 8.0, 6% glycerol, 1 mM DTT, 0.1% NP-40™, 1 mM of polydeoxyinosine-poly deoxycytosine, and receptor protein(s). After incubation on ice, $^{32}$P-labeled oligonucleotide with HRE sequences was added and incubations continued for another 10 min. DNA protein complexes were resolved on 6% polyacrylamide gels at 4° C. in 23 mM Tris-HCl, 23 mM boric acid and 0.5 mM EDTA, pH8.0 (0.25× TBE). Gels were dried and subjected to autoradiography at room temperature.

For the gel-shift assays with in vitro expressed nuclear receptors, different binding conditions were used. pSG5, hRXRα, rUR, or pCDM8 (Invitrogen) with hTRα1 and hTRβ1 were transcribed in vitro and translated in a programmed modified reticulocyte lysate (Promega, Madison, Wis.) containing T7 RNA polymerase, 2 μl DNA at 1 μg/μl, 25 μl TNT lysate, 1 μl amino acid mixture lacking methionine, 4 μl 25 mM methionine, 1 μl RNAse inhibitor (40 U/μl), 1 μl T7 RNA polymerase (1 U/μl), 16 μl $ddH_2O$ at 30° C. for 90 min. The efficiency of in vitro expression was checked by analyzing the [$^{35}$S]-methionine-labeled product by TCA precipitation, SDS-PAGE electrophoresis, and by fluorography (Chamberlain, 1979). 2 μl lysate was incubated with 20 μl binding buffer (10 mM HEPES, [pH 7.9], 50 mM KCl, 2.5 mM $MgCl_2$, 2 mM DTT, 50 ng/μl poly(dI-dC), 250 ng/μl sonicated salmon testis DNA, and 10% glycerol) for 20 min on ice. Then 20 ng of labeled probe was added to the solution and was incubated for 10 min. on ice. The DNA-protein complexes were resolved using 5% PAGE in 23 mM Tris-HCl, (pH 8.0), 23 mM boric acid, and 0.5 mM EDTA. Gels were run at 6 W constant power for 3 h at 4° C., dried, and exposed to Kodak X-OMAT AR film at −80° C. overnight. For antibody supershift studies, 3 μg affinity-purified peptide antibody was added before the probe and the mixture incubated on ice an additional 30 min.

Construction of Expression Vectors and Cell Transfection Techniques

To investigate the role of UR in intact cells in transactivation of genes, transient expression of UR and other nuclear receptors were performed in Cos-1 cells. rUR, hRARα, and hRXRα cDNAs have been inserted into the pSG5 expression vector (Stratagene), while human TRα$_1$ and TRβ$_1$ cDNAs have been inserted into the pCDM8 (Invitrogen) vector. The TR expression vectors were generously provided by L. DeGroot. The rUR deletion mutants and other constructs were inserted into pSG5 for transient expression. The 4×DR-4 response elements were constructed by annealing $^{32}$P end-labeled complementary single-stranded oligonucleotides, partial ligation, restriction digestion with HindIII and SacI to cleave improper orientations, polyacrylamide gel purification of 4× constructs, and ligation into Hind-III-digested Δ56-c-fos CAT plasmid (Gilman et al., 1986). DNA Sequence and the orientation of response elements was confirmed DR-4 oligonucleotides were 26 nt:

5'-AGCTTTCAGGTCACAGGAGGTCAGAG-3' (SEQ ID NO:37)

and

5'-AGCTCTCTGACCTCCTGTGACCTGAA-3' (SEQ ID NO:38).

4×DR-0, DR-1, DR-2, DR-3, DR-5 and DR-6 reporter plasmids were constructed similarly. Natural HREs may also be inserted into either the HindIII or SacI sites of the Δ56-c-fos CAT vector. For transfection, COS-1 cells ($10^6$/plate) are plated onto 10-cm plates 24 h before transfection in DME supplemented with either 10% charcoal-stripped fetal bovine serum (FBS) or 10% AG 1-X8 resin-treated FBS. Treatment of FBS with the anion exchange resin AG 1-X8 (Bio Rad, Hercules, Calif.) has been shown to be an effective method of depleting serum of T3 and T4 (Samuels et al., 1979). Cells are transfected with expression vectors using the calcium phosphate precipitation procedure (Sambrook et al., 1989). Receptor expression vectors (4 μg) are cotransfected in duplicate plates alone or in combination with 8 μg of Δ56-c-fos CAT reporter plasmid containing hormone response elements along with 4 μg of pCH110 vector (Pharmacia) to provide β-Gal activity for normalization of transfection efficiency. pSG5 vector with no insert is added appropriately to equalize for the amount of DNA transfected per plate. Cells are incubated with precipitate for 8 h before a 7.5% glycerol shock. Fresh medium is added and hormones are added the next day. 30 h after the addition of hormone, cells are collected by scraping and subjected to 3 freeze-thaw cycles. Aliquots of cytosolic extract are assayed for β-Gal activity and the volume of extract containing 2 U of β-Gal activity, where 1 U is the activity which produces 1 μmole/min of o-nitrophenol from o-nitrophenol-β-D-galactoside at 37° C., is used in 2-h CAT assays. Acetylated [14C]-Cml is separated from non-acetylated mRNA Differential Display Technique

The RNA differential display technique was used to isolate cDNA fragments corresponding to mRNAs which are differentially expressed in different types of cells. The "RNAmap" provided by the GenHunter Corp. (Brookline, Mass.) has successfully been used for this technique. This method is a rapid, reproducible method of screening and comparing mRNA populations of two (or more) cell types. Briefly, cDNA is synthesized from RNA templates using 4 sets of partially-degenerate anchored oligo (dT) primers. Duplex fragments are generated by using these 3'-primers and a set of 20 5'-oligonucleotide primers and amplified the PCR™. [$\alpha$-$^{35}$S]dATP is incorporated during amplification so that labeled fragments may be visualized by autoradiography. Differentially expressed fragments may be easily identified in adjacent lanes, eluted, reamplified, subcloned and sequenced. The sequence and length of the primers is chosen to allow amplification of a large yet discernible population of cDNA fragments in any one reaction. A large proportion of the total mRNAs expressed by the cell theoretically should be amplified (Liang and Pardee, 1992). The feasibility of isolating differentially-expressed mRNAs using this method has been confirmed. Uni-Zap® (Stratagene) cDNA libraries of the 104-S and 104-R cell lines have been constructed for use in isolating complete cDNAs using the partial fragments generated by the Differential Display technique as probes.

Screening of UR-Associated Proteins

Host bacteria may be infected with Uni-Zap® phage from cDNA libraries and plated. About 3 h after plating, IPTG-impregnated nitrocellulose filters are placed onto the barely-visible plaques and incubation proceeds for another 3 to 6 h. β-Gal fusion proteins containing peptide sequences which interact with AR are induced and adsorb onto the nitrocellulose in a halo pattern as plaque development proceeds. Only those cDNAs which are in frame with the β-Gal gene are expressed as sense peptides, so therefore, only about 1 out of every 3 clones would be expected to express a sense β-Gal fusion peptide. However, because of the directed insertion of cDNAs into the Uni-Zap® vector during library construction, all of the cDNAs have the correct 5'- to 3'-orientation. Filters are lifted, blocked with nonfat dry milk and unlabeled control GST peptide, incubated with labeled GST-UR probe, and washed briefly to remove unbound probe (Kelin et al., 1992). These procedures have been used successfully to isolate new proteins which interact with c-fos and retinoblastoma gene products (Blanar and Rutter, 1992; Kaelin et al., 1992). Putative UR-associated factors may be characterized by a variety of in vitro DNA binding and transcription assays, as well as co-expression assays of AR-mediated gene transactivation in cultured cells.

Analysis of UR Function Using Yeast Expression Systems

Yeast-based screening systems have been used to define potential DNA response elements for the estrogen receptor (Nawaz et al., 1992) and the orphan receptor NGF1-B (Wilson et al., 1991). To determine the sequence of potential UR response elements, a modification of these methods were used which incorporated recent advances in phenotypic transactivation assay for yeast (Pierrat et al., 1992). UR is expressed in yeast using pG-1, a derivative of the 2-µ based yeast episomal plasmid, pGPD-2 (Schena and Yamamoto, 1988). DNA encoding UR, but lacking 5'- and 3'-untranslated regions, were subcloned into the unique BamHI site. Expression from this vector is controlled by the glycerol 3-phosphate dehydrogenase promoter, and auxotrophic selection is accomplished using the trpL gene. The reporter plasmid, also based on the yeast 2-µ episomal plasmid, contains a TATA box fused to the URA3 gene with upstream activating sequences deleted (Chang et al., 1989) and the reporter gene is preceded by a unique restriction site for insertion of either a library of synthetic degenerate oligonucleotides (Wilson et al., 1991; Nawaz et al., 1992), or a 100-500 bp rat genomic DNA MboI fragment (Wilson et al., 1991), representing potential DNA response elements. The reporter plasmid contains the HIS3 gene for auxotrophic selection and plasmid maintenance. A strain of S. cereviseae, RS109, (Mat a, ura3-52, his3-D200, ade2-101, lys2-801, leu2-D1, trpL-D901) is initially transformed (Gietz et al., 1992) with the UR expression vector and a yeast strain constitutively expressing UR is established under auxotrophic selection on tryptophan deficient media. These yeast are then transformed with the library of reporter plasmids and then examined for URA3 gene expression by assaying for growth on uracil-histidine- and tryptophan-deficient media, for resistance to 5-fluoroorotic acid (5-FOA), and for activity of orotidine-5'-monophosphate decarboxylase (OMPdecase) (URA3 gene product) (Pierrat et al., 1992). 5-FOA is converted to a toxic product by the URA3 gene product and is used in negative selection of URA3 expression. Colonies growing on uracil-deficient media and insensitive to 5-FOA cannot be expressing URA3 and are false positives. OMPdecase activity provides for quantitation of URA3 gene activation. Plasmids were rescued (Gietz et al., 1992) from yeast that grew on uracil-deficient media and that were sensitive to 5-FOA. The sequence of the putative response elements was determined by dideoxy chain termination sequencing of the promoter region of the reporter plasmid using primers flanking the site of insertion of the DNA containing potential response elements. Although several steroid, retinoid, thyroid, and vitamin D receptors as well as an orphan receptor activate gene transcription in yeast, there is the possibility that UR is not competent to activate gene transcription in yeast.

Various members of the steroid receptor superfamily interact with other members of this family as well as with other transcription factors to modulate gene transcription. To identify and clone genes for proteins that interact with UR, a modification of the published two-hybrid system developed by Fields and coworkers has been utilized (Chien et al., 1991). This system consists of two plasmids, one expressing the N-terminal DNA-binding domain of GAL4 and the other the C-terminal transactivation domain of GAL4, and a yeast reporter strain containing two integrated reporter genes (his-3 and lacZ) under the control of promoters binding GAL4. Two separate reporter genes eliminate many positives due to adventitious interaction of the test "false" proteins with DNA outside of the GAL4 binding sites. Plasmids are constructed to encode two hybrid proteins. One hybrid consists of the DNA-binding domain of GAL4 linked to a known protein (e.g., UR or one of its domains) and the other hybrid consists of the GAL4 transactivation domain linked through its C-terminus to protein sequences encoded by known DNA (e.g., other receptors or their domains) or a library of genomic fragments. The separate GAL4 domains may not interact to form a competent transcriptional activator; transcriptional activation from promoters containing GAL4-binding sites occurs only if the non-GAL4 components of the hybrids interact.

Components of this system (available commercially from ClonTech, Palo Alto, Calif.) include the S. cereviseae strain YPB2 and plasmids pGBT9 and pGAD424. YPB2 is derived from strain YM954. The genotype of YPB2 is MAT a, ura3-52, his3-200, ade2-101, lys2-801, trp1-901, leu2-3, 112, can$^R$, gal4-542, gal80-538, LYS::GAL1-HIS3, URA3::(GAL17mers)-lacZ. pGTB9 is a 2-μ based episomal expression vector containing TRP1 and GAL4 (residues 1-147) under the control of the ADH1 promoter. A polylinker follows codon 147 of GAL4 with five unique restriction sites for fusion of UR (or domains of UR) in frame with the GAL4 DNA-binding domain. pGAD424 is also a 2-μ based episomal expression vector containing LEU2, the ADH1 promoter, DNA encoding an initiation codon linked to the large T antigen nuclear localization signal (to enhance nuclear localization of the hybrid), the GAL4 (residues 768–881) transactivation domain, a polylinker with five unique restriction sites for fusion of test proteins, and the ADH1 terminator. Hybrids are most easily constructed using PCR™ and primers incorporating appropriate restriction sites that allow in frame ligation of test DNAs.

To determine what amino acid residues of UR may be critical for transcriptional activation, DNA-binding or putative ligand-binding, to random mutagenesis of selected regions of UR was conducted. The protocol of Yamamoto and coworkers (Schena et al., 1989), who studied mutations in the glucocorticoid receptor DNA-binding domain, may be adapted for use in the yeast expression and reporter systems cited above to screen for receptors with defects in transcriptional activation. DNA regions of UR to be mutagenized may be subcloned into the plasmid pBS/SK$^+$II and single-stranded DNA containing the test region prepared with helper phage. Single-stranded DNA is treated with sodium nitrite (deaminates C, A and G residues) (Myers et al., 1985) and double-stranded DNA prepared using reverse transcriptase and a T7 primer. Mutagenized, double-stranded DNA is cut with XhoI and SstI, the test fragment purified by agarose gel electrophoresis, and ligated to unmutagenized pBS/SK$^+$ cut with XhoI and SstI. The ligated mixture is used to transform competent $E.\ coli$ DH5α™ and plasmid DNA purified from a pool of transformed bacteria. Mutagenized receptor-domain inserts are excised from the plasmid pool, purified, and ligated into the yeast expression vector pG1-UR to replace the respective wild-type sequence. The pool of mutagenized yeast expression vectors is amplified in bacteria and used to transform yeast strain RS109. Transformed yeast are selected on minimal media (–his,–trp,+ura) containing 5-FOA. Clones insensitive to 5-FOA have defective gene transactivation and are candidates for mutations in critical amino acid residues required for UR function. Plasmids may be rescued from selected yeast, amplified in bacteria, purified and the mutagenized region sequenced.

EXAMPLE 18

PHYSIOLOGICAL FUNCTION OF UBIQUITOUS RECEPTOR

UR and AR Function in Prostate Cells and Other Organs

UR appears to interact with a network of nuclear receptors and their response elements. Elucidation of the role of UR in this network is important for understanding of whether UR affects the function of other nuclear receptors in modulating gene expression. UR is clearly involved in the regulation of the RXR/RAP and RXR/TR network. With breast cancer cell lines, it was shown recently that trans retinoic acid down-regulatedAR mRNA levels in T-47D (ER$^+$, PR$^+$) cells but up-regulated AR mRNA in MDA-MB-453 (ER$^-$, PR$^-$) cells (Nawz et al., 1992). The levels of AR mRNA were correlated with CAT reporter gene expression in the transfected cells. Like MDA-MB-453 cells, LNCaP cells are also ER$^-$ and PR$^-$. Vitamin D receptor, which heterodimerizes with RXR, has been shown recently to mediate vitamin D-induced cell receptor, which heterodimerizes with RXR, has been shown recently to mediate vitamin D-induced cell proliferation in LNCaP cells (Sai et al., 1990). Overexpression of UR, through competitive heterodimerization with EXR, might be expected to interfere with this proliferative pathway. In addition, it has been found that invasive PC-3 cells are rich in UR, while non-invasive LNCaP cells are not. It is important to know whether this new nuclear receptor plays a role in modulation of the expression of genes that are responsible for differences in the behavior of these cancer cells, for example, tumorigenicity and metastatic properties in animals.

Distribution of UR Isoforms in the Prostate and in Cancer Cells

UR may be considered as a member of a subfamily of nuclear receptors that include TR and RAR. These subfamily members often have several isoforms coded by multiple genes located at different chromosomal loci. TRs have α and β isoforms while RARs have α, β and γ isoforms. It is probable that UR also has multiple genes. If this is the case, it is important to study whether isoforms are prostate cancer cell-specific and may modulate androgen-dependent or -independent prostate cancer cell proliferation or gene expression. Since DBDs among different isoforms usually have a high homology, the DBD sequences of UR are used as probes (especially the second zinc finger of the UR which is probably coded by one exon) to screen genomic libraries or cDNA libraries of prostate cells for genes encoding UR isoforms. Using PCR™ techniques, restriction enzyme analysis, and DNA sequencing, the structure of the UR isoforms may be identified. If different isoforms are found, the structure may be deduced from their cDNAs. If the structures are sufficiently different, it may be possible to select different epitopes of different isoforms and produce isoform-specific antibodies. These antibodies may be used in many studies described in this application, including isoform expression and distribution in various organs or regions of prostate duct system and in prostate cells under the influence of different environmental factors. It has been observed that genomic DNA from PC3 cells gives a different pattern of restriction fragments hybridizing to UR cDNA that human liver DNA. This may indicate a possible translocation of UR genes in PC3 cells. Translocation involving other nuclear receptors (e.g., RAR) have been linked to malignancy.

UR Function in Prostate Cells

UR-poor cells (LNCaP cells, VPF and other fibroblasts) that may be infected with MV7-UR retrovirus to find out whether over-expression of UR in these cells may influence AR activity (proliferative stimulation and inhibition as well as transactivation of reporter gene expression by androgen), stroma-dependent epithelial cell differentiation, differential gene expression (studies by mRNA Differential Display technique) and tumorigenicity in nude mice. A comparison may be made between cells infected with MV7-rUR and control MV7 retrovirus in the appearance of androgen-induced differentiation markers. By comparing UR-regulated gene expression in different cell types under different hormonal environments (including steroids, T3, retinoic acid, serum factors, etc.), it may be possible to find a unique relationship among UR and AR functions.

In addition to the use of mRNA Differential Display method, prostate specific antigen (PSA) is used as a marker for LNCaP cells. Likewise, several rat prostate markers (positively and negatively regulated PBP, SBP, and sulphated glycoprotein-2) may be used as markers for rat and mouse prostate cell function. It has also been observed that UR-dependent transactivation of a report (CAT) gene is dependent on a factor in the serum. Therefore, the factor (or a new hormone) may play an important role in regulating the function of UR and AR in the prostate and other androgen-sensitive organs.

EXAMPLE 19

IN VITRO LIGAND BINDING ASSAYS USING UR POLYPEPTIDES

UR ligands may be produced by mammalian cells in the form of hormones. Some ligands may be involved in regulating the growth and/or development of normal organs, tissues, and cells. UR and its hormonal ligands may also be involved in the modulation of the growth, proliferation and metastasis of cancer cells.

Some of these activities may be dependent on UR/ligand regulation of the functions of receptors for TR, RAR, RXR, and vitamin D. Abnormality in UR function, either due to mutation or lack or normal UR, may be corrected by gene therapy including transgenic technology in vitro or in vivo. UR misfunction due to the lack or excess of UR ligand and/or regulatory factors can be corrected by the administration of the ligands/factors or antagonistic substances that interfere with UR interaction with the ligand and/or factor.

Some plants and microorganisms may produce ligands or factors that can regulate UR function. These substances can be screened using either rUR or hUR in an in vitro assay. This assay involves incubating suspected compounds in the presence of UR polypeptide or the ligand-binding domain of UR polypeptide in a buffer (such as 50 mM sodium phosphate, or Tris-HCl [pH 7.5]) in order for the compound to interact with UR. Subsequently a protease (such as trypsin, papain, or chymotrypsin) is added to the incubation mixture to partially degrade the UR protein or the ligand binding domain of UR protein.

A ligand which binds UR protects the UR protein from protease digestion, and is therefore distinguishable (using polyacrylamide gel electrophoresis or some other protein separation technique) from ligands which do not bind UR in which case the UR protein is itself degraded by the protease.

EXAMPLE 20

THE USE OF UR IN DETERMINING THYROID HORMONE ABNORMALITY

The molecular and cellular basis of generalized resistance to thyroid hormone (GRTH) is unclear. Many thyroid resistant patients have mutations in the TRβ gene which is on chromosome 17 and no mutations are located in the TRα gene on chromosome 3. However, in vitro studies have failed to find any significant differences between TRα$_1$ and TRβ$_1$, in terms of T3 binding (there are some differences in binding of thyroid analogs), DNA binding and heterodimerization (Samuel et al., 1993). TRβ mutations, therefore, may not be the determining factor, since it should be replaced by TRα. Functional impairment of TRβ is correlated with observations in vitro but not always in vivo.

The current hypothesis to explain such differences invokes variability of cofactors or diversity of genetic background that contribute in the action of thyroid hormone and thus, modulates the phenotype of GRTH (Refetoff et al., 1993). Such factors or genetic background have not been identified.

An important aspect of the present invention is the use of UR as a means of detecting and diagnosing thyroid hormone receptor mutations. The present work suggests that UR plays a regulatory role in TR interaction with TREs, and as such, UR may play a critical role in regulating thyroid hormone signal pathway. Therefore, by determining the function and expression of UR in subjects, it is possible to detect abnormal thyroid hormone function in these patients.

The use of UR in the diagnosis of thyroid hormone disorder represents a significant improvement over the prior art. Previously, thyroid hormone resistance has been most consistently demonstrated in vitro by measurement of the inhibitory effect of T3 on synthesis of fibronectin (Fn) and its mRNA in skin fibroblasts maintained in culture (Sobieszczyk and Refetoff, 1988). Significant differences between fibroblasts from normal individuals and those from subjects with GRTH were observed with the addition of physiological concentrations of T3. Measurement of the Fn response to T3 is the only in vitro test that holds some promise for the tissue diagnosis of GRTH by biochemical means (Refetoff et al., 1993).

By studying UR mRNA and UR levels in cells from normal individuals and patients with GRTH, one may determine the effect(s) of pMV7-UR infection on Fn production by these cells. DNA isolated from blood cells or fibroblasts of these patients may also be screened for possible mutations in the UR gene. The present invention has determined the DNA sequence of the human and rat UR genes. Exons of UR have been amplified by PCR™ techniques and analyzed by nucleotide sequencing, restriction fragment length polymorphism (RFLP) and single stranded conformational polymorphisms.

The inventors have detected UR in mouse embryos by immunocytochemical staining, and found that UR expression varies with tissue and stages of development. Thus, levels of UR may be related to developmental or cellular processes.

Many thyroid hormone resistant patients have mutations in the TRβ gene which is on chromosome 17 but no mutations are located in the TRβ gene on chromosome 3. However, in vitro studies have failed to find any significant differences between TRα1 and TRβ1, in terms of T$_3$ binding (there are some differences in binding of thyroid hormone analogs), DNA binding and heterodimerization. TRβ mutations, therefore, may not be the determining factor, since it should be replaced by TRα. Functional impairment of TRβ is correlated with observations in vitro but not always in vivo. The current hypothesis to explain such differences invokes variability of cofactors or diversity of genetic background that contribute to the action of thyroid hormone and thus, modulate the phenotype of general resistance to thyroid hormone. Since UR appears to play a possible regulatory role in TR interaction with TREs, UR may also play an important role in regulating the thyroid hormone signalling pathway. Abnormal UR function or expression may well be directly related to abnormal thyroid hormone function.

Although the make-up of the natural response elements for UR, RXR, RAR and TR in the control regions of various genes is undoubtedly more complex than the synthetic DR sequences used in this study, the interaction of UR with RXR as well as UR modulation of gene transactivation by TR and RAR suggest a mechanism in which a number of nuclear receptors of this subfamily, possibly including some yet to be discovered, interact in a composite fashion to yield a net transcriptional activity in the cell nucleus for a given response element. This net transcriptional activity is also dependent upon the presence of receptor ligands and the particular structure of the response element.

Because numerous modifications and variations in the practice of the present invention are expected to occur to those skilled in the art, only such limitations as appear in the appended claims should be placed thereon.

All of the compositions and methods disclosed and claimed herein may be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for or teach methodology, techniques and/or compositions employed herein.

Adelman et al., *DNA* 2:183, 1983.

Ali, M. and Vedeckis, W. V., *J. Biol. Chem.* 262:6778–6784, 1987.

Allan, G. F. et al., *Proc. Natl. Acad. Sci. USA* 89:11750–11754, 1992.

Amero, S. A. et al., *Mol. Endocrin.* 6:3–7, 1992.

Anderegg, R. J. et al., Correction of the cDNA-derived protein sequence of prostatic spermine binding protein: pivotal role of tandem mass spectroscopy in sequence analysis, *Biochemistry* 27:4214–4221, 1988.

Anderson, K. M. and Liao, S., Selective retention of dihydrotestosterone by prostatic nuclei, *Nature* 219:277–279, 1968.

Ausubel, F. M. et al., Expression and purification of lacZ and trpE fusion proteins, In: *Current Protocols in Molecular Biology*, pp 16.5–16.5.6, 1990.

Bachmann, B. et al., Improvement of PCR™ amplified DNA sequencing with the aid of detergents, *Nucl. Acids Res.* 18:1309, 1990.

Bertin, B. et al., *J. Biol. Chem.* 267(12):8200, 1992.

Bettuzzi, S. et al., Identification of the androgen-repressed mRNA for a 48-kilodalton prostate protein as sulfated glycoprotein 2 by cDNA cloning and sequence analysis, *Biochem. J.* 257:293–296, 1989.

Blanar, M. A. and Rutter, W. J., Interaction cloning: identification of a helix-loop-helix zipper protein that interacts with c-Fos, *Science* 256:1014–1018, 1992.

Boshart et al., *Cell* 41:521, 1985.

Bouvier, M. et al., *Mol. Pharmacol.* 33:133, 1988.

Brown, A. M. C. and Scott, M. R. D., Retroviral vectors. In: Glover D (ed) DNA Cloning, a Practical Approach. IRL Press, Oxford, pp. 189–212, 1987.

Brown, T. R. et al., Deletion of the steroid-binding domain of the human AR gene in one family with complete androgen insensitivity syndrome: evidence for further genetic heterogeneity in this syndrome, *Proc. Natl. Acad. Sci. USA* 85:8151–8155, 1988.

Bruchovsky, N. and Wilson, J. D., The conversion of testosterone to 5α-androstan-17β-ol-3-one by rat prostate in vivo and in vitro, *J. Biol. Chem.* 243:2012–2021, 1968.

Carlberg, C., Two nuclear signalling pathways for vitamin D, *Nature* 361:657–660, 1993.

Carson-Jurica, M. A. et al., Steroid receptor family: structure and functions, *Endocrin. Rev.* 11:201–220, 1990.

Casanova, J. L. et al., Optimal conditions for directly sequencing double-stranded PCR™ products with Sequenase, *Nucl. Acids Res.* 18:4028, 1990.

Chamberlain, J. P., Fluorographic detection of radioactivity in polyacrylamide gels with the water-soluble fluor, sodium salicylate, *Anal. Biochem.* 98:132–135, 1979.

Chang, C. et al., Characterization of new members in the steroid receptor superfamily. In: Carlstedt-Duke J, Eriksson H, Gustafsson J-A (ed) The Steroid/Thyroid Hormone Receptor Family and Gene Regulation. Birkhauser Verlag, Basel, p. 183–193, 1989.

Chang, C. et al., Fusion proteins containing AR sequences and their use in the production of poly-and monoclonal anti-AR antibodies, *Endocrin.* 123:1097–1099, 1989.

Chang, C. et al., Identification of glutathione S-transferase Yb1 mRNA as the androgen-repressed mRNA by cDNA cloning and sequence analysis, *J. Biol. Chem.* 262:11901, 1987.

Chang, C. et al., Isolation and characterization of human TR3 receptor: a member of the steroid receptor superfamily, *J. Steroid Biochem.* 34:391–395, 1989.

Chang, C. et al., Molecular cloning and structural analysis of complementary DNA of human and rat AR, *Prog. Clin. Biol. Res.* 32:53–63, 1990.

Chang, C. et al., Molecular cloning of new human TR2 receptors: a class of steroid receptor with multiple ligand-binding domains, *Biochim. Biophys. Res. Comm.* 165:735–741, 1989.

Chang, C. et al., Prostatic spermine-binding protein: cloning and nucleotide sequence of cDNA, amino acid sequence and androgenic control of mRNA level, *J. Biol. Chem.* 262:2826–2831, 1987.

Chang et al., *Nature* 375:615, 1978.

Chen, C. et al., Prostate α-protein: Isolation and characterization of the polypeptide components and cholesterol binding, *J. Biol. Chem.* 257:116–121, 1982.

Chien, C. T. et al., The two-hybrid system: a method to identify and clone genes for proteins that interact with a protein of interest, *Proc. Natl. Acad. Sci. USA* 88:9578–9582, 1991.

Crea et al., *Proc. Natl. Acad. Sci. USA* 75:5765, 1978.

Danboldt, N. C. et al., *Biochemistry* 29(28):6734, 1990.

Danielsen, M. et al., Two amino acids within the knuckle of the first zinc finger specify DNA responsive element activation by the GR, *Cell* 57:1131–1138, 1989.

Davis, I. J. et al., Transcriptional activation by Nur77, a growth factor-inducible member of the steroid hormone receptor superfamily, *Mol. Endocrinol.* 5:854–859, 1991.

De Luca, L., Retinoids and their receptors in differentiation, embryogenesis, and neoplasia, *FASEB. J.* 5:2924–2933, 1991.

Diamond, M. I. et al., Transcription factor interactions: selectors of positive or negative regulation from a single DNA element, *Science* 249:1266–1272, 1990.

Durand, B. et al., All-trans and 9-cis RA induction of CRABPII transcription is mediated by RAR-RXR heterodimers bound to DR1 and DR2 repeated motifs, *Cell* 71:73–85, 1992.

European Patent Application, Publ. No. 0036776.

Evans, R. M., The steroid and thyroid hormone receptor superfamily, *Science* 240:889–895, 1988.

Fang, S. and Liao, S., AR:Steroid- and tissue-specific retention of a 17β-hydroxy-5α-androstan-3-one protein complex by cell nuclei of ventral prostate, *J. Biol. Chem.* 246:16–24, 1971.

Ferruti, P. and Tanzi, M. C., *Cris. Rev. Ther. Drug Carrier Syst.* 2:117–136, 1986.

Fiers et al., *Nature* 273:113, 1978.

Folkers, G. E. et al., The RAR-β2 contains two separate cell-specific transactivation domains, at the N-terminus and in the ligand-binding domain, *Mol. Endocrinol.* 7:616–627, 1993.

Forman, B. et al., Half-site spacing and orientation determines whether thyroid hormone and retinoic acid receptors and related factors bind to DNA response elements as monomers, homodimers, or heterodimers. *Mol. Endocrinol.* 6:429–442, 1992.

Forman, B. M. and Samuels, H. H., Interactions among a subfamily of hormone receptors: the regulatory zipper model, *Mol. Endocrinol.* 4:1293–1301, 1990.

Forman, B. M. and Samuels, H. H., Dimerization among nuclear hormone receptors, *New Biol.* 2:587–594, 1990.

Forman, B. M. et al., A domain containing leucine-zipper-like motifs mediate novel in vivo interactions between the thyroid hormone and retinoic acid receptors, *Mol. Endocrinol.* 3(10):1610–1626, 1989.

Freedman, L. P., Anatomy of the steroid receptor zinc finger region, *Endocrine Rev* 13:129–145, 1992.

Gabizon, A. et al., *Cancer Res.* 50:6371–6378, 1990.

Gietz, D. et al., Improved method for high efficiency transformation of intact yeast cells, *Nucl. Acids Res.* 20:1425, 1992.

Giguere, V. et al., Identification of a new class of steroid hormone receptors, *Nature* 331:91–94, 1988.

Gilman, M. Z. et al., Multiple protein-binding sites in the 5'-flanking region regulate c-fos expression, *Mol. Cell Biol.* 6:4305–4316, 1986.

Glover, D. M., DNA cloning, a Practical Approach. Oxford:IRL Press, Volumes I–III, 1985–1987.

Godowski, P. J. et al. Signal transduction and transcriptional regulation by GR-lexA fusion proteins, *Science* 241:812, 1988.

Goeddel et al., *Nature* 281:544, 1979.

Goeddel et al., *Nucl. Acids Res.* 8:4057, 1980.

Guan, K. and Dixon, J. E., Eukaryotic proteins expressed in E. coli: an improved thrombin cleavage and purification procedure of fusion proteins with glutathione-S-transferase, *Anal. Biochem.* 192:262–267, 1991.

Heery, D. M. et al., Efficient transactivation by RAR in yeast requires RXRs, *Proc. Natl. Acad. Sci. USA* 90:4281–4285, 1993.

Herschman, H. R., Primary response genes induced by growth factors and tumor promotors, *Annu. Rev. Biochem.* 60:281–319, 1991.

Hess et al., *J. Adv. Enzyme Reg.* 7:149, 1968.

Hiipakka and Liao, *J. Biol. Chem.* 263:17590, 1988.

Hiipakka, R. A. et al., Expression of 5α-reductase in bacteria as a trp E fusion protein and its use in the production of antibodies for immunocytochemical localization of 5α-reductase, *J. Steroid Biochem* 45:539–548, 1993.

Hiipakka, R. A. et al., Molecular probes of the structures and functions of androgen receptors. In: Endocrine-dependent tumors. Raven Press, New York, pp 43–67, 1991.

Hitzeman et al., *J. Biol. Chem.* 255:2073, 1980.

Hogan, B. et al., Manipulating the mouse embryo. A laboratory manual. Cold Spring Harbor Press, Cold Spring Harbor, N.Y., 1986.

Holland et al., *Biochemistry* 17:4900, 1978.

Honda, S. et al., Ad4BP regulating steroidogenic P-450 gene is a member of SR superfamily. *J. Biol. Chem.* 268:7494–7502, 1993.

Hsiao, K-C., A fast and simple procedure for sequencing double stranded DNA with sequenase, *Nucl. Acids Res.* 19:2787, 1991.

Itakura et al., *Science* 198:1056, 1977.

Jat, P. S. et al., Direct derivation of conditionally immortal cells lines from an H-2Kb-tsA58 transgenic mouse, *Proc. Natl. Acad. Sci. USA* 88:5096–5100, 1991.

Jones, *Genetics* 85:12, 1977.

Kaelin, W. G. et al., Expression cloning of a cDNA encoding a retinoblastoma-binding protein with E2F-like properties, *Cell* 70:351–364, 1992.

King et al., *Science* 250:121, 1990.

Kingsman et al., *Gene* 7:141, 1979.

Kirschmeier, P. T. et al., Construction and characterization of a retroviral vector demonstrating efficient expression of cloned cDNA sequences, *DNA* 7:219–225, 1988.

Kliewer, S. A. et al., Convergence of 9-cis retinoic acid and peroxisome proliferator signaling pathways through heterodimer formation of their receptors, *Nature* 358:771–774, 1992.

Kliewer, S. A. et al., RXR interacts with nuclear receptor in retinoic acid, thyroid hormone and vitamin $D_3$ signaling, *Nature* 355:446–449, 1992.

Koerner, T. J. et al., High-Expression Vectors with multiple cloning sites; for construction of trpE fusion genes: pATH vectors, *Methods Enzymol.* 194:477–490, 1991.

Kokontis, J. et al., Expression and function of normal and LNCaP AR in androgen-insensitive human prostatic cancer cells: altered hormone and antihormone specificity in gene transactivation, *Receptor* 1:271–279, 1991.

Kokontis, J. et al., Transcriptional activation by TR3 receptor, a member of the steroid receptor superfamily, *Receptor* 1:261–270, 1991.

Kozak, M., An analysis of 5'-noncoding sequence from 699 vertebrate messenger RNAs, *Nucl. Acids Res.* 20:8125–8135, 1987.

Kozlowski, J. M. et al., Metastatic behavior of human tumor cell lines grown in the nude mice, *Cancer Res.* 44:3522–3529, 1984.

Kruse and Patterson, eds. *Tissue Culture*, Academic Press 1973.

Kyprianou, N. et al., Programmed cell death during regression of PC-82 human prostate cancer following androgen ablation, *Cancer Res.* 50:3748–3753, 1990.

Kyte and Doolittle, *J. Mol. Biol.*, 157:105–132, 1982.

La Spada, A. R. et al., AR gene mutations in X-linked spinal and bulbar muscular atrophy, *Nature* 352:77–79, 1991.

LaCasse, E. C. et al., Identification of binding proteins for nuclear localization signals of the glucocorticoid and thyroid hormone receptors, *Endocrinology* 132:1017–1025, 1993.

Lau, L. F. and Nathans, D. Expression of a set of growth-related immediate early genes in BALB/c 3T3 cells: coordinate regulation with c-fos or c-myc, *Proc. Natl. Acad. Sci. USA* 84:1182–1186, 1987.

Laudet, V. et al., Evolution of the nuclear receptor gene superfamily, *EMBO J.* 11:1003–1013, 1992.

Law, S. W. et al., Identification of a new brain-specific transcription factor, NURR1, *Mol. Endocrinol.* 6:2129–2135, 1992.

Lazar, M. A., Thyroid hormone receptors: multiple forms, multiple possibilities, *Endocrine Rev.* 14:184–193, 1993.

Lee, C. and Gross, Dissection of three lobes of the rat prostate, *Prog. Clin. Biol. Res.* 239: 577–82, 1987.

Lee, C. et al., Prostatic ductal system in rats: regional variation in morphological and functional activities, *Biol. Reprod.* 43:1079–1086, 1990.

Lee, M. et al., Structure of the RXRα DNA binding domain: α Helix required for homodimeric DNA binding, *Science* 260:1117–1121, 1993.

Leid, M. et al., Purification, cloning, and RXR identity of the Hela cell factor with which RAR or TR heterodimerizes to bind sequences efficiently, *Cell* 68:377–395, 1992.

Liang, P. and Pardee, A., Differential display of eukaryotic messenger RNA by means of the polymerase chain reaction, *Science* 257:967–971, 1992.

Liang, T. et al., Anti-5α-reductase antibodies in the serum of patients with prostate cancer, *J. Clin. Endocrinology and Metabolism* 71:1666–1668, 1990.

Liang, T. et al., Selective polyamine-binding proteins: Spermine binding by an androgen-sensitive phosphoprotein, *Biochim Biophys Acta* 542:430–441, 1978.

Liao, S. and Williams-Ashman, H. G., An effect of testosterone on amino acid incorporation by prostatic ribonucleoprotein particles, *Proc. Natl. Acad. Sci. USA* 48:1956–1964, 1962.

Liao, S. and Witte, D., Autoimmune anti-androgen receptor antibodies in human serum, *Proc. Natl. Acad. Sci. USA* 82:8345–8348, 1985.

Liao, S. et al., ARs: structures, mutations, antibodies and cellular dynamics, *J. Steroid Biochem.* 34:41–51, 1989.

Liao, S. et al., Interaction of ribonucleoprotein particles and sex-steroid-receptor complexes: a model for receptor recycling and possible function, *Exerpta Medica Int. Congr. Ser.* 273:404–407, 1972.

Liao, S. et al., Prostate α-protein: Complete amino acid sequence of the component that inhibits nuclear retention of AR complex, *J. Biol. Chem.* 257:122–125, 1982.

Liao, S. et al., Rapid effect of testosterone on ribonucleic acid polymerase activity of rat ventral prostate, *Endocrinology* 77:763–765, 1965.

Liao, S. et al., Ribonucleoprotein binding of steroid receptor complexes, *Nature* 241:211–213, 1973.

Liao, S. et al., RNA dependent release of androgen and other steroid-receptor complexes from DNA, *J. Biol. Chem.* 245:5545–5551, 1980.

Liao, S., Influence of testosterone on template activity of prostatic ribonucleic acids, *J. Biol. Chem.* 240:1236–1243, 1965.

Lighter, P. et al., *Human Genet.* 80:224–234, 1988.

Lubahn, D. B. et al., Sequence of the intron/exon junctions of the coding region of the human AR gene and identification of a point mutation in a family with complete androgen insensitivity, *Proc. Natl. Acad. Sci. USA* 86:9534–9538, 1990.

Lucas, P. C. and Granner, D. K., Hormone response domains in gene transcription, *Ann. Rev. Biochem.* 61:1131–1173, 1992.

Luisi, B. F. et al., Crystallographic analysis of the interaction of the GR with DNA, *Science* 352:497–505, 1991.

Lydon, J. P. et al., Differential modes of activation define orphan subclasses within the steroid/thyroid receptor superfamily, *Gene Expression* 2:273–283, 1992.

Lynch, J. P. et al., Steroidogenic factor 1, an orphan nuclear receptor, regulates the expression of the rat aromatase gene in gonadal tissues, *Mol. Endocrinol.* 7:776–786, 1993.

Mahmoudi, M. and Lin, V. K., Comparison of two different hybridization systems in northern transfer analysis, *Biotechniques* 7:331–333, 1989.

Mangelsdorf, D. J. et al., A direct repeat in cellular retinol-binding protein-II gene confers differential regulation by RXR and RAR, *Cell* 66:555–561, 1991.

Marcelli, M. et al., A single nucleotide substitution introduces a premature termination codon into the AR gene of a patient with receptor-negative androgen resistance, *J. Clin. Inv.* 85:1522–1528, 1990.

Marks, M. S. et al., H-2RIIBP (RXRβ) heterodimerization provides a mechanism for combinatorial diversity in the regulation of retinoic acid and thyroid hormone responsive genes, *EMBO J.* 11:1419–1435, 1992.

Masai, M. et al., Immuno-histochemical study of AR in benign hyperplastic and cancerous human prostates, *The Prostate* 17:293–300, 1990.

McDonnell, D. P. et al., Reconstitution of the vitamin D-responsive osteocalcin transcription unit in Saccharomyces cerevisiae, *Mol. Cell Biol.* 9:3517–3523, 1990.

Mendel, D. B. et al., Activation of cytosolic GR complexes in intact WEHI-7 cells does not dephosphorylate the steroid-binding protein, *J. Biol Chem.* 262:5644–5648, 1987.

Metzger, D. et al., The human ER functions in yeast, *Nature* 334:31–36, 1988.

Miller, J. et al., Repetitive zinc-binding domains in the protein transcription factor IIIA from Xenopus oocytes, *EMBO J.* 4:1609–1614, 1985.

Murphy, D. and Hanson, J., The production of transgenic mice by the microinjection of cloned DNA into fertilized one-cell eggs. In: Glover D (ed) DNA Cloning, a Practical Approach. IRL, Oxford, pp. 213–248, 1987.

Myers, R. M. et al., A general method for saturation mutagenesis of cloned DNA fragments, *Science* 229:242–247, 1985.

Näär, A. M. et al., The orientation and spacing of core DNA-binding motifs dictate selective transcriptional responses to three nuclear receptors, *Cell* 65:1267–1279, 1991.

Nakada, S. Y. et al., The AR status of neuroendocrine cells in human benign and malignant prostatic tissue, *Cancer Res.* 53:1967–1970, 1993.

Nakai, A. et al., A human early response gene homologous to murine nur77 and rat NGFI-B, and related to the nuclear receptor superfamily, *Mol. Endocrin.* 4:1438–1443, 1990.

Nawaz, Z., Identification of novel steroid-response elements, *Gene Expression* 2:39–47, 1992.

Nei, M., Molecular Evolutionary Genetics Columbia University Press, New York, N.Y., 293–298, 1987.

O'Malley, B. W. and Conneely, O. M., Orphan receptors: in search of a unifying hypothesis for activation, *Mol. Endocrinol.* 6:1359–1361, 1992.

O'Malley, *Mol. Endocrinol.* 4:363–369, 1990.

Okayama et al., *Mol. Cell Biol.* 3:280, 1983.

Owen et al., *Proc. Natl. Acad. Sci. USA* 87:9990–9994, 1990.

Picard, D. et al., Reduced levels of hsp90 compromise steroid receptor action in vivo, *Nature* 348:166–168, 1990.

Picard, D. et al., Signal transduction by steroid hormones: nuclear localization is differentially regulated in ER and GR, *Cell Reg.* 1:291–299, 1990.

Pierrat, B. et al., Functional analysis of the human ER using a phenotypic transactivation assay in yeast, *Gene* 119:237–24, 1992.

Power, R. F. et al., Dopamine activation of an orphan of the steroid receptor superfamily, *Science* 252:1546–1548, 1991.

Prior, L. et al., Replacement of arginine 773 by cysteine or histidine in the human AR causes complete androgen insensitivity with different receptor phenotypes, *Am. J. Hum. Genet.* 51:143–155, 1992.

Privalsky, M. L. et al., The viral erbA oncogene protein, a constitutive repressor in animal cells, is a hormone-regulated activator in yeast, *Cell* 63:1277–1286, 1990.

Purvis, I. J. et al., An androgen-inducible expression system for Saccharomyces cerevisiae, *Gene* 106:35–42, 1991.

Ranade, V. V., *J. Clin. Pharmacol.* 29:685–694, 1989.

Refetoff, S. et al., The syndromes of resistance to thyroid hormone, *Endocrine Rev.* 14:348–399, 1993.

Rennie, P. S. et al., Characterization of two cis-acting DNA elements involved in the androgen regulation of the probasin gene, *Mol. Endocrinol.* 7:23–36, 1993.

Ris-Stalpers, C. et al., Substitution of aspartic acid-686 by histidine or asparagine in the human AR leads to a functionally inactive protein with altered hormone-binding characteristics, *Mol. Endocrinol.* 5:1562–1569, 1991.

Rossini, G. P. and Liao, S., Intracellular inactivation, reactivation and dynamic status of prostate AR, *Biochem J.* 208:383–392, 1982.

Rowley, D. R. et al., Properties of an intermediate-sized AR: association with RNA, *Biochemistry* 25:6988–6995, 1986.

Rowley, J. D. et al., Mapping chromosome band 11q23 in human acute leukemia with biotinylated probes: Identification of 11q23 translocation breakpoints with a yeast artificial chromosome, *Proc. Natl. Acad. Sci. USA* 87:9358–9362, 1990.

Rubin, S. J. et al., Two prostate carcinoma cell lines demonstrate abnormalities in tumor suppressor genes, *J. Surg. Oncol.* 46:31–36, 1991.

Sai, T. et al., An exonic point mutation of the AR gene in a family with complete androgen insensitivity, *Am. J. Hum. Genet.* 46:1095–1100, 1990.

Sambrook, J. et al., Molecular Cloning: *A Laboratory Manual*, Cold Spring Harbor Laboratory Press, Cold Spring Harbor, N.Y., 1989.

Samuel, R. et al., The syndromes of resistance to thyroid hormone, *Endrocrine Rev.* 14:348–399, 1993.

Samuels, H. H. et al., Depletion of L-3,5,3'-triiodothyronine and L-thyroxine in euthyroid calf serum for use in cell culture studies of the action of thyroid hormone, *Endocrinology* 105:80–85, 1979.

Schena, M. and Yamamoto, K., Mammalian GR derivatives enhance transcription in yeast, *Science* 241:965–967, 1988.

Schena, M. et al., Mutations in the glucocorticoid receptor zinc finger region that distinguish interdigitated DNA binding and transcriptional enhancement activities, *Genes Develop.* 3:1590–1601, 1989.

Schmidt, T. J. and Litwack, G., Activation of the GR complex, *Physiol Rev.* 62:1131–1192, 1982.

Seeburg, *DNA* 1:239, (1982).

Sherman, F. et al., Methods in Yeast Genetics. Cold Spring Harbor Laboratory, Cold Spring Harbor, N.Y., 1981.

Siebwenlist et al., *Cell* 20:269, 1980.

Sladek, F. M. et al., Liver-enriched transcription factor HNF-4 is a novel member of the steroid hormone receptor superfamily, *Genes and Dev.*, 2353–2365, 1990.

Smith, D. B. and Corcoran, L. M., Expression and purification of glutathione-S-transferase fusion proteins. In: *Current protocols in molecular biology* 16.7.1–16.7.8, 1990.

Sobieszczyk, S. and Refetoff, S., Abnormal response of fibronectin mRNA to triiodothyronine in fibroblasts from patients with generalized resistance to thyroid hormone. *Endcrinology*, 121 Suppl:T-24, 1988.

Stinchcomb et al., *Nature* 282:39, 1979.

Stratford-Perricaudet et al., *Bone Marrow Trans. Suppl.* 1:151, 1992.

Tasset et al., *Cell* 62:1177, 1990.

Thomsen et al., *PNAS* 81:659, 1984.

Tora et al., *Cell* 58:477, 1989.

Tran, P. et al., COUP orphan receptors are negative regulators of retinoic acid response pathways, *Mol. Cell Biol.* 12:4666–4676, 1992.

Trifiro, M. et al., The 56/58 kDa androgen-binding protein in male genital skin fibroblasts with a deleted AR gene, *Mol. Cell Endo.* 75:37–47, 1991.

Truss, M. and Beato, M., Steroid hormone receptors: interaction with DNA and transcription factors, *Endocrine Rev.* 14:459–479, 1993.

Tschemper et al., *Gene* 10:157, 1980.

Umesono, K. and Evans, R. M., Determinants of target gene specificity for steroid/thyroid hormone receptors, *Cell* 57:1139–1146, 1989.

Umesono, K. et al., Direct repeats as selective response elements for the thyroid hormone, retinoic acid, and vitamin D3 receptors, *Cell* 65:1255–1266, 1991.

Veldscholte, J. et al., A mutation in the ligand binding domain of the AR of human LNCaP cells affects steroid binding characteristics and response to anti-androgens, *Biochem. Biophys. Res. Comm.* 173:534–540, 1990.

Wagner, A. J. et al., Myc-mediated apoptosis is blocked by ectopic expression of Bcl-2, *Mol. Cell Biol.* 13:2432–2440, 1993.

Wang, L. H. et al., COUP transcription factor is a member of the steroid receptor superfamily, *Nature* 340:163–166, 1989.

Webb, M. L. and Litwack, G., Association of RNA with the glucocorticoid receptor and possible role in activation. In: Biochemical Actions of Hormones Academic Press, New York, 13: 379–403, 1986.

West, N. B. et al., Localization and regulation of estrogen, progestin, and androgen receptors in the seminal vesicle of rhesus monkey, *J. Steroid Biochem Mol. Biol.* 37:11–21, 1990.

Wilson, T. et al., Participation of non-zinc finger residues in DNA binding by two nuclear orphan receptors, *Science* 256:107–110, 1992.

Wilson, T. E. et al., Identification of the DNA binding site for NGFI-B by genetic selection in yeast, *Science* 252:1296–1300, 1991.

Wilson, T. E. et al., The orphan receptors NGFI-B and steroidogenic factor 1 establish monomer binding as a 3rd paradigm of nuclear receptor-DNA interaction, *Mol. Cell Biol.* 13:5794–5804, 1993.

Yang, N. et al., Characterization of DNA binding and retinoic acid binding properties of RAR, *Proc. Natl. Acad. Sci. USA* 88:3559–3563, 1991.

Yang-Yen et al., *Cell* 62:1205–1215, 1990.

Yarbrough, W. G. et al., A single base mutation in the AR gene causes androgen insensitivity in testicular feminized rats, *J. Biol. Chem.* 265:8893–8900, 1990.

Yu, V. C. et al., RXRβ: A coregulator that enhances binding of retinoic acid, thyroid hormone, and vitamin D receptors to their cognate response elements, *Cell* 67:1251–1266, 1991.

Zelent, A. et al., Cloning of murine α and β retinoic acid receptors and a novel receptor γ predominantly expressed in skin, *Nature* 339:714–717, 1989.

What is claimed is:
1. An isolated nucleic acid encoding a mammalian ubiquitous, nuclear receptor polypeptide, said nucleic acid selected from the group consisting of;
   a) a nucleic acid encoding SEQ ID NO:2,
   b) a nucleic acid encoding SEQ ID NO:4,
   c) a nucleic acid which hybridizes to a nucleic acid having a nucleotide sequence which is the complement of the nucleotide sequence of SEQ ID NO:1 under conditions of high stringency, and
   d) a nucleic acid which hybridizes to a nucleic acid having a nucleotide sequence which is the complement of the nucleotide sequence of SEQ ID NO:3 under conditions of high stringency.

2. The isolated nucleic acid of claim 1, wherein said encoded polypeptide is a human or rat ubiquitous, nuclear receptor.

3. The isolated nucleic acid of claim 1, wherein said nucleic acid is a DNA molecule.

4. The isolated nucleic acid of claim 1 that encodes a polypeptide comprising the amino acid sequence of SEQ ID NO: 2 or SEQ ID NO: 4.

5. An expression vector comprising the nucleic acid of claim 1.

6. The expression vector of claim 5 wherein the nucleic acid comprises the nucleotide sequence of SEQ ID NO: 1 or SEQ ID NO: 3.

7. The expression vector of claim 5 wherein the nucleic acid comprises a base sequence that is identical or complementary to a segment of at least 15 contiguous bases of SEQ ID NO:1 or SEQ ID NO:3.

8. A recombinant cell transfected with the nucleic acid of claim 1.

9. The recombinant cell of claim 8 wherein the nucleic acid encodes a human or rat ubiquitous, nuclear receptor polypeptide.

10. The recombinant cell of claim 8 wherein the nucleic acid comprises the nucleotide sequence of SEQ ID NO: 1 or SEQ ID NO: 3.

11. The recombinant cell of claim 8 wherein the nucleic acid comprises a base sequence that is identical or complementary to a segment of at least 15 contiguous bases of SEQ ID NO:1 or SEQ ID NO:3.

12. A method of preparing a mammalian ubiquitous, nuclear receptor polypeptide, comprising:

transforming a cell with the nucleic acid of claim 1 to produce a ubiquitous, nuclear receptor polypeptide under conditions suitable for the expression of said polypeptide.

13. The nucleic acid of claim 1, that has the sequence set forth in SEQ ID NO: 1 or SEQ ID NO: 3.

14. The nucleic acid of claim 1 wherein the high stringency is defined as about 0.02M NaCl to about 0.15M NaCl at temperatures from about 50° C. to about 70° C.

15. A process of detecting in a sample an RNA that encodes the ubiquitous, nuclear receptor polypeptide encoded by the nucleic acid of claim 1, said process comprising the steps of:

contacting said sample under hybridizing conditions with the nucleic acid segment of claim 1 to form a duplex; and detecting the presence of said duplex.

16. An isolated DNA encoding a polypeptide comprising a ligand binding domain or a DNA binding domain of a mammalian ubiquitous, nuclear receptor polypeptide, said receptor polypeptide having an amino acid sequence as set fourth by SEQ ID NO: 2 or SEQ ID NO: 4.

17. An isolated DNA comprising a base sequence that is identical or complementary to a segment of at least 15 contiguous bases of SEQ ID NO: 1 or SEQ ID NO: 3.

* * * * *